(12) United States Patent
Croteau et al.

(10) Patent No.: US 7,153,676 B1
(45) Date of Patent: Dec. 26, 2006

(54) TRANSACYLASES OF THE PACLITAXEL BIOSYNTHETIC PATHWAY

(75) Inventors: Rodney B. Croteau, Pullman, WA (US); Kevin D. Walker, Pullman, WA (US); Anne Schoendorf, Collonges sous Saleve (FR); Mark R. Wildung, Colfax, WA (US)

(73) Assignee: Washington State University Research Foundation, Pullman, WA (US)

( * ) Notice: Subject to any disclaimer, the term of this patent is extended or adjusted under 35 U.S.C. 154(b) by 279 days.

(21) Appl. No.: 10/415,197

(22) PCT Filed: Sep. 29, 2000

(86) PCT No.: PCT/US00/27006

§ 371 (c)(1),
(2), (4) Date: Oct. 27, 2003

(87) PCT Pub. No.: WO01/23586

PCT Pub. Date: Apr. 5, 2001

Related U.S. Application Data

(63) Continuation-in-part of application No. 09/457,046, filed on Dec. 7, 1999, now Pat. No. 6,287,835, and a continuation-in-part of application No. 09/411,145, filed on Sep. 30, 1999, now abandoned.

(51) Int. Cl.
| | |
|---|---|
| *C12N 9/10* | (2006.01) |
| *C12N 1/20* | (2006.01) |
| *C12N 15/00* | (2006.01) |
| *C12N 5/00* | (2006.01) |
| *C12P 37/04* | (2006.01) |
| *C12P 21/00* | (2006.01) |

(52) U.S. Cl. .................... 435/193; 435/45; 435/69.1; 435/252.3; 435/252.8; 435/320.1; 435/325; 536/23.2

(58) Field of Classification Search ............... 536/23.1, 536/24.32, 45, 23.2; 435/320.1, 183, 471, 435/6, 69.1, 252.3, 325, 193; 800/295, 8
See application file for complete search history.

(56) References Cited

U.S. PATENT DOCUMENTS

| | | |
|---|---|---|
| 6,818,755 B1 | 11/2004 | Croteau et al. |
| 2002/0138859 A1 | 9/2002 | Croteau et al. |
| 2003/0108891 A1 | 6/2003 | Croteau et al. |

FOREIGN PATENT DOCUMENTS

| | | | |
|---|---|---|---|
| WO | WO 99/40216 | | 8/1999 |
| WO | WO 01/23586 A2 | * | 4/2001 |

OTHER PUBLICATIONS

GenBank Accession No. X66785, version X66785.1 (GI:30489), submitted to GenBank Jun. 7, 1992, last revised Aug. 11, 2005 at 9:43 AM.
GenBank Accession No. CAA47285, version CAA47285.1 (GI:30490), submitted to GenBank Jun. 7, 1992, last revised Aug. 11, 2005 at 9:43 AM.
GenBank Accession No. X66785, version X66785.1 (GI:30489), submitted to GenBank Jun. 7, 1992, last revised Jun. 7, 2000.
GenBank Accession No. CAA47285, version CAA47285.1 (GI:30490), submitted to GenBank Jun. 7, 1992, last revised Jun. 5, 2000.
U.S. Appl. No. 10/421,633, filed Apr. 21, 2003, Croteau et al.
Walker and Croteau, "Taxol biosythesis: Molecular cloning of a benzoyl-CoA:taxane 2α- O-benzoyltransferase cDNA from Taxus and functional expression in *Escherichia coli*," *PNAS*, 97:13591-13596, 2000.
Wildung and Croteau, "A cDNA Clone for Taxadiene Synthase, the Diterpene Cyclase That Catalyzes the Committed Step of Taxol Biosynthesis," *J. Biol. Chem.*, 271(16):9201-9204, 1996.
Zocher et al., "Biosynthesis of Taxol: Enzymatic Acetylation of 10-Deacetylbaccatin-III to Baccatin-III in Crude Extracts from Roots of Taxus baccata," *Biochem. Biophys. Res. Comm.*, 16-20, 1996.
GenBank Accession No. CAA47285 (1992).
GenBank Accession No. X66785 (1992).
Hezari and Croteau, "Taxol Biosynthesis: An Update," *Planta Medica*, 63:291-295, 1997.
Menhard and Zenk, "Purification and characterization of acetyl coenzyme A: 10-hydroxytaxane O-acetyltransferase from cell suspension cultures of *Taxus chinensi*," *Phytochemistry*, 50:763-774, 1999.
Pennington et al., "Acetyl CoA:10-deacetylbaccatin-III-10-O-acetyl transferase activity in leaves and cell suspension cultures of *Taxus cuspidate*," *Pharmaceuticals*, 49(8):2261-2266, 1998.
Walker and Croteau, "Molecular Cloning of 10-deacetylbaccatin-III-10-O-acetyl transferase cDNA from *Taxus* and functional expression in *Escherichia coli*," *PNAS*, 97(2):583-587, 2000.
Walker et al., "Molecular Cloning of a Taxa-4(20),11(12)-dien-5α-01-O-Acetyl Transferase cDNA from *Taxus* and Functional Expression in *Escherichia coli*," *Arch. Biochem. Biophys.*, 374(2):371-380, 2000.
Walker et al., "Partial Purification and Characterization of Acetyl Conenzyme A: Taxa-4(20),11(12)-dien-5α-ol O-Acetyl Transferase That Catalyzes the First Acylation Step of Taxol Biosynthesis," *Arch. Biochem. Biophys.*, 364:273-279, 1999.

* cited by examiner

*Primary Examiner*—Rebecca E. Prouty
*Assistant Examiner*—Ganapathirama Raghu
(74) *Attorney, Agent, or Firm*—Klarquist Sparkman, LLP

(57) ABSTRACT

Transacylase enzymes and the use of such enzymes to produce paclitaxel, related taxoids, as well as intermediates in the paclitaxel biosynthetic pathway are disclosed. Also disclosed are nucleic acid sequences encoding the transacylase enzymes.

17 Claims, 31 Drawing Sheets

Figure 1:
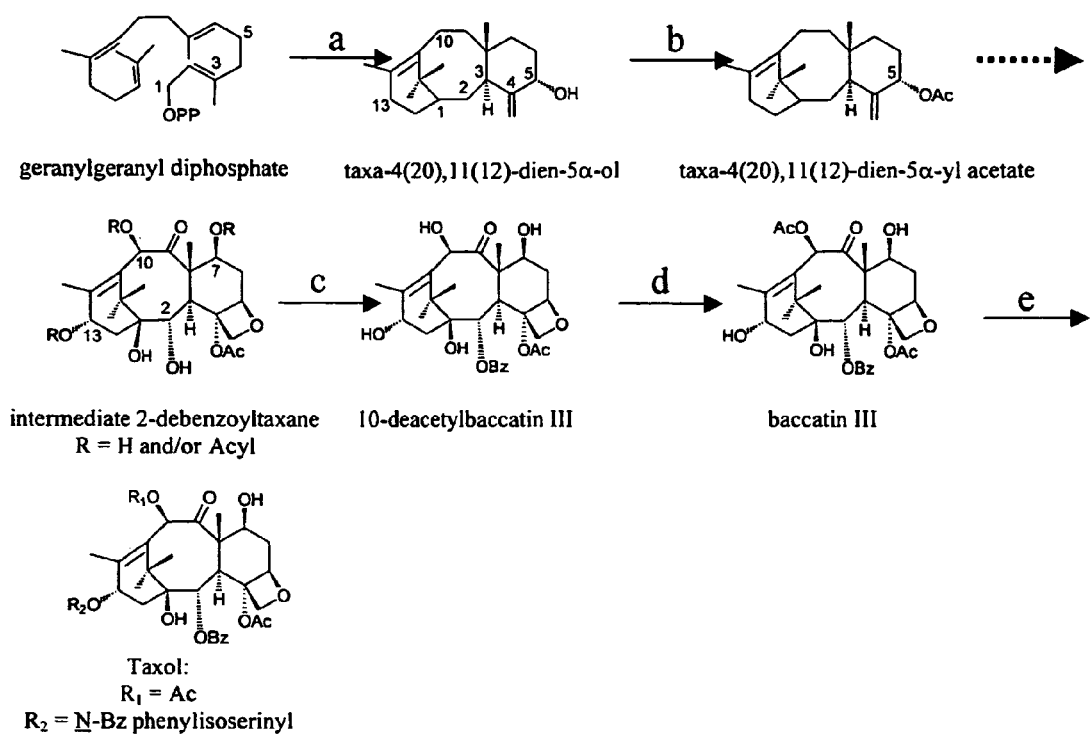

| Tryptic Peptide Fragment | Peptide Sequence |
|---|---|
| SEQ ID NO: 29 | TTLQLSSIDNLPGVR |
| SEQ ID NO: 30 | ILVYYPPFAGR |
| SEQ ID NO: 31 | FTCGGFVVGVSF |
| SEQ ID NO: 32 | KGLAEIARGEVK |
| SEQ ID NO: 33 | NLPNDTNPSSGYYGN |

Fig. 2

```
FROM PEPTIDE FRAGMENT SEQUENCE 2
NH2-   I    L    V    Y    Y    P    P   -COOH
5'    ATI  CTI  GTI  TAT  TAT  CCI  CC    3'        AT-FOR1
           T         C    C    C                    (SEQ ID NO: 34)
                     A         A

NH2-   Y    Y    P    P    F    A    G   -COOH
5'    TAT  TAT  CCI  CCI  TTT  GCI  GG    3'        AT-FOR2
       C    C    C    C    C    C                   (SEQ ID NO: 35)
                 A    A         A

FROM SEQUENCE HOMOLOGY CONSIDERATIONS
NH2-   F    Y    P    F    A    G    R   -COOH
5'    TTC  TAT  CCI  TTC  GCI  GGI  AG    3'        AT-FOR3
       T    C         T    C    C                   (SEQ ID NO: 36)
                           A    A

NH2-   Y    Y    P    L    A    G    R   -COOH
5'    TAC  TAT  CCI  TTI  GCI  GGI  AG    3'        AT-FOR4
       T    C    C         C    C C                 (SEQ ID NO: 37)
                           A    A

NH2-   D    F    G    W    G    K    P   -COOH
3'    CTA  AAA  CCI  ACC  CCI  TTT  GG    5'        AT-REV1
            G    G         C    C                   (SEQ ID NO: 38)
                 A         A
```

Fig. 4

| | | | | | | 50 | | | | | | | | | | |
|---|---|---|---|---|---|---|---|---|---|---|---|---|---|---|---|---|

TAX1 (SEQ ID NO: 28) . . . . . . . . . . . . . . . . . . . . . . . . . . . . . . . . . . . . . . . . . . . . . . . . . . . . .
TAX2 (SEQ ID NO: 26) . . . . . . . . . . . . . . . . . . . . . . . . . . . . . . . . . . . . . . . . . . . . . . . . . . . . .
aab61522 (SEQ ID NO: 61) . . . . . . . . . . . . . . . . . . . . . . . . . . . . . . . . . . . . . . . . . . . . . . . . . . . . .
aab61523 (SEQ ID NO: 62) . . . . . . . . . . . . . . . . . . . . . . . . . . . . . . . . . . . . . . . . . . . . . . . . . . . . .
aab95293 (SEQ ID NO: 63) . . . . . . . . . . . . . . . . . . . . . . . . . . . . . . . . . . . . . . . . . . . . . . . . . . . . .
aab97723 (SEQ ID NO: 64) . . . . . . . . . . . . . . . . . . . . . . . . . . . . . . . . . . . . . . . . . . . . . . . . . . . . .
aac17079 (SEQ ID NO: 65) M A A V S V A S A E L P P P P Q D G E T L S N V P Q T L S G E D C K K Q R I Q R P K S K N A E K C T
aac18062 (SEQ ID NO: 66) . . . . . . . . . . . . . . . . . . . . . . . . . . . . . . . . . . . . . . . . . . . . . . . . . . . . .
aac27152 (SEQ ID NO: 67) . . . . . . . . . . . . . . . . . . . . . . . . . . . . . . . . . . . . . . . . . . . . . . . . . . . . .
aac99311 (SEQ ID NO: 68) . . . . . . . . . . . . . . . . . . . . . . . . . . . . . . . . . . . . . . . . . . . . . . . . . . . . .
aad12025 (SEQ ID NO: 69) . . . . . . . . . . . . . . . . . . . . . . . . . . . . . . . . . . . . . . . . . . . . . . . . . . . . .
caa20531 (SEQ ID NO: 70) . . . . . . . . . . . . . . . . . . . . . . . . . . . . . . . . . . . . . . . . . . . . . . . . . . . . .
caa64636 (SEQ ID NO: 71) . . . . . . . . . . . . . . . . . . . . . . . . . . . . . . . . . . . . . . . . . . . . . . . . . . . . .
caa94432 (SEQ ID NO: 72) . . . . . . . . . . . . . . . . . . . . . . . . . . . . . . . . . . . . . . . . . . . . . . . . . . . . .
cab06427 (SEQ ID NO: 73) . . . . . . . . . . . . . . . . . . . . . . . . . . . . . . . . . . . . . . . . . . . . . . . . . . . . .
cab10318 (SEQ ID NO: 74) . . . . . . . . . . . . . . . . . . . . . . . . . . . . . . . . . . . . . . . . . . . . . . . . . . . . .
cab10319 (SEQ ID NO: 75) . . . . . . . . . . . . . . . . . . . . . . . . . . . . . . . . . . . . . . . . . . . . . . . . . . . . .
cab40761 (SEQ ID NO: 76) . . . . . . . . . . . . . . . . . . . . . . . . . . . . . . . . . . . . . . . . . . . . . . . . . . . . .

Fig. 6A

Fig. 6B

| | |
|---|---|
| TAX1 (SEQ ID NO: 28) | ................................................... 0 |
| TAX2 (SEQ ID NO: 26) | ................................................... 0 |
| aab61522 (SEQ ID NO: 61) | ................................................... 0 |
| aab61523 (SEQ ID NO: 62) | ................................................... 0 |
| aab95293 (SEQ ID NO: 63) | ................................................... 0 |
| aab97723 (SEQ ID NO: 64) | ................................................... 0 |
| aac17079 (SEQ ID NO: 65) | VKCVNTCIRSGDGEGPINIRRFQRIAWQIEGIQVTVSCFFVTCGKTRSSS 100 |
| aac18062 (SEQ ID NO: 66) | ................................................... 0 |
| aac27152 (SEQ ID NO: 67) | ................................................... 0 |
| aac99311 (SEQ ID NO: 68) | ................................................... 0 |
| aad12025 (SEQ ID NO: 69) | ................................................... 0 |
| caa20531 (SEQ ID NO: 70) | ................................................... 0 |
| caa64636 (SEQ ID NO: 71) | ................................................... 0 |
| caa94432 (SEQ ID NO: 72) | ................................................... 0 |
| cab06427 (SEQ ID NO: 73) | ................................................... 0 |
| cab10318 (SEQ ID NO: 74) | ................................................... 0 |
| cab10319 (SEQ ID NO: 75) | ................................................... 0 |
| cab40761 (SEQ ID NO: 76) | ................................................... 0 |

```
TAX1 (SEQ ID NO: 28) ..........................MEKTDLHYNLIEKVMVGRSPRL......P  23
TAX2 (SEQ ID NO: 26) ...........................MGRFNYDMIERVIVARCLQS.......P  21
aab61522 (SEQ ID NO: 61) ..........................................................  0
aab61523 (SEQ ID NO: 62) .........................MEKNYEILSREIVKRSSRIR......DD  22
aab95293 (SEQ ID NO: 63) .........................MPSLEKSYTIISRNRVFRDQKST......LV  25
aab97723 (SEQ ID NO: 64) ..................MASCIQELHFTHLHIPYTINQQFLVHRSSRIRANQSR  37
aac17079 (SEQ ID NO: 65) NNPHHTTFFILSENNNQMGEAAEQARGFHYTTRKQVITAALRLQ......DH  147
aac18062 (SEQ ID NO: 66) ..........................MNYTMHSKKLLKRSIRTR......NH  20
aac27152 (SEQ ID NO: 67) ........MGSSYQESPPLLEDLKYTIKESTLIFRSEET......SE  34
aac99311 (SEQ ID NO: 68) .....................MESGKISVETETLSKTLIKRSSRTR......QS  27
aad12025 (SEQ ID NO: 69) .........................MAPITFRKSYTIVRAERI......WS  20
caa20531 (SEQ ID NO: 70) ..................MANQRKPILPLLEKKPVELVKRSKHTHC......  29
caa64636 (SEQ ID NO: 71) ................MDSKQSSELVFTYRRQKPELIARAKRT......P  28
caa94432 (SEQ ID NO: 72) ...................DFSFHYRKCQPELIARANRT......P  21
cab06427 (SEQ ID NO: 73) ........................MSIQIKQSTMVRRAEET......PN  19
cab10318 (SEQ ID NO: 74) .......................METMTMKYETISKEIIKRSSRIR......NN  25
cab10319 (SEQ ID NO: 75) ....................MEAKLEVTGKEVIKRASRSR......RD  22
cab40761 (SEQ ID NO: 76) ........................MPMLMATRIDIIQKLNVYPRFQN  23
```

Fig. 6C

Fig. 6D

```
TAX1 (SEQ ID NO: 28)   REALAKILVYYPPEEAGRL.RETENGDLEVECTGE.GAMELEEAMADNELSV   114
TAX2 (SEQ ID NO: 26)   REALSKVLVYYPPEEAGRL.RNTENGDLEVECTGE.GAVFVEAMADNDLSV   108
aab61522 (SEQ ID NO: 61) . . . . . . . . . . . . . . . . . . . . . . . . . . . . . . . . . . . . . . . . . . . . . . . . . MSQ    3
aab61523 (SEQ ID NO: 62) KKSLSKTLPIFYPLAGRII.GS. . .FVEGNDEGAVFIEARVDH.LLSE   108
aab95293 (SEQ ID NO: 63) KHSLSITLTHFPPLAGRLS.TSSSGHVFLTCNDAGADFVFAQAKSIHVSD   111
aab97723 (SEQ ID NO: 64) QDALSEVLVPIYPLSGRL.REVENGKLEVFFGEEQGVLMVSANSSMDLAD   125
aac17079 (SEQ ID NO: 65) KTALAETLVSYYAEAGELV.TNPTGEPEILCNNRGVDFVEAGAD.VELRE   232
aac18062 (SEQ ID NO: 66) ESSLSETLTLYHVAGRYN.GT. . .DCVIECNDQGIGYVETAFD.VELHQ   103
aac27152 (SEQ ID NO: 67) RKALVKLMDAYEFLAGRLRVDPSSGRLDVDCNGA.GAGFVTAASDYTLEE   121
aac99311 (SEQ ID NO: 68) QNSLSKTLVSYYPEAGKVV.KN. . .DY.IHCNDDGIEFVEVRI.RCRMND   110
aad12025 (SEQ ID NO: 69) KTSLSRVLVHFYPMAGRLRWLP.RGRFELNCNAE.GVEFIEAESEGKLSD   106
caa20531 (SEQ ID NO: 70) RKALSELLVHYYPLSGKLMRSESNGKLQLVYLGE.GVPFEVATSTLDLSS   116
caa64636 (SEQ ID NO: 71) KKKAIAETLVFYYPEAGRL.REGNGRKLMVDCTGE.GIMFVEADADVTLEQ   116
caa94432 (SEQ ID NO: 72) KEAIGKALVFYYPLAGRL.REGPGRKLFVECTGE.GILFIEADADVSLEE   109
cab06427 (SEQ ID NO: 73) IEALSKALVPFYPMAGRLK.IN.GDRYEIDCNAE.GALFVEAESSHVLED   114
cab10318 (SEQ ID NO: 74) KTSLSETLTKFYPLAGRIT.GV. . . .TVDCTDEGAIFVDARVNNCPLTE   108
cab10319 (SEQ ID NO: 75) KLSLSETLSRFYPLAGRIE.GL. . . . SISCNDEGAVFTEARTDL.LLPD   101
cab40761 (SEQ ID NO: 76) KLGLEETMSVWYEAAGRLGLDGGGCKLNIRCNDGGAVMVEAVATGVKLSE   114
```

Fig. 6E

```
TAX1  (SEQ ID NO: 28) LGD.FDDSNPSFQ.QLLFSLPLDTNF......KDLSLHVVQYIRFTCG.GF 156
TAX2  (SEQ ID NO: 26) LQD.FNEYDPSFQ.QLVFNLREDVNI......EDLHLTVQYIRFTCG.GF 150
aab61522 (SEQ ID NO: 61) ILEN.PNPN.ELNKLHPFEFHEVSDVP.........LTVQLIFFECG.GL 41
aab61523 (SEQ ID NO: 62) FLKC.PVPE.SLELLIP...VEAKSRE...AVTWRVLIQANFSSG.GL 149
aab95293 (SEQ ID NO: 63) VIAGIDVPD.VVKEFFTYDR.AVSYE...GHNRRILAVQYIEIN..DGV 153
aab97723 (SEQ ID NO: 64) LGDLTVPNPAWLPLIFRNPGEEAYKI....LEMRLLIAQYIFFTCG.GF 169
aac17079 (SEQ ID NO: 65) LNLY.DPDE.SIAKLVPIKKHG.........VIAIQVIQLKCG.SI 266
aac18062 (SEQ ID NO: 66) FLLG.EESN.NLDLLVGL...SGFLSE....TETPRLAAIQLNMFKCG.GL 144
aac27152 (SEQ ID NO: 67) LGD.LVYPNPAFAQLVTSQLQ.SLPKD...DQRLFVFQITSFKCG.GF 163
aac99311 (SEQ ID NO: 68) ILKY.ELRS.YARDLVLPKRVTVGSED...TTA...IVQLSHFDCG.GL 150
aad12025 (SEQ ID NO: 69) FKD.FS.PTPEFENLM.PQVNYKNPIE...TIRLFLAQYIKFKCG.GI 147
caa20531 (SEQ ID NO: 70) LN......YIENLDDQVALRLVPEIEIDYESNVCYHPLALQVIKFACG.GF 160
caa64636 (SEQ ID NO: 71) FGDELQPPFPCLE.ELLYDVPDSAGV....LNCRLLLIQYIRLRCG.GF 159
caa94432 (SEQ ID NO: 72) FWDTLPYSLSSMQNNIIHNALNSDEV....LNSRLLLIQYIRLKCG.GF 153
cab06427 (SEQ ID NO: 73) FGD.FR.PNDELHRVMVPTCDYSKGIS...SFRLLMVQLTRFRCG.GV 156
cab10318 (SEQ ID NO: 74) FLKC.PDFD.ALQQLLPLDVVDNPYVA...AATWRLLLVKATYEGCG.GM 152
cab10319 (SEQ ID NO: 75) FLRN.LNTD.SLSGFLPTLAAGE...S...PAAWRLLSVKYIFFGSGSGV 143
cab40761 (SEQ ID NO: 76) LGDLTQYNEFYENLVYKPSLDGDFSV.........MFLVVAQYIRFACG.GY 156
```

Fig. 6F

| | | |
|---|---|---|
| TAX1 (SEQ ID NO: 28) | VVGVSFHHGVCDGRGAAQELKGLAEMAR.GEVKLS................ | LEPIW 195 |
| TAX2 (SEQ ID NO: 26) | VVGTREHHSVSDGKGIGQLLKGMGEMAR.GEFKPS................ | LEPIW 189 |
| aab61522 (SEQ ID NO: 61) | ALGIGLSHKLCDALSGLIEVNSHAAFARGQTDE.................. | HITRSF 80 |
| aab61523 (SEQ ID NO: 62) | VITICVSHKITDATSLAMFIRGHAESSRG..L................... | .GITLIRSF 187 |
| aab95293 (SEQ ID NO: 63) | FIGCSVNHAVTDGTSLWNEINTFAEVSRGAKNVT................. | RQPDFTRESVL 198 |
| aab97723 (SEQ ID NO: 64) | SLGIRLCHCICDGFGAMQELGSHAATAKTGKLIAD................ | ..PERVW 209 |
| aac17079 (SEQ ID NO: 65) | VVGCTFDHRVADAYSMNMELLSHAEISRSDVPI.................. | SCV..RSF 305 |
| aac18062 (SEQ ID NO: 66) | VIGAQFNHIIGDMFTMSTFMNSHAKACRVGIKE.................. | .VAHRTF 183 |
| aac27152 (SEQ ID NO: 67) | AMGISTNHTTFDGLSFKTELENLASLLH..EKPLS................ | TPRCN 201 |
| aac99311 (SEQ ID NO: 68) | AVAFGISHKVADGGTIASEMKDHAASACYLSSS.................. | HHVPTRLL 191 |
| aad12025 (SEQ ID NO: 69) | SLSVNVSHAIVDGQSALHLISEHGRLAR..GEPLE................ | TVRFL 185 |
| caa20531 (SEQ ID NO: 70) | TIGTALTHAVCRGYGVAQIIHALTELA.AGKTEPS................ | VKSVW 199 |
| caa64636 (SEQ ID NO: 71) | IFALRLNHTMSDAPGLVQEMTAVGEMAR.GGSAPS................ | ILRVW 198 |
| caa94432 (SEQ ID NO: 72) | IFGLCFNHTMADGFGIVQEMKATAEIAR.GAFAPS................ | ILRVW 192 |
| cab06427 (SEQ ID NO: 73) | SIGFAQHHHVCDGMAHFEENNSHARIAK..GLLPA................ | LERVH 194 |
| cab10318 (SEQ ID NO: 74) | AIGICITHKIADAASISTEIRSHAATARGENDA.................. | AAMESRVF 193 |
| cab10319 (SEQ ID NO: 75) | AVSVSVSHKICDIASLVTEVKDHATTTAKGKSN.................. | STIE...F 181 |
| cab40761 (SEQ ID NO: 76) | SIGIGTSHSLFDGISAYEEIHAHASNSHIHNKSNKITNKKEDVVIKRVH   | 206 |

Fig. 6G

```
TAX1  (SEQ ID NO: 28) NRELVKLD...DP..KYLQFFHF..EFLRAP.........SIV....EKIVQ 227
TAX2  (SEQ ID NO: 26) NREMVKPE...DI..MYLQFDHF..DFIHPP.........LNL....EKSIQ 221
aab61522 (SEQ ID NO: 61) DLAKMFPPCDIEN............LNMATGITKE....NIVT........ 107
aab61523 (SEQ ID NO: 62) TASEVFPKPLDEL.........PSKPMDRKEEVEEMS.CVT.......... 218
aab95293 (SEQ ID NO: 63) ISPAVLKVPQGGPKVTFDENAPLRERIFSFSRESIQELKAVVNKK...... 243
aab97723 (SEQ ID NO: 64) DRETFKPR...NP..PMVKYPHH..EYLPIEERSNLTNSLWD...TKPLQ 249
aac17079 (SEQ ID NO: 65) RRSLLNPRRRPLVMDPSIDQIYMPVTSLPPPQETTNPENLLAS....... 347
aac18062 (SEQ ID NO: 66) GLAPLMPSAKVLN.........IPPPPSFEG....VKFVS.......... 210
aac27152 (SEQ ID NO: 67) DRTLLKARDPPS.......VAFPHH..EL..VKFQDCETTTVFEATSEHLDF 242
aac99311 (SEQ ID NO: 68) VSDSIFPRQDNII..........CEQFPTSK....NCVE........... 216
aad12025 (SEQ ID NO: 69) DRKILWAGEPLPPFVSPPKFDHK..EFDQPPFLIGETDNVEERKKKTIV. 232
caa20531 (SEQ ID NO: 70) QRERLVGKIDNKP..GKVPGSHI...D....GFLATSAYLPT...TDVVT 237
caa64636 (SEQ ID NO: 71) CBELLNAR....NP..PQVTCTHH...EYDEVRDTKGTIIPL....DDMVH 236
caa94432 (SEQ ID NO: 72) QRALLTAR...DP..PRITFRHY..EYDQVVDMKSGLIPV....NSKID 230
cab06427 (SEQ ID NO: 73) DRYLHLRPRNPPQI......KYSHS..QFE..PFVPSLPNELLDGKTNKSQ. 235
cab10318 (SEQ ID NO: 74) AGANFYPPANEAF.................KLPADEQAGKRS.SIT... 221
cab10319 (SEQ ID NO: 75) AETTIYPPPPSHM.......YEQFPSTDSDSNITSKYVL.......... 213
cab40761 (SEQ ID NO: 76) DRNLLVNRDAVRETNAAAICHLYQLIKQAMMTYQEQNRNLELPDSGFVI 256
```

Fig. 6H

| | | |
|---|---|---|
| TAX1 (SEQ ID NO: 28) | TYEIIDFETINYIKQSV.MEEC................................. | ..KEF 251 |
| TAX2 (SEQ ID NO: 26) | ASMVISFERINYIKRCM.MEEC................................. | ..KEF 245 |
| aab61522 (SEQ ID NO: 61) | RREVFLRSSVESLREFSGNK................................... | KIR.AT 133 |
| aab61523 (SEQ ID NO: 62) | KREVFDASKIKKLRAK.ASRN.................................. | LVKNPT 244 |
| aab95293 (SEQ ID NO: 63) | KWLTVDNGEIDGVELLGKQSNDKLNGKENGILTEMLESLFGRNDAVSKPV | 293 |
| aab97723 (SEQ ID NO: 64) | KCYRISKEFQCRVKSIA.QGED................................. | ..PTL 273 |
| aac17079 (SEQ ID NO: 65) | RIYYIKANALQELQTLASSSKN................................. | .GKRT 373 |
| aac18062 (SEQ ID NO: 66) | KREVFNENAITRLRKEATEEDGDGDD.............................. | DQKKRRPS 244 |
| aac27152 (SEQ ID NO: 67) | KIEKLSSEQIKKLKERA..SET................................. | .SNG 265 |
| aac99311 (SEQ ID NO: 68) | KTEIFPPEAIEKLKSKAVEFG.................................. | IEKPT 242 |
| aad12025 (SEQ ID NO: 69) | VMLPLSTSQLQKLRSKANGSKH................................. | .SDP 257 |
| caa20531 (SEQ ID NO: 70) | ETINIRAGDIKRLKDSM.MKEC................................. | .EYL 261 |
| caa64636 (SEQ ID NO: 71) | KSEFFGPSEVSALRREV.PHHL................................. | .RK. 259 |
| caa94432 (SEQ ID NO: 72) | QLEFFSQLQISTLRQTL.PAHL................................. | .HD. 253 |
| cab06427 (SEQ ID NO: 73) | TLEILSREQINTLKQKLDLSNN................................. | .TTR 260 |
| cab10318 (SEQ ID NO: 74) | KREVFEASKVEDLRTKAASEE.................................. | TVDQPT 248 |
| cab10319 (SEQ ID NO: 75) | KREVFEPSKIAELKHKAASES.................................. | VPVPT 239 |
| cab40761 (SEQ ID NO: 76) | KTEELNGDAIESMKKKSLEG................................... | 276 |

Fig. 6I

```
TAX1 (SEQ ID NO: 28)  .CS..SFEVASAMTHIARTRAFQIPESEY..........VKILFGMDMENSFN 291
TAX2 (SEQ ID NO: 26)  .FS..AFEVVVALIHLARTKSFRIPPNEY..........VKIIFPIDMENSFD 285
aab61522 (SEQ ID NO: 61) RVE.....VLSVFIHSRF..MASTNHDDKTGKIYT...LIHPYNLERQAD 173
aab61523 (SEQ ID NO: 62) RVE.....AVTALFHRCV..TKVSRLSSLTPRTSV...LQILYNLBGKVD 284
aab95293 (SEQ ID NO: 63) AVEISSFQSLCALLHRAITRARKLPSSKTTT.......FRMAYNCRHRLS 336
aab97723 (SEQ ID NO: 64) VCS..TFDAMAAHIHRSWVKALDVKPLDYN........LRLTFSYNVRTRLE 315
aac17079 (SEQ ID NO: 65) KLE.....SFSAFLHKLVAEHAAKDPVPIKTSK......LGIVYDGRRRLM 413
aac18062 (SEQ ID NO: 66) RVD.....LVTAFLSKSLIEMDCAKKEQTKSRPSL...MVHMMNLRKRTK 286
aac27152 (SEQ ID NO: 67) NVRVTGFNVVTALVHRCKALSVAAEEGEET.NLERESTILYAYDIBGRL. 313
aac99311 (SEQ ID NO: 68) RVE.....VLTAFLSRCATVAGKSAAKNNNCGQSLPFPVLQAINLRPILE 287
aad12025 (SEQ ID NO: 69) AKGFTRYETVTGHVHRCACKARGHSPEQPT.AL.....GICIDTRSRM. 299
caa20531 (SEQ ID NO: 70) KESFTTYEVLSSYIHKLRSRALKLNPDGIT.....V.LGVAYGIRHVLD 304
caa64636 (SEQ ID NO: 71) .CS..TFELLTAVLHRCRTMSLKPDPEEE.........VRALCIYNARSBEN 299
caa94432 (SEQ ID NO: 72) .CP..SFEVLTAYVHRLRTIALQFKPEEE.........VRFLCVMNLRSKID 293
cab06427 (SEQ ID NO: 73) ..LSTYEVVAAHVHRSVSKARGLSDHEEI.KL.......IMPYDGRSRIN 300
cab10318 (SEQ ID NO: 74) RVE.....SVTALIWKCF..VASSK..TTTCDHKV...LVQLANLRSKIP 286
cab10319 (SEQ ID NO: 75) RVE.....AIMSLIWRCA..RNSSRSNLLIPRQAV...MWQAMDIRLRIP 279
cab40761 (SEQ ID NO: 76) .FMCSSFEFLAAHLWKARTRALGLRRDA..........MVCLQFAVDIRKRTE 318
```

Fig. 6J

```
TAX1 (SEQ ID NO: 28)   P.PLPSGYYGNSIGTACAVDNVQD..LLSG.SLLRAIMIIKKSKVSL...    334
TAX2 (SEQ ID NO: 26)   S.PLPKGYYGNAIGNACAMDNVKD..LLNG.SLLYALMLIKKSKFAL...    328
aab61522 (SEQ ID NO: 61) P.DIPDNMFGNIMRFSVTVPMMIIN..ENDEEKASLVDQMREEIRKI...  217
aab61523 (SEQ ID NO: 62) S..LCENTIGN.MLSLMI.LKNEE..AAIERIQDVVDEIRRAKEIF...  324
aab95293 (SEQ ID NO: 63) P.KLNPEYFGNAI.........QSVPTFATAAEVLSRDLKWC...     368
aab97723 (SEQ ID NO: 64) TLKLRKGFYGNVVCLACAMSSVES..HIND.SLSKTTRLVQDARLRV... 359
aac17079 (SEQ ID NO: 65) E.KENNTYFGNVLSVPFGGQRIDDLISKPLSWVTEEVHRFLKK....   455
aac18062 (SEQ ID NO: 66) L.ALENDVSGNFF.....IVVNA.ESKITVAPKITDLTESLGSA...   323
aac27152 (SEQ ID NO: 67) NPELPPSYTGNAVLTAYAKEKCKA..LLEE.PFGRIVEMVGEGSKRI...357
aac99311 (SEQ ID NO: 68) ..LPQNSVGNLVSIYFSRTIKENDYLNEKEYTKLVINELRKEKQKI... 331
aad12025 (SEQ ID NO: 69) EPPLPRGYFGNATLDVVAASTSGE..LISN.ELGFAASLISKAIKNV...343
caa20531 (SEQ ID NO: 70) P.PLPKGYYGNAYIDVYVELTVRE..LEES.SISNIANRVKKAKKTAYEK 350
caa64636 (SEQ ID NO: 71) P.PLPTGYYGNAFAFPVAVETAAK..LSKN.PLGYALELYKKTKSDV... 342
caa94432 (SEQ ID NO: 72) I.PL..GYYGNAVVVPAVITTAAK..LCGN.PLGYAVDLIRKAKAKA... 334
cab06427 (SEQ ID NO: 73) NPSLPKGYCGNVVFLAVCTATVGD..LSCN.PLTDTAGKVQEALKGL... 344
cab10318 (SEQ ID NO: 74) S.LLQESSIGNLMESSVV..LSIGR..GGEVKIEEAVRDLRKKEEL...  328
cab10319 (SEQ ID NO: 75) S.SVAPKDVIGNLQSGFS..LKKDA..ESEFEIPEIVATFRKNKERV... 321
cab40761 (SEQ ID NO: 76) T.PLPEGFSGNAYVLASVASTARE..LLEELTLESIVNKIREAKKSI... 362
```

Fig. 6K

Fig. 6L

```
TAX1   (SEQ ID NO: 28) G . FDEVDEFGHGNAYSVSPVQQQS . . ALAMQNYFLFLKPSKNKPDGIKILM 414
TAX2   (SEQ ID NO: 26) G . FYEADEFGHGNAYNVSPMQQQREHELAMQNYFLFLRSAKNMIDGIKILM 410
aab61522 (SEQ ID NO: 61) PVY . EADEGHGKRPLWVAS . . . . . . ARMS . YKNL . . VAFIDTKEGDGIEAWI 300
aab61523 (SEQ ID NO: 62) GLY . DADEGHGKRPYWVTG . . . . . . . . . . . . . . . . . MLLIDTKDGEGIEAWI 408
aab95293 (SEQ ID NO: 63) EMY . DNDEGHGRPYAVRS . . . . . . . RGTSHFKNL . . FPGREGNGTVDLEV 459
aab97723 (SEQ ID NO: 64) EMYETADEGHGKRPYYAGPI . . GRSNKFDGKISA . DLRPTPQVCVLLPQGGVESGNDQSMVVCL 441
aac17079 (SEQ ID NO: 65) PVN . QVDEFGHGSPYFGSY . . . . . . HFPWGGSAGYVMPMPSSVDDRDWMVYL 544
aac18062 (SEQ ID NO: 66) PLY . EVDEFGHGIESLVDT . . . . . TAVPF . . . GLIVLMDEAPAGDGIAVRA 412
aac27152 (SEQ ID NO: 67) G . FAEVEYPHGKRKYSCPVVYHRKDI . . . . . . . VLLFPDIDGDSKGVYVLA 431
aac99311 (SEQ ID NO: 68) PFY . DVDEFGHGKRIWV . C . . . . LFQPYIKNCVVMMDYPFGDDYGIEAIV 417
aad12025 (SEQ ID NO: 69) P . MYGLDEFGHGKEEYTGPGTHDEDGD . . . . . SLILPDQNEDG . SVILAT 433
caa20531 (SEQ ID NO: 70) GWFGSMDEGHGHNERYNLRPL . TQRESTVHVGMILKPSKSDPSMEGGVKVIM 435
caa64636 (SEQ ID NO: 71) G . FGEVDEGHGKAYYGGPAKGGVGAIPGVASFYIPFK . NKKGENGIVVPI 424
caa94432 (SEQ ID NO: 72) G . VENVDEFGHGKAIFGGPTTTGARITRGLVSFCVPFM . NRNGEKGTALSL 416
cab06427 (SEQ ID NO: 73) P . YQAMDEGHGSPTFFGISNIFYDGQ . . . . . CFLIPSRDGDG . SMTLAI 428
cab10318 (SEQ ID NO: 74) PLY . EASEGHDSRYWVVG . . . . NVSPVLGNL . . AMLIDSKDGQGIEAFV 418
cab10319 (SEQ ID NO: 75) PFY . EVDEGSRYWVGY . . . . ASHTIYDNMVGVVLIDSKEGDGVEAWI 407
cab40761 (SEQ ID NO: 76) P . FHNVGEGNG . . . . GEPADYMAPLCPPVPQVAYFMKNPKDAKGVLVRI 441
```

Fig. 6M

```
TAX1  (SEQ ID NO: 28) FLPLSKMKSFKIEMEAMMK.KYVAKV............       439
TAX2  (SEQ ID NO: 26) FMPASMVKPFKIEMEVTIN.KYVAKICNSKL........       440
aab61522 (SEQ ID NO: 61) NLDQNDMSRFEADEELLRYVSSNPSVMVSVS.....       331
aab61523 (SEQ ID NO: 62) TLTEEQMSLFECDQELLESASLNPPVLI........       436
aab95293 (SEQ ID NO: 63) VLSPETMAGIESDGEFMRYVTNK..............      482
aab97723 (SEQ ID NO: 64) CLPPTAVHTFTRLLSLNDHK..................     461
aac17079 (SEQ ID NO: 65) HLTKGQLRFIEEEASHVLKPIDNDYLKI........       572
aac18062 (SEQ ID NO: 66) CLSEHDMIQFQQHHQLLSYVS.................     433
aac27152 (SEQ ID NO: 67) ALPSKEMSKFQHWFEDTLC...................     450
aac99311 (SEQ ID NO: 68) SFEQEKMSAFEKNEQLLQFVSN................     439
aad12025 (SEQ ID NO: 69) CLQVAHMEAFKKHFYEDI...................      451
caa20531 (SEQ ID NO: 70) KLPRDAMVEFKREMATMKKLYFGDTN............     461
caa64636 (SEQ ID NO: 71) CLPGFAMETFVKELDGMLKVDAPL..VNSNYAIIRPAL    460
caa94432 (SEQ ID NO: 72) CLPPPAMERFRANVHASLQVKQVVDAVDSHMQTIQSASK   455
cab06427 (SEQ ID NO: 73) NLFSSHLSRFKKYFYDF.....................    445
cab10318 (SEQ ID NO: 74) TLPEENMSSFEQNPELLAFATMNPSVLV..........    446
cab10319 (SEQ ID NO: 75) SLPEEDMSVFVDDQELLAYAVLNPVVA...........    435
cab40761 (SEQ ID NO: 76) GLDPRDVNGFSNHFLDC.....................    458
```

TRANSACYLASES OF THE PACLITAXEL BIOSYNTHETIC PATHWAY

CROSS REFERENCE TO RELATED APPLICATIONS

The present application is the U.S. National Stage of International Application No. PCT/US00/27006, filed Sep. 29, 2000 published as PCT Publication No. WO 01/23586, which is a continuation-in-part of U.S. application Ser. No. 09/457,046, filed Dec. 7, 1999, now issued as U.S. Pat. No. 6,287,835, and a continuation-in-part of U.S. application Ser. No. 09/411,145, filed Sep. 30, 1999, now abandoned. Each of the foregoing applications are incorporated in its entirety.

ACKNOWLEDGMENT OF GOVERNMENT SUPPORT

This invention was made with government support under National Cancer Institute Grant No. CA-55254. The government has certain rights in this invention.

FIELD OF THE INVENTION

The invention relates to transacylase enzymes and methods of using such enzymes to produce paclitaxel and related taxoids.

INTRODUCTION

The complex diterpenoid paclitaxel (Wani et al., *J. Am. Chem. Soc.* 93:2325–2327, 1971) is a potent antimitotic agent with excellent activity against a wide range of cancers, including ovarian and breast cancer (Arbuck and Blaylock, *Taxol™: Science and Applications*, CRC Press, Boca Raton, 397–415, 1995; Holmes et al., *ACS Symposium Series* 583:31–57, 1995). Paclitaxel was originally isolated from the bark of the Pacific yew (*Taxus brevifolia*). For a number of years, paclitaxel was obtained exclusively from yew bark, but low yields of this compound from the natural source coupled to the destructive nature of the harvest, prompted new methods of paclitaxel production to be developed. Paclitaxel is currently produced primarily by semisynthesis from advanced taxane metabolites (Holton et al., *Taxol™: Science and Applications*, CRC Press, Boca Raton, 97–121, 1995) that are present in the needles (a renewable resource) of various *Taxus* species. However, because of the increasing demand for this drug (both for use earlier in the course of cancer intervention and for new therapeutic applications) (Goldspiel, *Pharmacotherapy* 17:110S–125S, 1997), availability and cost remain important issues. Total chemical synthesis of paclitaxel is not economically feasible. Hence, biological production of the drug and its immediate precursors will remain the method of choice for the foreseeable future. Such biological production may rely upon either intact *Taxus* plants, *Taxus* cell cultures (Ketchum et al., *Biotechnol. Bioeng.* 62:97–105, 1999), or, potentially, microbial systems (Stierle et al., *J. Nat. Prod.* 58:1315–1324, 1995). In all cases, improving the biological production yields of paclitaxel depends upon a detailed understanding of the biosynthetic pathway, the enzymes catalyzing the sequence of reactions, especially the rate-limiting steps, and the genes encoding these proteins. Isolation of genes encoding enzymes involved in the pathway is a particularly important goal, since overexpression of these genes in a producing organism can be expected to markedly improve yields of the drug.

The paclitaxel biosynthetic pathway is considered to involve more than 12 distinct steps (Floss and Mocek, *Taxol™: Science and Applications*, CRC Press, Boca Raton, 191–208, 1995; and Croteau et al., *Curr. Top. Plant Physiol.* 15:94–104, 1996), however, very few of the enzymatic reactions and intermediates of this complex pathway have been defined. The first committed enzyme of the paclitaxel pathway is taxadiene synthase (Koepp et al., *J. Biol. Chem.* 270:8686–8690, 1995) that cyclizes the common precursor geranylgeranyl diphosphate (Hefner et al., *Arch. Biochem. Biophys.* 360:62–74, 1998) to taxadiene (FIG. 1). The cyclized intermediate subsequently undergoes modification involving at least eight oxygenation steps, a dehydrogenation, an epoxide rearrangement to an oxetane, and several acylations (Floss and Mocek, *Taxol™: Science and Applications*, CRC Press, Boca Raton, 191–208, 1995; Croteau et al., *Curr. Top. Plant Physiol.* 15:94–104, 1996). Taxadiene synthase has been isolated from *T. brevifolia* and characterized (Hezari et al., *Arch. Biochem. Biophys.* 322:437–444, 1995), the mechanism of action defined (Lin et al., *Biochemistry* 35:2968–2977, 1996), and the corresponding cDNA clone isolated and expressed (Wildung and Croteau, *J. Biol. Chem.* 271:9201–9204, 1996).

The second specific step of paclitaxel biosynthesis is an oxygenation reaction catalyzed by taxadiene-5α-hydroxylase (FIG. 1). The enzyme, characterized as a cytochrome P450, has been demonstrated in *Taxus* microsome preparations to catalyze the stereospecific hydroxylation of taxa-4(5),11(12)-diene, with double bond rearrangement, to taxa-4(20),11(12)-dien-5α-ol (Hefner et al., *Chem. Biol.* 3:479–489, 1996).

The third specific step of paclitaxel biosynthesis appears to be the acetylation of taxa-4(20),11(12)-dien-5α-ol to taxa-4(20),11(12)-dien-5α-yl acetate by an acetyl CoA-dependent transacetylase (Walker et al., *Arch. Biochem. Biophys.* 364:273–279, 1999), since the resulting acetate ester is then further efficiently oxygenated to a series of advanced polyhydroxylated paclitaxel metabolites in microsomal preparations that have been optimized for cytochrome P450 reactions (FIG. 1). The enzyme has been isolated from induced yew cell cultures (*Taxus canadensis* and *Taxus cuspidata*), and the operationally soluble enzyme was partially purified by a combination of anion exchange, hydrophobic interaction, and affinity chromatography on immobilized coenzyme A resin. This acetyl transacylase has a pI and pH optimum of 4.7 and 9.0, respectively, and a molecular weight of about 50,000 as determined by gel-permeation chromatography. The enzyme shows high selectivity and high affinity for both cosubstrates with $K_m$ values of 4.2 μM and 5.5 μM for taxadienol and acetyl CoA, respectively. The enzyme does not acetylate the more advanced paclitaxel precursors, 10-deacetylbaccatin III or baccatin III. This acetyl transacylase is insensitive to monovalent and divalent metal ions, is only weakly inhibited by thiol-directed reagents and Co-enzyme A, and in general displays properties similar to those of other O-acetyl transacylases. This acetyl CoA:taxadien-5α-ol O-acetyl transacylase from *Taxus* (Walker et al., *Arch. Biochem. Biophys.* 364:273–279, 1999) appears to be substantially different in size, substrate selectivity, and kinetics from an acetyl CoA:10-hydroxytaxane O-acetyl transacylase recently isolated and described from *Taxus chinensis* (Menhard and Zenk, *Phytochemistry* 50:763–774, 1999).

Acquisition of the gene encoding the acetyl CoA:taxa-4(20),11(12)-dien-5α-ol O-acetyl transacylase that catalyzes the first acylation step of paclitaxel biosynthesis and genes encoding other acyl transfer steps would represent an important advance in efforts to increase paclitaxel yields by genetic engineering and in vitro synthesis.

SUMMARY OF THE INVENTION

The invention stems from the discovery of twelve amplicons (regions of DNA amplified by a pair of primers using the polymerase chain reaction (PCR)). These amplicons can be used to identify transacylases, for example, the transacylases shown in SEQ ID NOs: 26, 28, 45, 50, 52, 54, 56, and 58 that are encoded by the nucleic acid sequences shown in SEQ ID NOs: 25, 27, 44, 49, 51, 53, 55, and 57. These sequences are isolated from the *Taxus* genus, and the respective transacylases are useful for the synthetic production of paclitaxel and related taxoids, as well as intermediates within the paclitaxel biosynthetic pathway. The sequences can be also used for the creation of transgenic organisms that either produce the transacylases for subsequent in vitro use, or produce the transacylases in vivo so as to alter the level of paclitaxel and taxoid production within the transgenic organism.

Another aspect of the invention provides the nucleic acid sequences shown in SEQ ID NOs: 1, 3, 5, 7, 9, 11, 13, 15, 17, 19, 21, and 23 and the corresponding amino acid sequences shown in SEQ ID NOs: 2, 4, 6, 8, 10, 12, 14, 16, 18, 20, 22, and 24, respectively, as well as fragments of the nucleic acid and the amino acid sequences. These sequences are useful for isolating the nucleic acid and amino acid sequences corresponding to full-length transacylases. These amino acid sequences and nucleic acid sequences are also useful for creating specific binding agents that recognize the corresponding transacylases.

Accordingly, another aspect of the invention provides for the identification of transacylases and fragments of transacylases that have amino acid and nucleic acid sequences that vary from the disclosed sequences. For example, the invention provides transacylase amino acid sequences that vary by one or more conservative amino acid substitutions, or that share at least 50% sequence identity with the amino acid sequences provided while maintaining transacylase activity.

The nucleic acid sequences encoding the transacylases and fragments of the transacylases can be cloned, using standard molecular biology techniques, into vectors. These vectors can then be used to transform host cells. Thus, a host cell can be modified to express either increased levels of transacylase or decreased levels of transacylase.

Another aspect of the invention provides methods for isolating nucleic acid sequences encoding full-length transacylases. The methods involve hybridizing at least ten contiguous nucleotides of any of the nucleic acid sequences shown in SEQ ID NOs: 1, 3, 5, 7, 9, 11, 13, 15, 17, 19, 21, 23, 25, 27, 44, 49, 51, 53, 55, and 57 to a second nucleic acid sequence, wherein the second nucleic acid sequence encodes a transacylase. This method can be practiced in the context of, for example, Northern blots, Southern blots, and the polymerase chain reaction (PCR). Hence, the invention also provides the transacylases identified by this method.

Yet another aspect of the invention involves methods of adding at least one acyl group to at least one taxoid. These methods can be practiced in vivo or in vitro, and can be used to add acyl groups to various intermediates in the paclitaxel biosynthetic pathway, and to add acyl groups to related taxoids that are not necessarily in a paclitaxel biosynthetic pathway.

SEQUENCE LISTINGS

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 is the nucleotide sequence of Probe 1.
SEQ ID NO: 2 is the deduced amino acid sequence of Probe 1.
SEQ ID NO: 3 is the nucleotide sequence of Probe 2.
SEQ ID NO: 4 is the deduced amino acid sequence of Probe 2.
SEQ ID NO: 5 is the nucleotide sequence of Probe 3.
SEQ ID NO: 6 is the deduced amino acid sequence of Probe 3.
SEQ ID NO: 7 is the nucleotide sequence of Probe 4.
SEQ ID NO: 8 is the deduced amino acid sequence of Probe 4.
SEQ ID NO: 9 is the nucleotide sequence of Probe 5.
SEQ ID NO: 10 is the deduced amino acid sequence of Probe 5.
SEQ ID NO: 11 is the nucleotide sequence of Probe 6.
SEQ ID NO: 12 is the deduced amino acid sequence of Probe 6.
SEQ ID NO: 13 is the nucleotide sequence of Probe 7.
SEQ ID NO: 14 is the deduced amino acid sequence of Probe 7.
SEQ ID NO: 15 is the nucleotide sequence of Probe 8.
SEQ ID NO: 16 is the deduced amino acid sequence of Probe 8.
SEQ ID NO: 17 is the nucleotide sequence of Probe 9.
SEQ ID NO: 18 is the deduced amino acid sequence of Probe 9.
SEQ ID NO: 19 is the nucleotide sequence of Probe 10.
SEQ ID NO: 20 is the deduced amino acid sequence of Probe 10.
SEQ ID NO: 21 is the nucleotide sequence of Probe 11.
SEQ ID NO: 22 is the deduced amino acid sequence of Probe 11.
SEQ ID NO: 23 is the nucleotide sequence of Probe 12.
SEQ ID NO: 24 is the deduced amino acid sequence of Probe 12.
SEQ ID NO: 25 is the nucleotide sequence of the full-length acyltransacylase clone TAX2 (also referred to herein as "TAX02").
SEQ ID NO: 26 is the deduced amino acid sequence of the full-length acyltransacylase clone TAX2.
SEQ ID NO: 27 is the nucleotide sequence of the full-length acyltransacylase clone TAX1 (also referred to herein as "TAX01").
SEQ ID NO: 28 is the deduced amino acid sequence of the full-length acyltransacylase clone TAX1.
SEQ ID NO: 29 is the amino acid sequence of a transacylase peptide fragment.
SEQ ID NO: 30 is the amino acid sequence of a transacylase peptide fragment.
SEQ ID NO: 31 is the amino acid sequence of a transacylase peptide fragment.
SEQ ID NO: 32 is the amino acid sequence of a transacylase peptide fragment.
SEQ ID NO: 33 is the amino acid sequence of a transacylase peptide fragment.
SEQ ID NO: 34 is the AT-FOR1 PCR primer.
SEQ ID NO: 35 is the AT-FOR2 PCR primer.

SEQ ID NO: 36 is the AT-FOR3 PCR primer.

SEQ ID NO: 37 is the AT-FOR4 PCR primer.

SEQ ID NO: 38 is the AT-REV1 PCR primer.

SEQ ID NO: 39 is an amino acid sequence variant that allowed for the design of the AT-FOR3 PCR primer.

SEQ ID NO: 40 is an amino acid sequence variant that allowed for the design of the AT-FOR4 PCR primer.

SEQ ID NO: 41 is a consensus amino acid sequence that allowed for the design of the AT-REV1 PCR primer.

SEQ ID NO: 42 is a PCR primer, useful for identifying transacylases.

SEQ ID NO: 43 is a PCR primer, useful for identifying transacylases.

SEQ ID NO: 44 is the nucleotide sequence of the full-length acyltransacylase clone TAX6 (also referred to herein as "TAX06").

SEQ ID NO: 45 is the deduced amino acid sequence of the full-length acyltransacylase clone TAX6.

SEQ ID NO: 46 is a PCR primer, useful for identifying TAX6.

SEQ ID NO: 47 is a PCR primer, useful for identifying TAX6.

SEQ ID NO: 48 is a 6-amino acid motif commonly found in transacylases.

SEQ ID NO: 49 is the nucleotide sequence of the full-length acyltransacylase clone TAX5 (also referred to herein as "TAX05").

SEQ ID NO: 50 is the deduced amino acid sequence of the full-length acyltransacylase clone TAX5.

SEQ ID NO: 51 is the nucleotide sequence of the full-length acyltransacylase clone TAX7 (also referred to herein as "TAX07").

SEQ ID NO: 52 is the deduced amino acid sequence of the full-length acyltransacylase clone TAX7.

SEQ ID NO: 53 is the nucleotide sequence of the full-length acyltransacylase clone TAX10.

SEQ ID NO: 54 is the deduced amino acid sequence of the full-length acyltransacylase clone TAX10.

SEQ ID NO: 55 is the nucleotide sequence of the full-length acyltransacylase clone TAX12.

SEQ ID NO: 56 is the deduced amino acid sequence of the full-length acyltransacylase clone TAX 12.

SEQ ID NO: 57 is the nucleotide sequence of the full-length acyltransacylase clone TAX13.

SEQ ID NO: 58 is the deduced amino acid sequence of the full-length acyltransacylase clone TAX13.

SEQ ID NO: 59 is the nucleotide sequence of the full-length acyltransacylase clone TAX9 (also referred to herein as "TAX09").

SEQ ID NO: 60 is the deduced amino acid sequence of the full-length acyltransacylase clone TAX9.

Figure 6D:
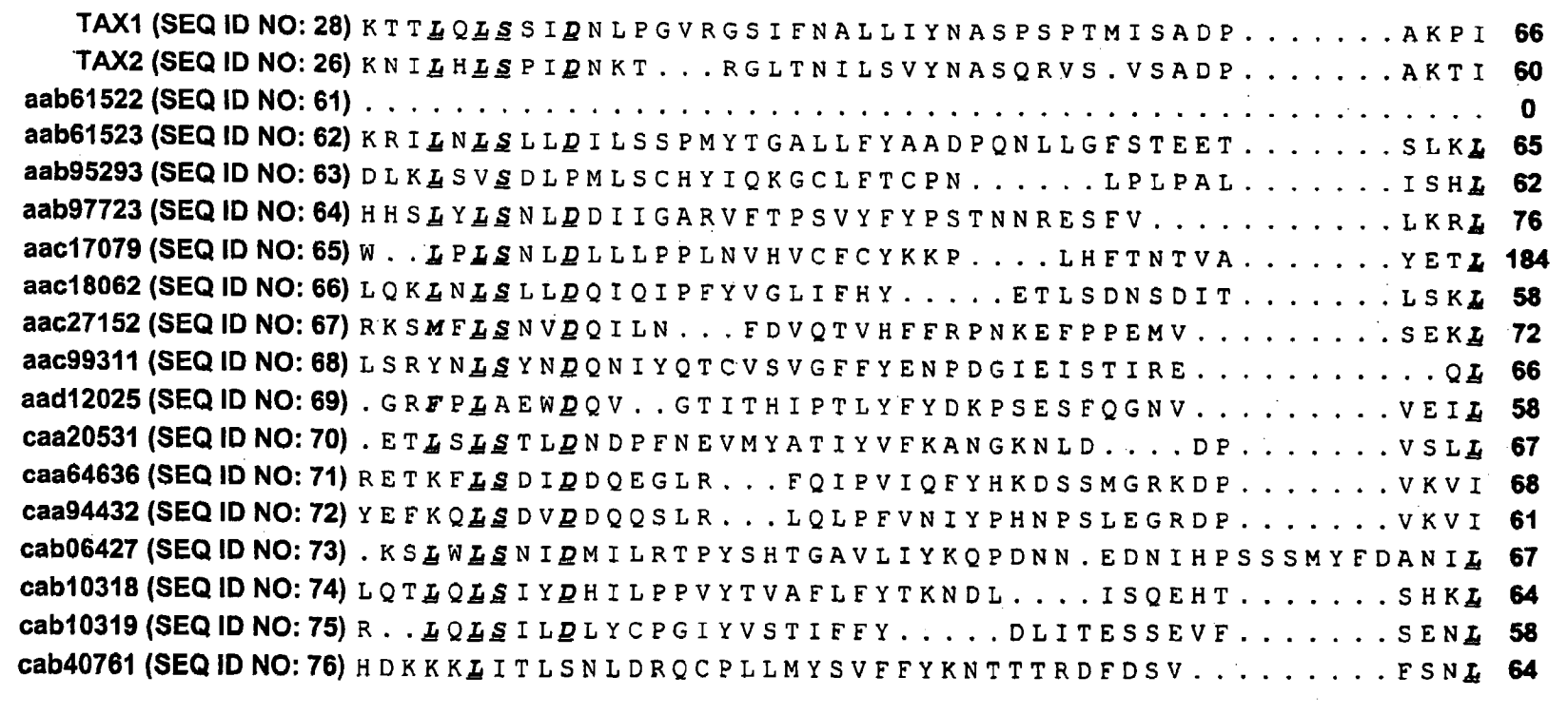
Figure 6L:
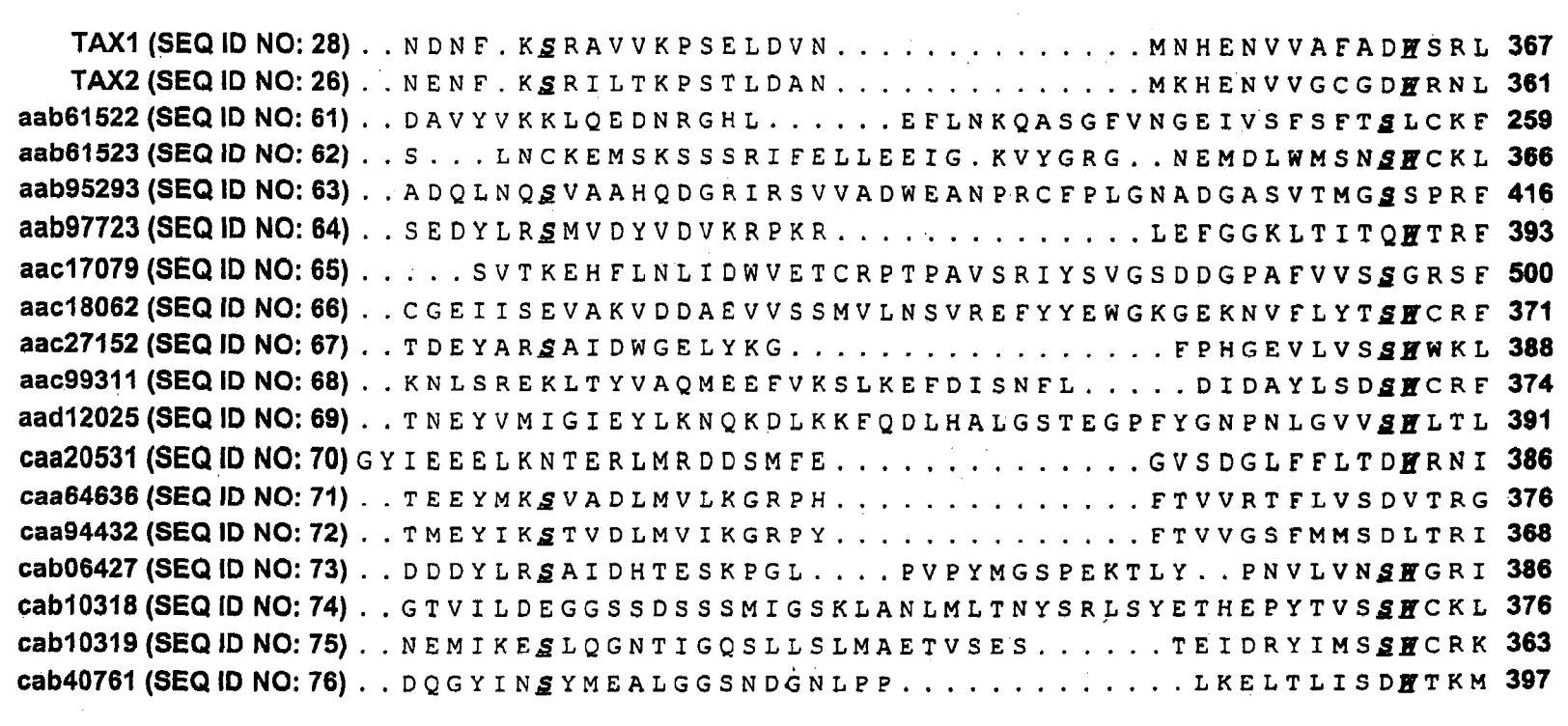

SEQ ID NO: 61–76 are the amino acid sequences shown in FIG. 6.

FIGURES

FIG. 1 shows an outline of the paclitaxel biosynthetic pathway. The cyclization of geranylgeranyl diphosphate to taxadiene by taxadiene synthase and the hydroxylation to taxadien-5α-ol by taxadiene 5α-hydroxylase (a), the acetylation of taxadien-5α-ol by taxa-4(20),11(12)-dien-5α-ol-O-acetyl transferase (gene product of TAX1) (b), the conversion of a 2-debenzoyl "taxoid-type" intermediate to 10-deacetylbaccatin III by a taxane-2α-O-benzoyl transferase (gene product of TAX2; SEQ ID NO: 25) (c), the conversion of 10-deacetylbaccatin III to baccatin III by 10-deacetylbaccatin III-10-O-acetyl transferase (gene product of TAX6) (d), and the side chain attachment to baccatin III to form paclitaxel (e) are illustrated. The broken arrow indicates several as yet undefined steps.

FIG. 2 shows the peptide sequences generated by endolysc and trypsin proteolysis of purified taxadienol acetyl transacylase.

Figure 3A:
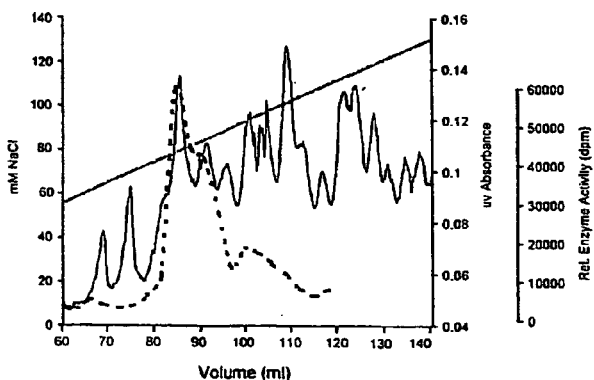
Figure 3B:
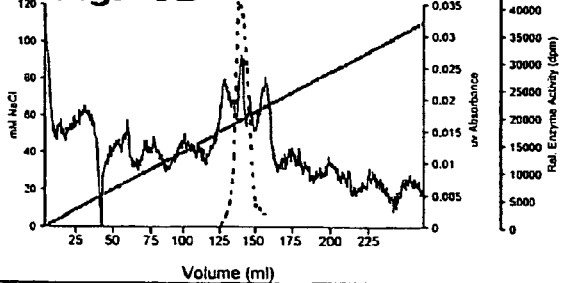
Figure 3C:
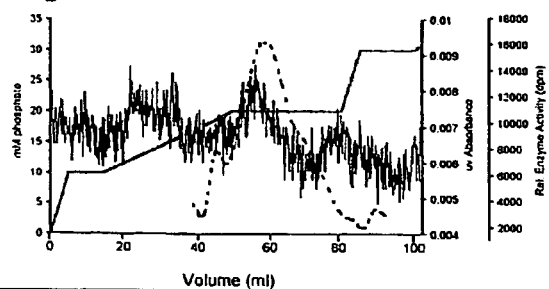
Figure 3D:
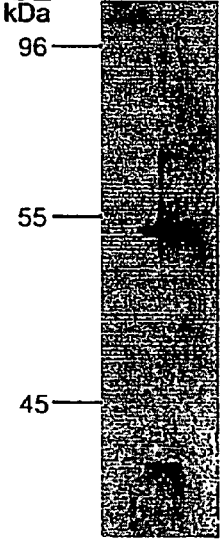

FIGS. 3A–3D include elution profiles from several different columns. FIG. 3A is an elution profile of the acetyl transacylase on Source HR 15Q (10×100 mm) preparative scale anion-exchange chromatography; FIG. 3B is an elution profile on analytical scale Source HR 15Q (5×50 mm) column chromatography; and FIG. 3C is an elution profile on the ceramic hydroxyapatite column. The solid line is the UV absorbance at 280 nm; the dotted line is the relative transacetylase activity (dpm); and the hatched line is the elution gradient (sodium chloride or sodium phosphate). FIG. 3D is a photograph of a silver-stained 12% SDS-PAGE showing the purity of taxadien-5α-ol acetyl transacylase (50 kDa) after hydroxyapatite chromatography. A minor contaminant is present at ~35 kDa.

FIG. 4 shows four forward (AT-FOR1, AT-FOR2, AT-FOR3, AT-FOR4) and one reverse (AT-REV 1) degenerate primers that were used to amplify an induced *Taxus* cell library cDNA from which twelve hybridization probes were obtained. Inosine positions are indicated by "I". Each of the forward primers was paired with the reverse primer in separate PCR reactions. Primers AT-FOR1 (SEQ ID NO: 34) and AT-FOR2 (SEQ ID NO: 35) were designed from the tryptic fragment SEQ ID NO: 30; the remaining primers were derived by database searching based on SEQ ID NO: 30.

Figures 5A, 5B, 5C, 5D, 5E, 5F, 5G:
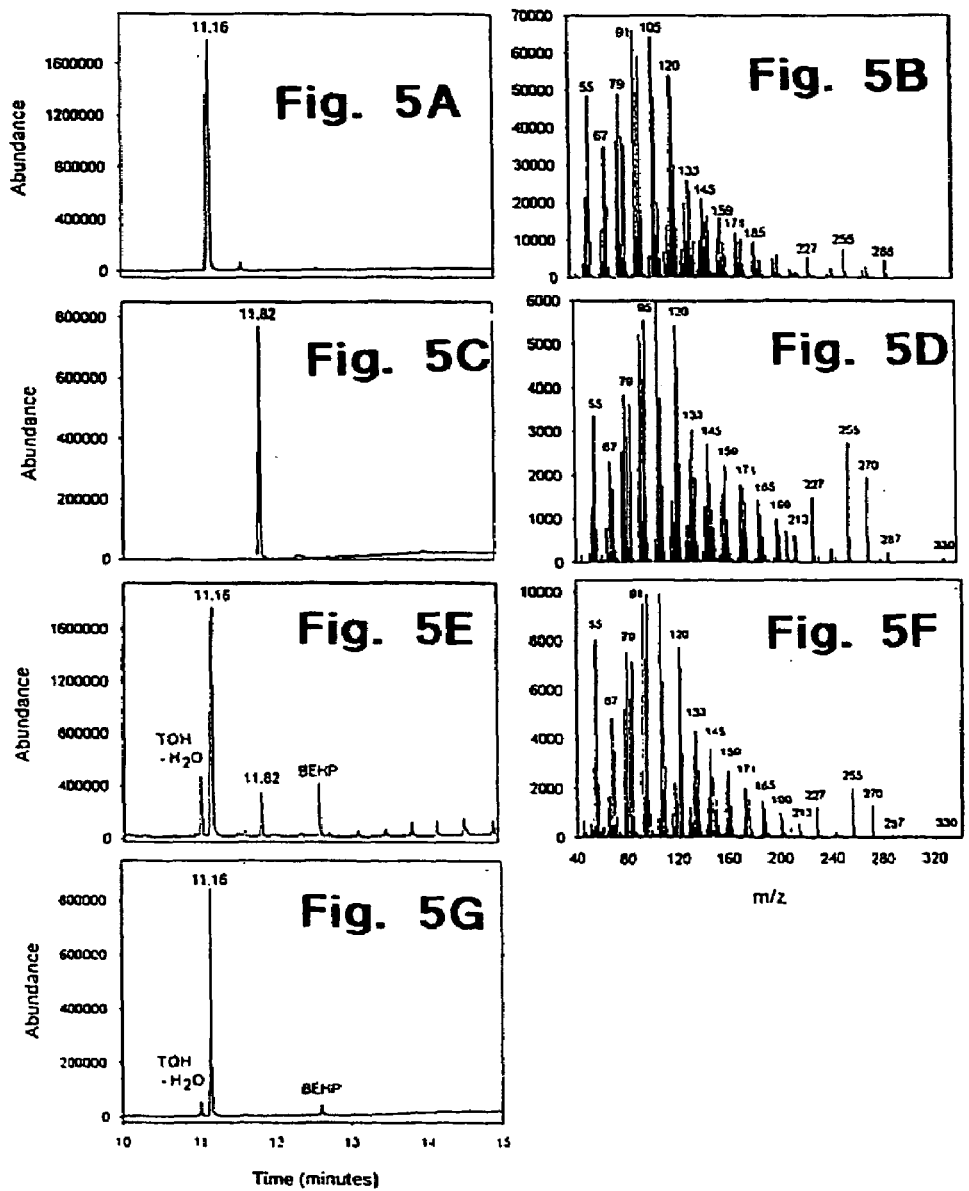

FIGS. 5A–5G shows data obtained from a coupled gas chromatographic-mass spectrometric (GC-MS) analysis of the biosynthetic taxadien-5α-yl acetate formed during the incubation of taxadien-5α-ol with soluble enzyme extracts from isopropyl β-D-thiogalactoside (IPTG)-induced *E. coli* JM109 cells transformed with full-length acyltransacylase clones TAX1 (SEQ ID NO: 28) and TAX2 (SEQ ID NO: 25). FIGS. 5A and 5B show the respective GC and MS profiles of authentic taxadien-5α-ol; FIGS. 5C and 5D show the respective GC and MS profiles of authentic taxadien-5α-yl acetate; FIG. 5E shows the GC profile of taxadien-5α-ol (11.16 minutes), taxadien-5α-yl acetate (11.82 minutes), dehydrated taxadien-5α-ol ("TOH—H$_2$O" peak), and a contaminant, bis-(2-ethylhexyl)phthlate ("BEHP" peak, a plasticizer, CAS 117-81-7, extracted from buffer) after incubation of taxadien-5α-ol and acetyl coenzyme A with the soluble enzyme fraction derived from *E. coli* JM109 transformed with the full-length clone TAX1 (SEQ ID NO: 27). Panel F shows the mass spectrum of biosynthetically formed taxadien-5α-yl acetate by the recombinant enzyme (11.82 minute peak in GC profile FIG. 5E); FIG. 5G shows the GC profile of the products generated from taxadien-5α-ol and acetyl coenzyme A by incubation with the soluble enzyme fraction derived from *E. coli* JM 109 cells transformed with the full-length clone TAX2 (note the absence of taxadien-5α-yl acetate indicating that this clone is inactive in the transacylase reaction).

FIGS. 6A–6N show a pileup of deduced amino acid sequences listed in Table 1, and of TAX1 (SEQ ID NO: 28) and TAX2 (SEQ ID NO: 25). Residues underlined in bold italics (and bold italics) indicate the few regions of conservation. Forward arrow (left to right) shows conserved region from which degenerate forward PCR primers were designed. Reverse arrow (right to left) shows region from which the reverse PCR primer was designed (cf., FIG. 4).

Figure 7:
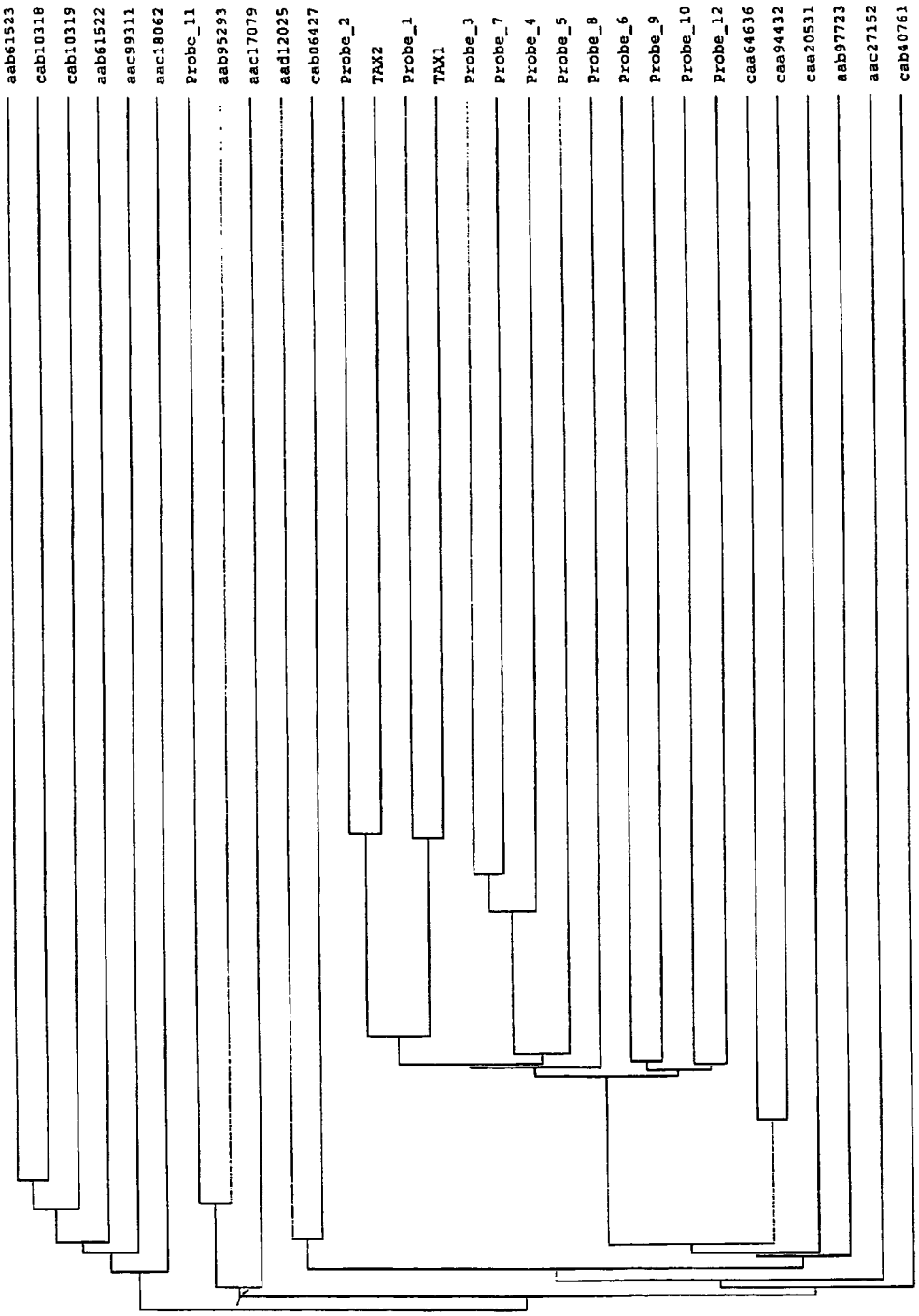

FIG. 7 shows a dendrogram of the deduced peptide sequence relationships between *Taxus* transacylase sequences (Probes 1–12, TAX1 (SEQ ID NO: 28), and TAX2) and closest relative sequences of defined and unknown function obtained from the GENBANK™ database described in Table 1.

Figure 8:
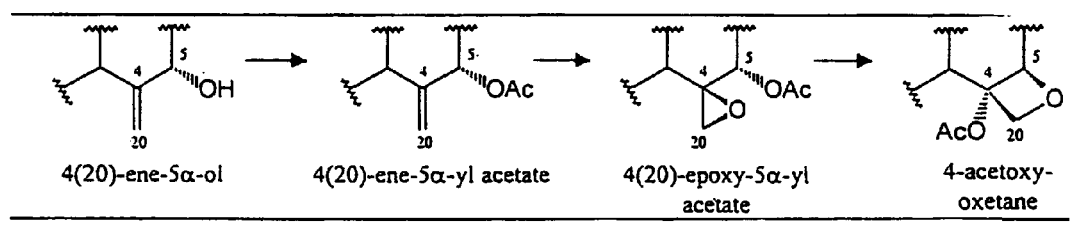

FIG. 8 shows a postulated biosynthetic scheme for the formation of the oxetane, present in paclitaxel and related late-stage taxoids, in which the 4(20)-ene-5α-ol is converted to the 4(20)-ene-5α-yl acetate followed by epoxidation to the 4(20)-epoxy-5α-acetoxy group and then intramolecular rearrangement to the 4-acetoxy oxetane moiety.

Figures 9A, 9B:
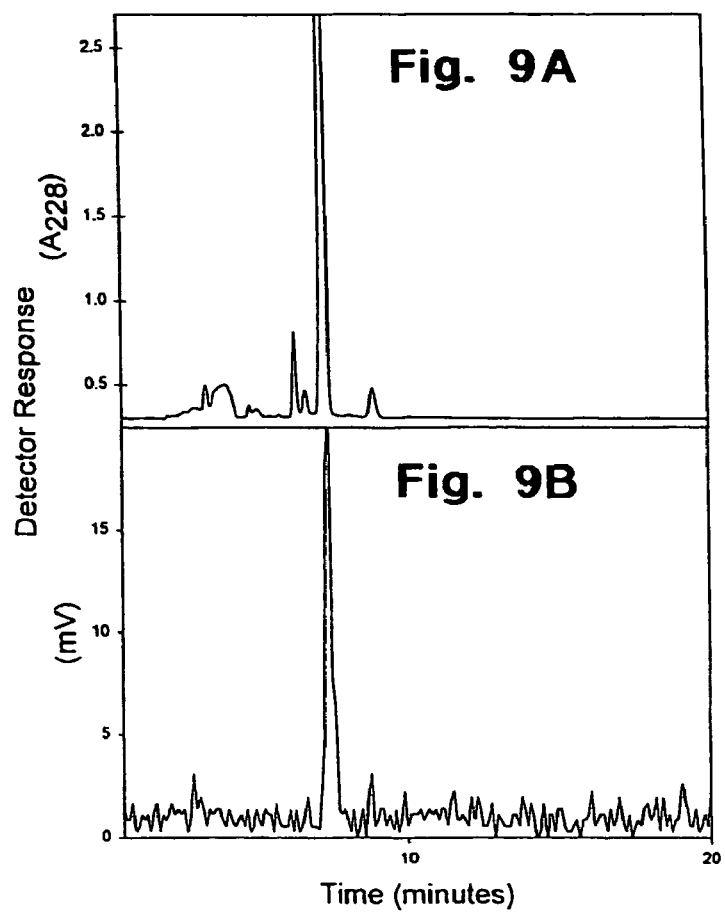

FIGS. 9A and 9B show radio-HPLC (high-performance liquid chromatography) analysis of the biosynthetic product (Rt=7.0±0.1 minutes) generated from 10-deacetylbaccatin III and [2-$^3$H]acetyl CoA by the recombinant acetyl transferase (gen product of TAX6 (SEQ ID NO: 45)). FIG. 9A shows the UV profile and FIG. 9B shows the coincident radioactivity profile, both of which coincide with the retention time of authentic baccatin III. For the enzyme preparation, *E. coli* cells transformed with the pCWori+ vector harboring the putative DBAT gene were grown overnight at 37° C. in 5 mL Luria-Bertani medium supplemented with ampicillin, and 1 mL of this inoculum was added to and grown in 100 mL Terrific Broth culture medium (6 g bacto-tryptone, Difco Laboratories, Spark, Md., 12 g yeast extract, EM Science, Cherryhill, N.J., and 2 mL gycerol in 500 mL water) supplemented with 1 mM IPTG, 1 mM thiamine HCl and 50 µg ampicillin/mL. After 24 hours, the bacteria were harvested by centrifugation, resuspended in 20 mL of assay buffer (25 mM Mopso, pH 7.4) and then disrupted by sonication at 0–4° C. The resulting homogenate was centrifuged at 15,000 g to remove debris, and a 1 mL aliquot of the supernatant was incubated with 10-deacetyl-baccatin III (400 µM) and [2-$^3$H]acetyl coenzyme A (0.45µCi, 400 µM) for 1 hour at 31° C. The reaction mixture was extracted with ether and the solvent concentrated in vacuo. The crude product (pooled from five such assays) was purified by silica gel thin-layer chromatography (TLC; 70:30 ethyl acetate:hexane). The band co-migrating with authentic baccatin III (Rf=0.45 for the standard) was isolated and analyzed by radio-HPLC to reveal the new radioactive product described above. Extracts of *E. coli* transformed with empty vector controls did not yield detectable product when assayed by identical methods.

Figures 10A, 10B:
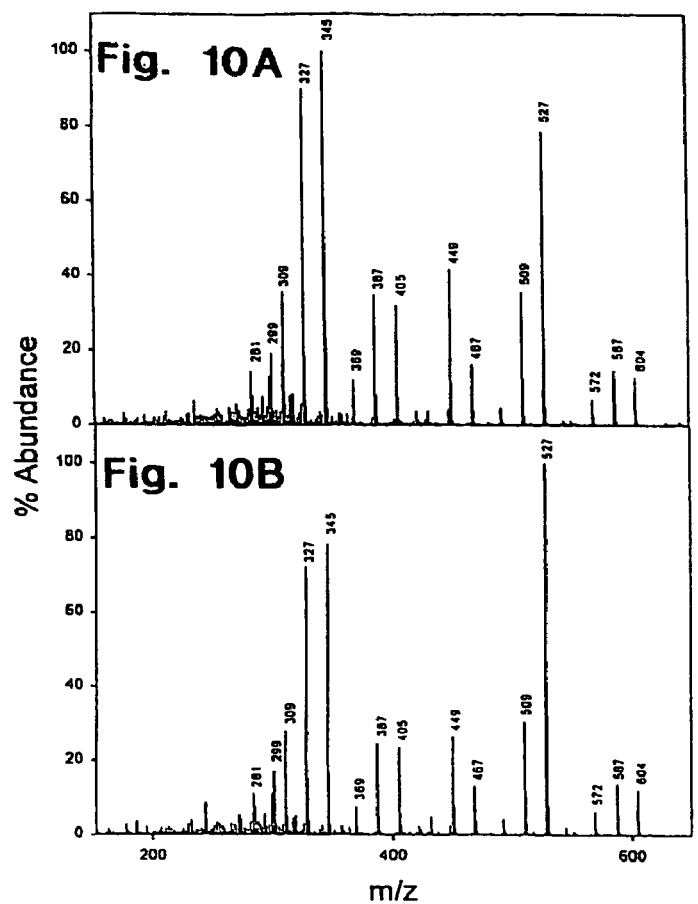

FIGS. 10A and 10B show the results from a combined reverse-phase HPLC-atmospheric pressue chemical ionization MS (mass spectrometry) analysis of (FIG. 10A) the biosynthetic product (Rt=8.6±0.1 minutes) generated by recombinant acetyl transferase with 10-deaceylbaccatin III and acetyl CoA as co-substrates, and of (FIG. 10B) authentic baccatin III (Rt=8.6±0.1 minutes). The diagnostic mass spectral fragments are at m/z 605 (M+NH$_4^+$), 587 (MH$^+$), 572 (MH$^+$—CH$_3$), 527 (MH$^+$—CH$_3$COOH), and 509 (MH$^+$—(CH$_3$COOH+H$_2$O)). For preparation of recombinant enzyme and product isolation, see FIGS. 9A and 9B legend.

Figure 11:
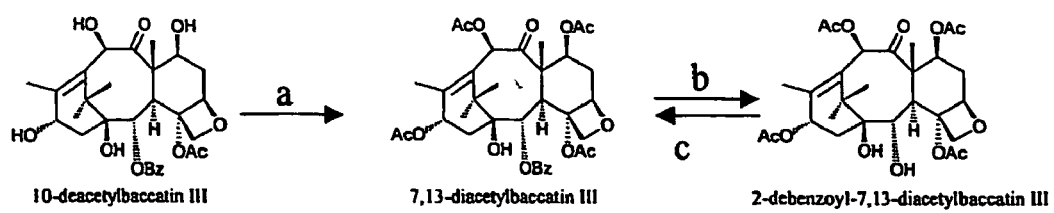

FIG. 11 shows an outline of the synthesis and utilization of 2-debenzoyl-7,13-diacetylbaccatin III: methylene chloride, acetic anhydride, 4-(N,N'-dimethylamino)pyridine, triethylamine, 25° C., 18 h (a), tetrahydrofuran, Red-Al (65+% in toluene), 0° C., 30 minutes (b), and the reaction catalyzed by taxane-2α-O-benzoyl transferase in the presence of benzoyl coenzyme A (c).

Figures 12A, 12B:
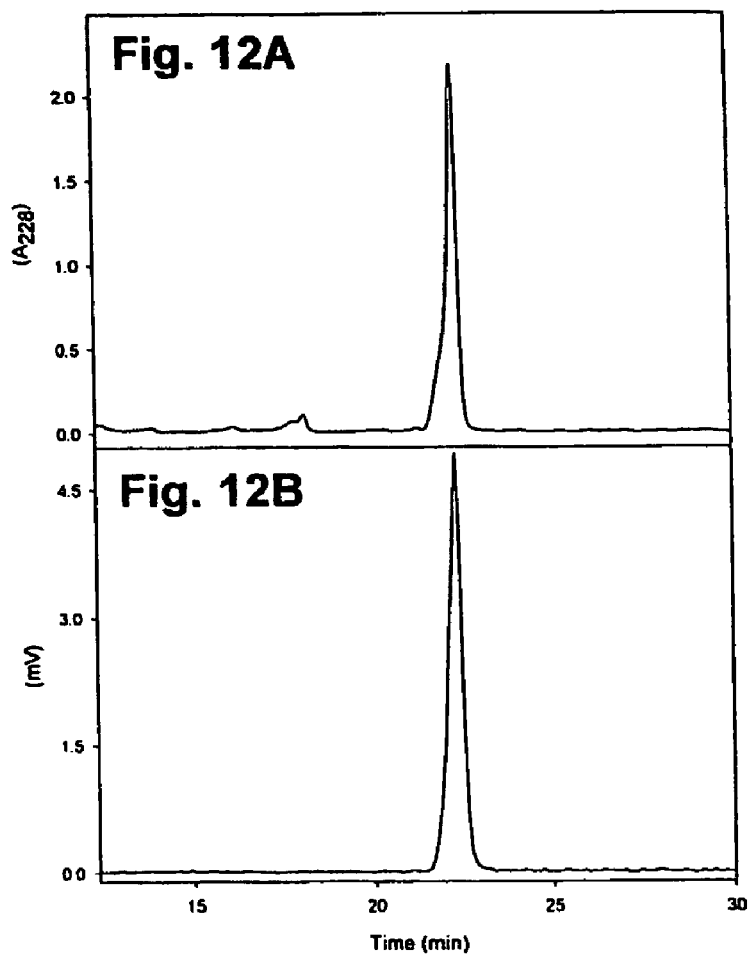

FIGS. 12A and 12B show radio-HPLC analysis of the biosynthetic product (Rt=21.9 ±0.1 minute) generated from 2-debenzoyl-7,13-diacetylbaccatin III and [7-$^{14}$C]benzoyl CoA by the recombinant TAX2 benzoyl transferase (SEQ ID NO: 25). FIG. 12A shows the coincident UV profile (A$_{228}$) and FIG. 12B shows the radioactivity profile (in mV), both of which coincide exactly with the retention time of authentic 7,13-diacetylbaccatin III. Extracts of control *E. coli* transformed with empty vector did not yield detectable product when assayed by identical methods.

Figures 13A, 13B:
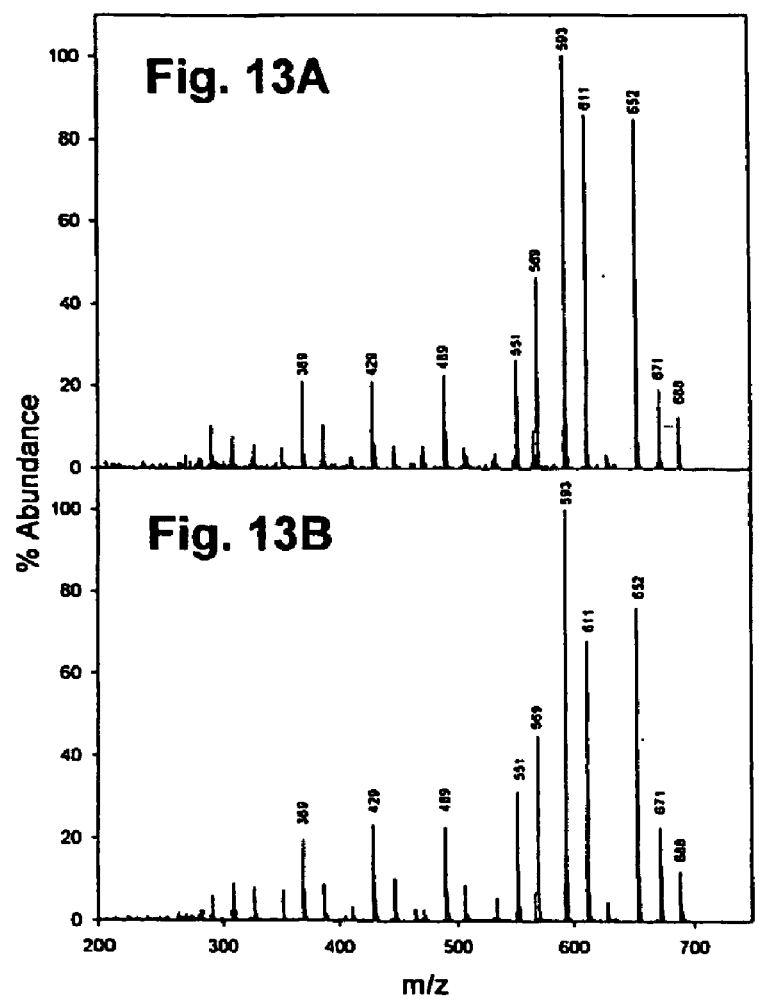

FIGS. 13A and 13B show the results from a coupled reverse-phase HPLC-atmospheric pressure chemical ionization MS analysis of (FIG. 13A) the biosynthetic product (Rt=43.6±0.1 minute) generated by the TAX2 (SEQ ID NO: 25) recombinant benzoyl transferase with 2-debenzoyl-7,13-diaceylbaccatin III and benzoyl CoA as co-substrates, and of (FIG. 13B) authentic 7,13-diacetylbaccatin III (Rt=43.6±0.1 minute). The diagnostic ions are at m/z 688 (P+NH$_4^+$), 671 (PH$^+$), 652 (P$^+$—H$_2$O), 611 (PH$^+$—CH$_3$COOH), 593 (m/z 652-CH$_3$COO), 551 (m/z 611-CH$_3$COOH), and 489 (m/z 611-PhCOOH).

Figure 14:
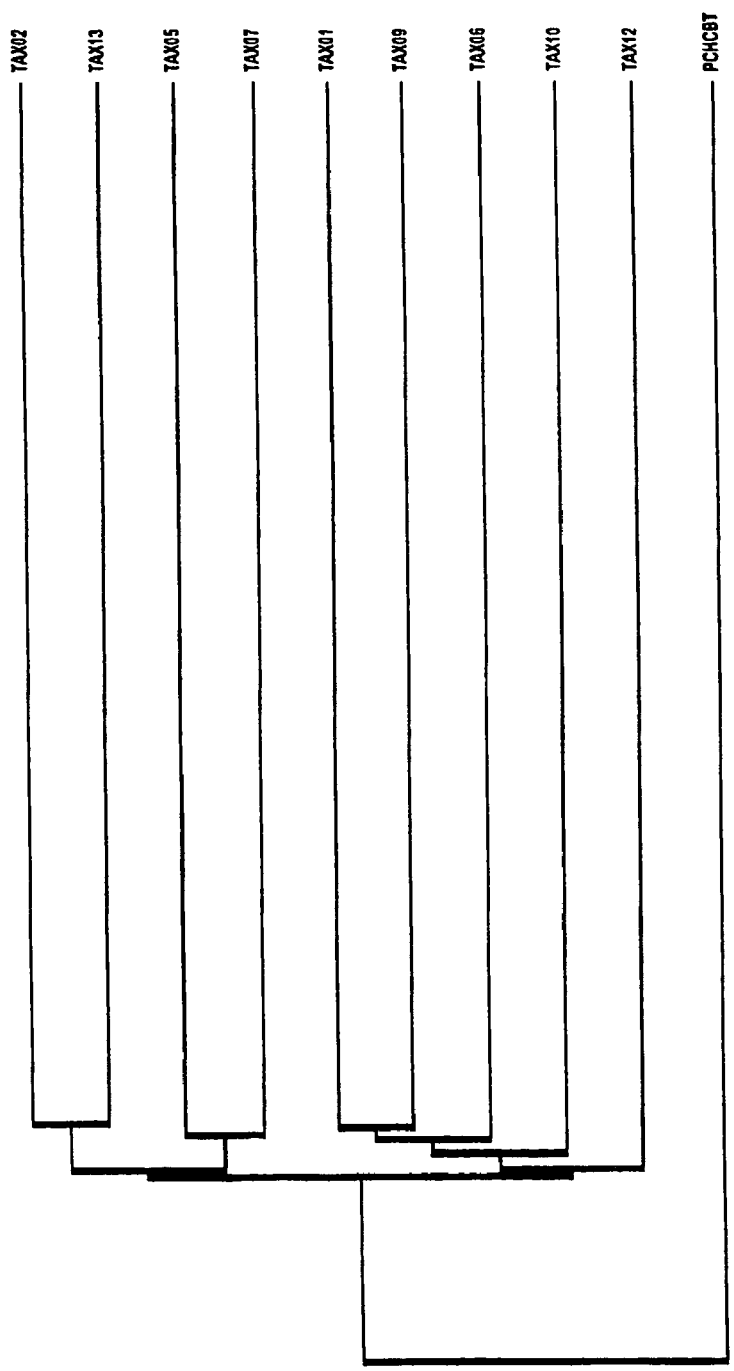

FIG. 14 shows a dendrogram of the pairwise relationship among the deduced amino acid sequences of isolated, full-length *T. cuspidata* acyl transferases designated TAX01, TAX02, TAX05, TAX06, TAX07, TAX09, TAX10, TAX12, TAX 13, (SEQ ID NOS: 28, 26, 50, 45, 52, 60, 54, 56, and 58, respectively) and of PCHCBT (designating the anthranilate hydroxycinnamoyl/benzoyl transferase of *Dianthus* (protein identification number [PID] cab06427 and GENBANK™ accession no. Z84383 located in the ENTREZ™ databank)). Distance along the vertical axis is proportional to the difference between sequences; distance along the horizontal axis has no significance.

Figure 15A:
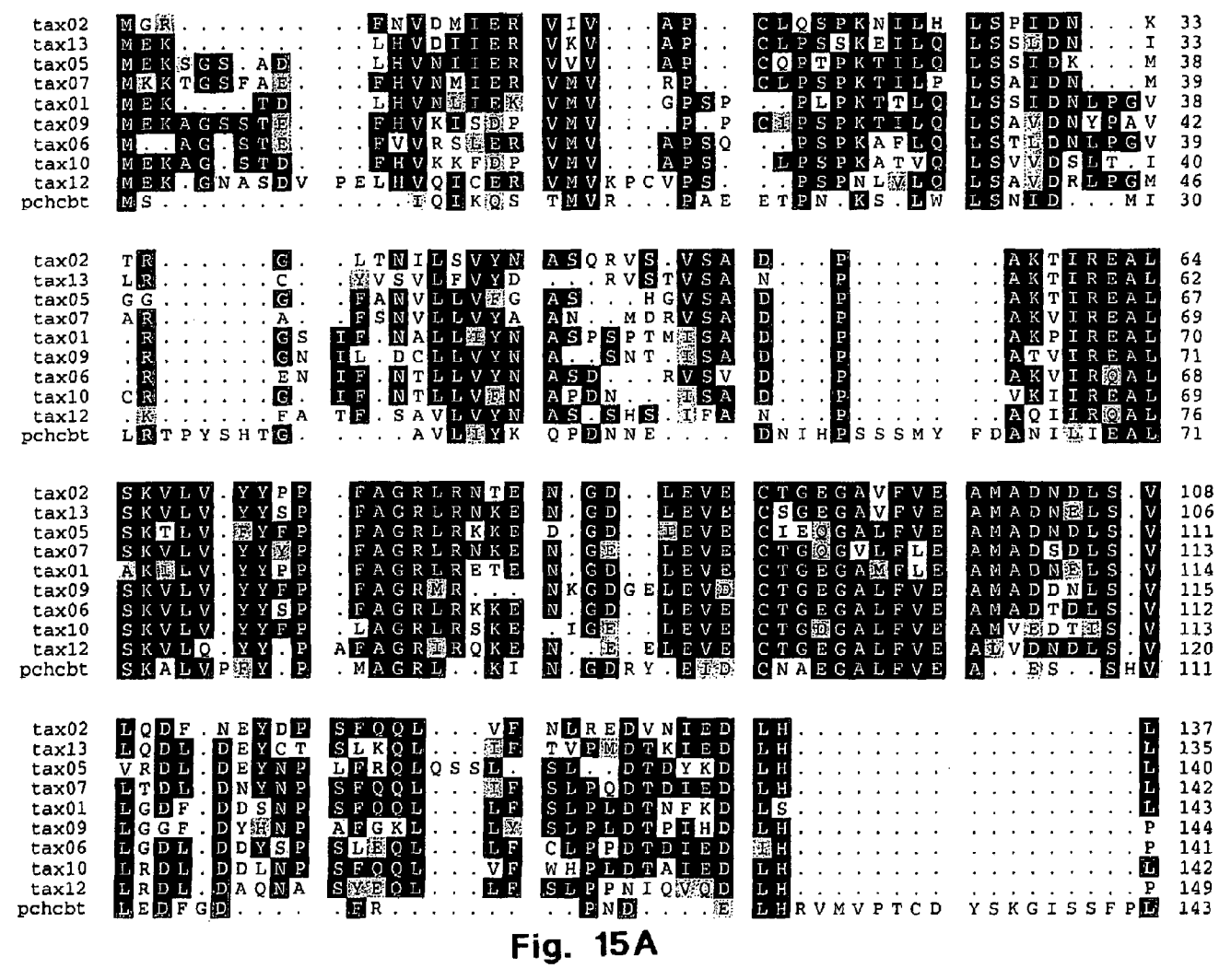
Figure 15B:
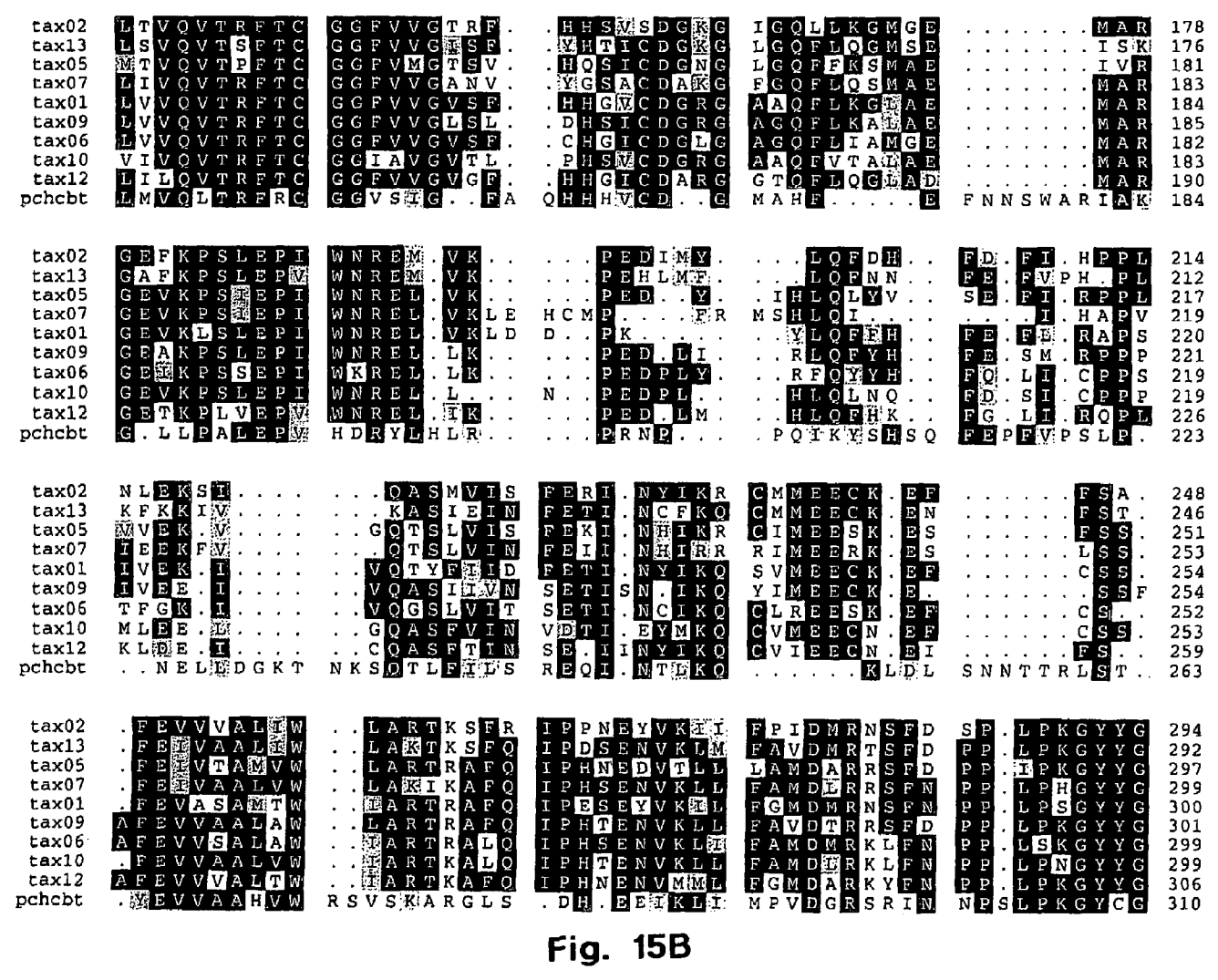
Figure 15C:
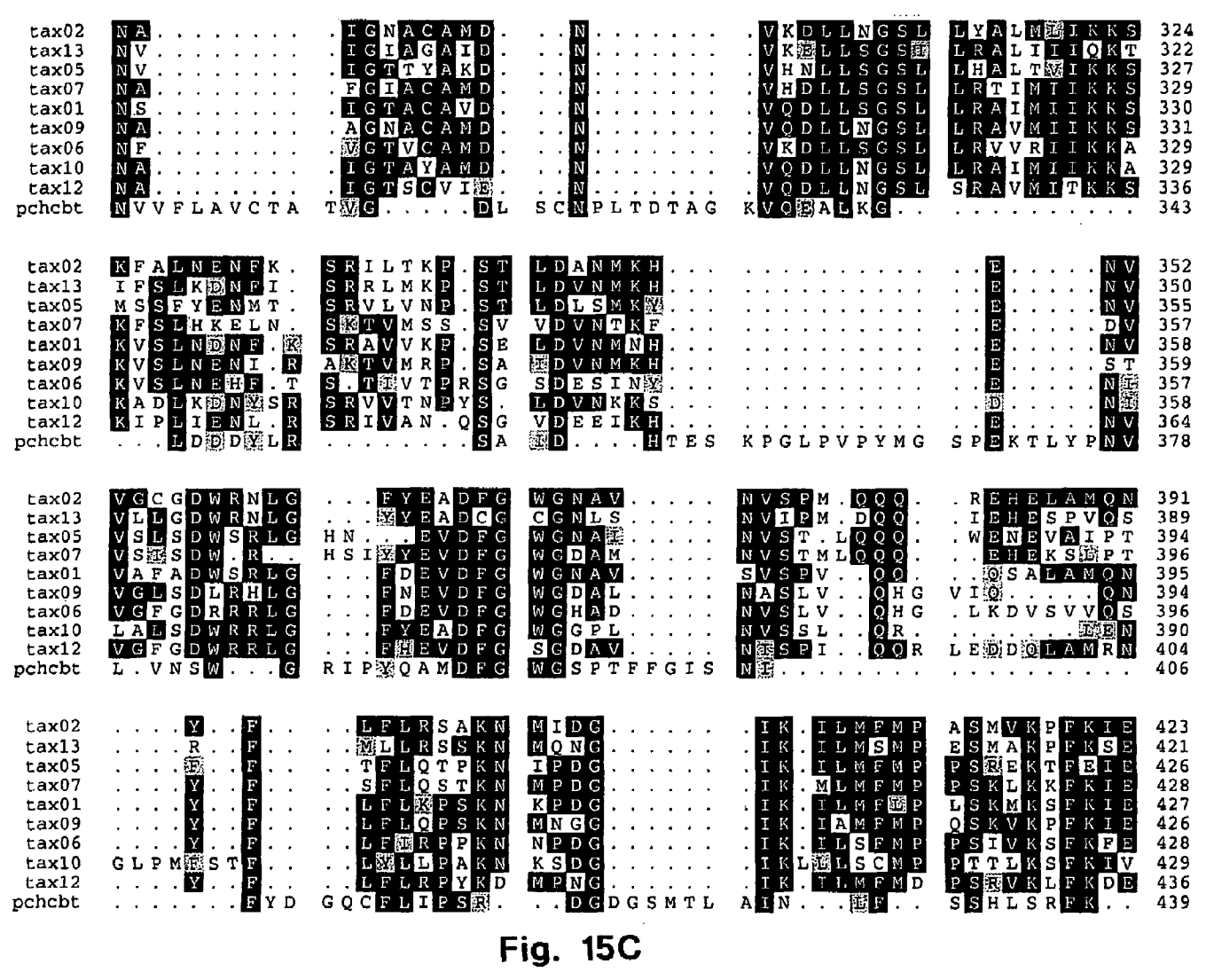
Figure 15D:
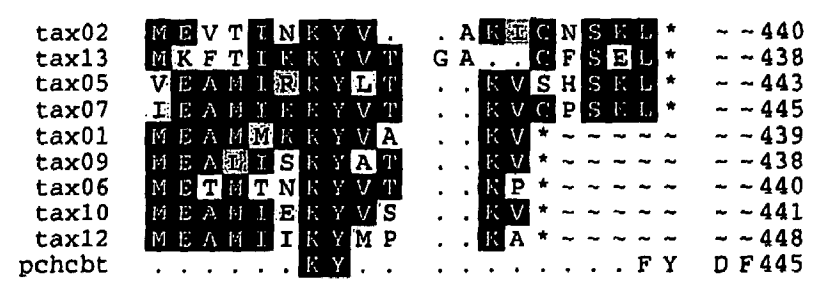

FIGS. 15A–15D show the deduced amino acid sequence comparison of six transacylases (TAX05, TAX07, TAX09, TAX10, TAX12, and TAX13) as well as TAX01 (taxadien-5α-ol acetyl transferase, accession no. AF190130), TAX02 (taxane-2α-O-benzoyl transferase, accession no. AF297618), TAX06 (10-deacetylbaccatin III-0-O-acetyl transferase, accession no. AF193765) and PCHCBT (anthranilate hydroxycinnamoyl/benzoyl transferase, accession no. Z84383). Residues underlined in bold italics indicate positional identity for at least three of the compared sequences; similar amino acids are indicated by bold italics. The alignment was created with the PileUp program (Wisconsin Package Version 10; Genetics Computer Group, Madison, Wis.).

DETAILED DESCRIPTION

I. Definitions

Mammal: This term includes both humans and non-human mammals. Similarly, the term "patient" includes both humans and veterinary subjects.

Taxoid: A "taxoid" is a chemical based on the Taxane ring structure as described in Kinston et al., *Progress in the Chemistry of Organic Natural Products*, Springer-Verlag, 1993.

Isolated: An "isolated" biological component (such as a nucleic acid or protein or organelle) is a component that has been substantially separated or purified away from other biological components in the cell of the organism in which the component naturally occurs, i.e., other chromosomal and extra-chromosomal DNA, RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Orthologs: An "ortholog" is a gene that encodes a protein that displays a function that is similar to a gene derived from a different species.

Homologs: "Homologs" are two nucleotide sequences that share a common ancestral sequence and diverged when a species carrying that ancestral sequence split into two species.

Purified: The term "purified" does not require absolute purity; rather, it is intended as a relative term. Thus, for example, a purified enzyme or nucleic acid preparation is one in which the subject protein or nucleotide, respectively, is at a higher concentration than the protein or nucleotide would be in its natural environment within an organism. For example, a preparation of an enzyme can be considered as purified if the enzyme content in the preparation represents at least 50% of the total protein content of the preparation.

Vector: A "vector" is a nucleic acid molecule as introduced into a host cell, thereby producing a transformed host cell. A vector may include nucleic acid sequences, such as an origin of replication, that permit the vector to replicate in a host cell. A vector may also include one or more screenable markers, selectable markers, or reporter genes and other genetic elements known in the art.

Transformed: A "transformed" cell is a cell into which a nucleic acid molecule has been introduced by molecular biology techniques. As used herein, the term "transformation" encompasses all techniques by which a nucleic acid molecule might be introduced into such a cell, including transfection with a viral vector, transformation with a plasmid vector, and introduction of naked DNA by electroporation, lipofection, and particle gun acceleration.

DNA construct: The term "DNA construct" is intended to indicate any nucleic acid molecule of cDNA, genomic DNA, synthetic DNA, or RNA origin. The term "construct" is intended to indicate a nucleic acid segment that may be single- or double-stranded, and that may be based on a complete or partial naturally occurring nucleotide sequence encoding one or more of the transacylase genes of the present invention. It is understood that such nucleotide sequences include intentionally manipulated nucleotide sequences, e.g., subjected to site-directed mutagenesis, and sequences that are degenerate as a result of the genetic code. All degenerate nucleotide sequences are included within the scope of the invention so long as the transacylase encoded by the nucleotide sequence maintains transacylase activity as described below.

Recombinant: A "recombinant" nucleic acid is one having a sequence that is not naturally occurring in the organism in which it is expressed, or has a sequence made by an artificial combination of two otherwise-separated, shorter sequences. This artificial combination is often accomplished by chemical synthesis or, more commonly, by the artificial manipulation of isolated segments of nucleic acids, e.g., by genetic engineering techniques. "Recombinant" is also used to describe nucleic acid molecules that have been artificially manipulated, but contain the same control sequences and coding regions that are found in the organism from which the gene was isolated.

Specific binding agent: A "specific binding agent" is an agent that is capable of specifically binding to the transacylases of the present invention, and may include polyclonal antibodies, monoclonal antibodies (including humanized monoclonal antibodies) and fragments of monoclonal antibodies such as Fab, F(ab')2 and Fv fragments, as well as any other agent capable of specifically binding to the epitopes on the proteins.

cDNA (complementary DNA): A "cDNA" is a piece of DNA lacking internal, non-coding segments (introns) and regulatory sequences that determine transcription. cDNA is synthesized in the laboratory by reverse transcription from messenger RNA extracted from cells.

ORF (open reading frame): An "ORF" is a series of nucleotide triplets (codons) coding for amino acids without any termination codons. These sequences are usually translatable into respective polypeptides.

Operably linked: A first nucleic acid sequence is "operably linked" with a second nucleic acid sequence whenever the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Probes and primers: Nucleic acid probes and primers may be prepared readily based on the amino acid sequences and nucleic acid sequences provided by this invention. A "probe" comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed in, e.g., Sambrook et al. (eds.), *Molecular Cloning: A Laboratory Manual* 2nd ed., vols. 1–3, Cold Spring Harbor Laboratory Press, Cold Spring Harbor, N.Y., 1989, and Ausubel et al. (eds.) *Current Protocols in Molecular Biology*, Greene Publishing and Wiley-Interscience, New York (with periodic updates), 1987.

"Primers" are short nucleic acids, preferably DNA oligonucleotides 10 nucleotides or more in length. A primer may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR), or other nucleic-acid amplification methods known in the art.

Methods for preparing and using probes and primers are described, for example, in references such as Sambrook et al. (eds.), *Molecular Cloning: A Laboratory Manual* 2nd ed., vols. 1–3, Cold Spring Harbor Laboratory Press, Cold Spring Harbor, N.Y., 1989; Ausubel et al. (eds.), *Current Protocols in Molecular Biology*, Greene Publishing and Wiley-Interscience, New York (with periodic updates), 1987; and Innis et al., *PCR Protocols: A Guide to Methods and Applications*, Academic Press: San Diego, 1990. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with the length of the probe or primer. Thus, for example, a primer comprising 20 consecutive nucleotides will anneal to a target having a higher specificity than a corresponding primer of only 15 nucleotides. Thus, in order to obtain greater specificity, probes and primers may be selected that comprise, for example, 10, 20, 25, 30, 35, 40, 50 or more consecutive nucleotides.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237–244, 1988; Higgins & Sharp, *CABIOS* 5:151–153, 1989; Corpet et al., *Nuc. Acids Res.* 16:10881–10890, 1988; Huang, et al., *CABIOS* 8:155–165, 1992; and Pearson et al., *Meth. in Mol. Biol.* 24:307–331, 1994. Altschul et al., *J. Mol. Biol.* 215: 403–410, 1990, presents a detailed consideration of sequence alignment methods and homology calculations.

The National Center for Biotechnology Information (NCBI) Basic Local Alignment Search Tool (BLAST™, Altschul et al. *J. Mol. Biol.* 215:403–410, 1990) is available from several sources, including the National Center for Biotechnology Information (NCBI, Bethesda, Md.) and on the Internet, for use in connection with the sequence-analysis programs blastp, blastn, blastx, tblastn and tblastx. BLAST™ can be accessed on the internet. A description of how to determine sequence identity using this program is available on the internet.

For comparisons of amino acid sequences of greater than about 30 amino acids, the "Blast 2 sequences" function of the BLAST™ program is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 45%, at least 50%, at least 60%, at least 80%, at least 85%, at least 90%, or at least 95% sequence identity.

Transacylase (an older name for acyltransferase) activity: Enzymes exhibiting transacylase activity are capable of transferring acyl groups, forming either esters or amides, by catalyzing reactions in which an acyl group that is linked to a carrier (acyl-carrier) is transferred to a reactant, thus forming an acyl group linked to the reactant (acyl-reactant).

Transacylases: Transacylases are enzymes that display transacylase activity as described supra. However, all transacylases do not recognize the same carriers and reactants. Therefore, transacylase enzyme-activity assays must utilize different substrates and reactants depending on the specificity of the particular transacylase enzyme. One of ordinary skill in the art will appreciate that the assay described below is a representative example of a transacylase activity assay, and that similar assays can be used to test transacylase activity directed towards different substrates and reactants.

Substantial similarity: A first nucleic acid is "substantially similar" to a second nucleic acid if, when optimally aligned (with appropriate nucleotide deletions or gap insertions) with the other nucleic acid (or its complementary strand), there is nucleotide sequence identity in at least about, for example, 50%, 75%, 80%, 85%, 90% or 95% of the nucleotide bases. Sequence similarity can be determined by comparing the nucleotide sequences of two nucleic acids using the BLAST™ sequence analysis software (blastn) available from The National Center for Biotechnology Information. Such comparisons may be made using the software set to default settings (expect=10, filter=default, descriptions=500 pairwise, alignments=500, alignment view=standard, gap existence cost=11, per residue existence=1, per residue gap cost=0.85). Similarly, a first polypeptide is substantially similar to a second polypeptide if they show sequence identity of at least about 75%–90% or greater when optimally aligned and compared using BLAST™ software (blastp) using default settings.

II. Characterization of acetyl CoA:taxa-4(20),11(12)-dien-5α-ol O-acetyl transacylase A. Enzyme Purification and Library construction Biochemical studies have indicated that the third specific intermediate of the paclitaxel biosynthesis pathway is taxa-4(20),11(12)-dien-5α-yl acetate, because this metabolite serves as a precursor of a series of polyhydroxy taxanes en route to the end-product (Hezari and Croteau, *Planta Medica* 63:291–295, 1997). The responsible enzyme, taxadienol acetyl transacylase, that converts taxadienol to the C5-acetate ester is, thus, an important candidate for cDNA isolation for the purpose of overexpression in relevant producing organisms to increase paclitaxel yield (Walker et al., *Arch. Biochem. Biophys.* 364:273–279, 1999).

This enzyme has been partially purified and characterized with respect to reaction parameters (Walker et al., *Arch. Biochem. Biophys.* 364:273–279, 1999); however, the published fractionation protocol does not yield a pure protein suitable for amino acid microsequencing that is required for an attempt at reverse genetic cloning of the gene. It is also important to note that the gene has no homologs or orthologs (i.e., other terpenoid or isoprenoid O-acetyl transacylases) in the databases to permit similarity-based cloning approaches.

Using methyl jasmonate-induced *Taxus canadensis* cells as an enriched enzyme source, a new isolation and purification protocol (see FIG. 3, and protocol described infra) was developed to efficiently yield homogeneous protein for microsequencing. Although the protein was N-blocked and failed to yield peptides that could be internally sequenced by V8 (endoproteinase Glu-C, Roche Molecular Biochemical, Nutley, N.J.) proteolysis or cyanogen bromide (CNBr) cleavage, treatment with endolysC (endoproteinase Lys-C, Roche Molecular Biochemical, Nutley, N.J.) and trypsin yielded a mixture of peptides. Five of these could be separated by high-performance liquid chromatography (HPLC) and verified by mass spectrometry (MS), and yielded sequence information useful for a cloning effort (FIG. 2).

For cDNA library construction, a stable, methyl jasmonate-inducible *T. cuspidata* suspension cell line was chosen for mRNA isolation because the production of paclitaxel was highly inducible in this system (which permits the preparation of a suitable subtractive library, if necessary). The mixing of experimental protocols as used with different *Taxus* species is not a significant limitation, since all *Taxus* species are known to be very closely related and are considered by several taxonomists to represent geographic variants of the basic species *T. baccata* (Bolsinger and Jaramillo, *Silvics of Forest Trees of North America* (revised), Pacific Northwest Research Station, USDA, p. 17, Portland, Oreg., 1990; and Voliotis, *Isr. J. Botany.* 35:47–52, 1986). Thus, the genes encoding geranylgeranyl diphosphate synthase and taxadiene synthase (early steps of paclitaxel biosynthesis) from *T. canadensis* and *T. cuspidata* evidence only very minor sequence differences. Hence, a method was developed for the isolation of high-quality mRNA from *Taxus* cells (Qiagen, Valencia, Calif.) and this material was employed for cDNA library construction using a commercial kit which is available from STRATAGENE™, La Jolla, Calif.

B. Reverse Genetic Cloning

Of the five peptides that were generated with proteolytic enzymes and were sequenced (FIG. 2), peptide SEQ ID NOs: 30, 31, and 33 were found to exhibit some similarity to the sequences of the only two other plant acetyl transacylases that have been documented, namely, deacetylvindoline O-acetyl transacylase involved in indole alkaloid biosynthesis (St. Pierre et al., *Plant J.* 14:703–713, 1998) and benzyl alcohol O-acetyl transacylase involved in the biosynthesis of aromatic esters of floral scent (Dudareva et al., *Plant J.* 14:297–304, 1998). Lesser resemblance was found to a putative aromatic O-benzoyl transacylase of plant origin (Yang et al., *Plant Mol. Biol.* 35:777–789, 1997). Of the five peptide sequences (FIG. 2), SEQ ID NO: 30 was most suitable for primer design based on codon degeneracy considerations, and two such forward degenerate primers, AT-FOR1 (SEQ ID NO: 34) and AT-FOR2 (SEQ ID NO: 35), were synthesized (FIG. 4). A search of the database with the tryptic peptide ILVYYPPFAGR (SEQ ID NO: 30) revealed two possible variants of this sequence among several gene entries of known and unknown function (these entries are listed in Table 1). Consideration of these distantly related sequences allowed the design of two additional forward degenerate primers (AT-FOR3 (SEQ ID NO: 36) and AT-FOR4 (SEQ ID NO: 37)), and permitted identification of a distal consensus sequence from which a degenerate reverse primer (AT-REV1 (SEQ ID NO: 38)) was designed (FIG. 4). (An alignment of the *Taxus* sequences with the extant database sequence entries of Table 1 illustrates the lack of significant homology between the *Taxus* sequences and any previously described genes.)

TABLE 1

Database (GENBANK ™) sequences used for peptide comparisons. For alignment, see FIG. 6; for placement in dendrogram, see FIG. 7. The accession number is followed by a two-letter code indicating genus and species (AT, *Arabidopsis thaliana*; CM, *Cucumis melo*; CR, *Catharanthus roseus*; DC, *Dianthus caryophyllus*; CB, *Clarkia breweri*; NT, *Nicotiana tabacum*).

| Accession No. | Protein Identification No. | Function |
|---|---|---|
| AC000103_AT SEQ ID NO: 61 | g2213627 | unknown; from genomic sequence for *Arabidopsis thaliana* BAC F21J9 |
| AC000103_AT SEQ ID NO: 62 | g2213628 | unknown; from genomic sequence for *A. thaliana* BAC F21J9 |
| AF002109_AT SEQ ID NO: 63 | g2088651 | unknown; hypersensitivity-related gene 201 isolog |
| AC002560_AT SEQ ID NO: 64 | g2809263 | unknown; from genomic sequence for *A. thaliana* BAC F21B7 |
| AC002986_AT SEQ ID NO: 65 | g3152598 | unknown; similarity to C2-HC type zinc finger protein C.e-MyT1 gb/U67079 from *C. elegans* and to hypersensitivity-related gene 201 isolog T28M21.14 from *A. thaliana* BAC |
| AC002392_AT SEQ ID NO: 69 | g3176709 | putative anthranilate N-hydroxycinnamoyl/benzoyltransferase |
| AL031369_AT SEQ ID NO: 70 | g3482975 | unknown; putative protein |
| Z84383_AT SEQ ID NO: 73 | g2239083 | hydroxycinnamoyl:benzoyl-CoA: anthranilate N-hydroxycinnamoyl: benzoyl transferase |
| Z97338_AT SEQ ID NO: 74 | g2244896 | unknown; similar to HSR201 protein *N. tabacum* |
| Z97338_AT SEQ ID NO: 75 | g2244897 | unknown; hypothetical protein |
| AL049607_AT SEQ ID NO: 76 | g4584530 | unknown; putative protein |
| AF043464_CB SEQ ID NO: 66 | g3170250 | acetyl CoA:benzylalcohol acetyl transferase |
| Z70521_CM SEQ ID NO: 72 | g1843440 | unknown; expressed during ripening of melon (*Cucumis melo* L.) fruits |
| AF053307_CR SEQ ID NO: 68 | g4091808 | deacetylvindoline 4-O-acetyl transferase |
| AC004512_DC SEQ ID NO: 67 | g3335350 | unknown; similar to gb/Z84386 anthranilate N-hydroxycinnamoyl/benzoyltransferase from *Dianthus caryophyllus* |
| X95343_NT SEQ ID NO: 71 | g1171577 | unknown; hypersensitive reaction in tobacco |

PCR amplifications were performed using each combination of forward and reverse primers, and induced *Taxus* cell library cDNA as a target. The amplifications produced, by cloning and sequencing, twelve related but distinct amplicons (each ca. 900 bp) having origins from the various primers (Table 2). These amplicons are designated "Probe 1" through "Probe 12," and their nucleotide and deduced amino acid sequences are listed as SEQ ID NOs: 1–24, respectively.

TABLE 2

Primer combinations, amplicons and acquired genes. The parentheses and brackets are used to designate the primer pair used and the corresponding frequency at which that primer pair amplified the probe.

| Primer Pair | Amplicon Size (bp) | Frequency | Designation | Acquired Gene Designation | Function |
|---|---|---|---|---|---|
| AT-FOR1/AT-REV1 (AT-FOR2/AT-REV1) | 920 | 7/12 (12/31) | Probe 1 | TAX1 (full-length) SEQ ID NO: 27; SEQ ID NO: 28 | taxadienol acetyl transferase |

TABLE 2-continued

Primer combinations, amplicons and acquired genes. The parentheses and brackets are used to designate the primer pair used and the corresponding frequency at which that primer pair amplified the probe.

| Primer Pair | Amplicon Size (bp) | Frequency | Designation | Acquired Gene Designation | Function |
|---|---|---|---|---|---|
| (FIG. 4) | | | SEQ ID NO: 1; SEQ ID NO: 2 | TAX2 (full-length) SEQ ID NO: 25; SEQ ID NO: 26 | benzoyl transferase |
| AT-FOR1/AT-REV1 (AT-FOR2/AT-Rev1) | 920 | 7/12 (2/31) | Probe 2 | Probe 2 was not used, but likely would have acquired TAX2 because the sequence corresponds directly to this gene. | — |
| (FIG. 4) AT-FOR4/AT-REV1 | 903 | 2/29 | SEQ ID NO: 3; SEQ ID NO: 4 Probe 3 | — | — |
| (FIG. 4) AT-FOR3/AT-REV1 | 908 | 1/29 | SEQ ID NO: 5; SEQ ID NO: 6 Probe 4 | — | — |
| (FIG. 4) AT-FOR4/AT-REV1 | 908 | 1/32 | SEQ ID NO: 7; SEQ ID NO: 8 Probe 5 | TAX5 (full-length) SEQ ID NO: 49; SEQ ID NO: 50 | transacylase |
| (FIG. 4) AT-FOR4/AT-REV1 (AT-FOR3/AT-REV1) [AT-FOR4/AT-REV1] | 911 | 8/32 (1/29) [1/32] | SEQ ID NO: 9; SEQ ID NO: 10 Probe 6 | TAX6 (full-length) SEQ ID NO: 44; Seq ID No: 45 | 10-deacetylbaccatin III-10-O-acetyl transferase |
| (FIG. 4) AT-FOR3/AT-REV1 | 968 | 6/29 | SEQ ID NO: 11; SEQ ID NO: 12 Probe 7 | TAX7 (full-length) SEQ ID NO: 51; SEQ ID NO: 52 | transacylase |
| (FIG. 4) AT-FOR3/AT-REV1 (AT-FOR4/AT-REV1) | 908 | 1/29 (2/32) | SEQ ID NO: 13; SEQ ID NO: 14 Probe 8 | — | — |
| (FIG. 4) AT-FOR2/AT-REV1 (AT-FOR3/AT-REV1) | 908 | 1/32 (5/29) | SEQ ID NO: 15; SEQ ID NO: 16 Probe 9 | TAX9 (full-length) SEQ ID NO: 59, SEQ ID NO: 60 | transacylase |
| (FIG. 4) AT-FOR4/AT-REV1 | 911 | 2/32 | SEQ ID NO: 17; SEQ ID NO: 18 Probe 10 | TAX10 (full-length) SEQ ID NO: 53; SEQ ID NO: 54 | transacylase |
| (FIG. 4) AT-FOR4/AT-REV1 | 920 | 1/32 | SEQ ID NO: 19; SEQ ID NO: 20 Probe 11 | — | — |
| (FIG. 4) AT-FOR3/AT-REV1 (AT-FOR4/AT-REV1) | 908 | 3/29 (1/32) | SEQ ID NO: 21; SEQ ID NO: 22 Probe 12 | TAX12 (full-length) SEQ ID NO: 55, SEQ ID NO: 56 | transacylase |
| (FIG. 4) | | | SEQ ID NO: 23; SEQ ID NO: 24 TAX13 does not appear to directly correspond to any of the above listed Probes | TAX13 (full-length) SEQ ID NO: 57; SEQ ID NO: 58 | transacylase |

Notably, Probe 1, derived from the primers AT-FOR1 (SEQ ID NO: 34) and AT-REV1 (SEQ ID NO: 38), amplified a ~900 bp DNA fragment encoding, with near identity, the proteolytic peptides corresponding to SEQ ID NOs: 31–33 of the purified protein. These results suggested that the amplicon Probe 1 represented the target gene for taxadienol acetyl transacylase. Probe 1 was then $^{32}$P-labeled and employed as a hybridization probe in a screen of the methyl jasmonate-induced *T. cuspidata* suspension cell λZAP II™ cDNA library. Standard hybridization and purification procedures ultimately led to the isolation of three full-length, unique clones designated TAX1 (SEQ ID NO: 28), TAX2 (SEQ ID NO: 26), and TAX6 (SEQ ID NOS: 27, 25, and 44, respectively).

C. Sequence Analysis and Functional Expression

Clone TAX1 bears an open reading frame of 1317 nucleotides (nt; SEQ ID NO: 27)) and encodes a deduced protein of 439 amino acids (aa; SEQ ID NO: 28) with a calculated molecular weight of 49,079 kDa. Clone TAX2 bears an open reading frame of 1320 nt (SEQ ID NO: 25) and encodes a deduced protein of 440 aa (SEQ ID NO: 26) with a calculated molecular weight of 50,089 kDa. Probe 6 (SEQ ID NO: 3) was found to bear 80% nucleotide-level homology to TAX1 (SEQ ID NO: 27), suggesting that the full-length version of probe 6 may encode anotehr taxoid acetyl transferase. Probe 6 was 32P-labeled and used as a probe to screen a *Taxus* cell suspension cDNA library, the full-length cDNA was obtained and designated as TAX6. Clone TAX6 bears an open reading frame of 1320 nt (SEQ ID NO: 44) and encodes a deduced protein of 440 aa (SEQ ID NO: 45) with a calculated molecular weight of 49,000 kDa.

The sizes of TAX1 (SEQ ID NO: 28) and TAX2 (SEQ ID NO: 26) are consistent with the molecular weight of the native taxadienol transacetylase (MW ~50,000) determined by gel-permeation chromatography (Walker et al., *Arch. Biochem. Biophys.* 364:273–279, 1999) and SDS polyacrylamide gel electrophoresis (SDS-PAGE). The deduced amino acid sequences of both TAX1 (SEQ ID NO: 28) and TAX2 (SEQ ID NO: 26) also remotely resemble those of other acetyl transacylases (50–56% identity; 64–67% similarity) involved in different pathways of secondary metabolism in plants (St. Pierre et al., *Plant J.* 14:703–713, 1998; and Dudareva et al., *Plant J.* 14:297–304, 1998). When compared to the amino acid sequence information from the tryptic peptide fragments, TAX1 (SEQ ID NO: 28) exhibited a very close match (91% identity), whereas TAX2 (SEQ ID NO: 26) exhibited conservative differences (70% identity).

The TAX6 (SEQ ID NO: 45) calculated molecular weight of 49,052 kDa is consistent with that of the native TAX6 (SEQ ID NO: 45) protein (50 kDa), determined by gel permeation chromatography, indicating the protein to be a functional monomer, and is very similar to the size of the related, monomeric taxadien-5α-ol transacetylase (MW=49,079). The acetyl CoA:10-deacetylbaccin III-10-O-acetyl transferase from *Taxus cuspidata* appears to be substantially different in size from the acetyl CoA:10-hydroxytaxane-O-acetyl transferase recently isolated from *Taxus chinensis* and reported at a molecular weight of 71,000 (Menhard and Zenk, *Phytochemistry* 50:763–774, 1999).

The deduced amino acid sequence of TAX6 (SEQ ID NO: 45) resembles that of TAX1 (SEQ ID NO: 28) (64% identity; 80% similarity) and those of other acetyl transferases (56–57% identity; 65–67% similarity) involved in different pathways of secondary metabolism in plants (Dudareva et al., *Plant J.* 14:297–304, 1998; St-Pierre et al., *Plant J.* 14:703–713, 1998). Additionally both TAX6 (SEQ ID NO: 45) and TAX2 (SEQ ID NO: 26) possess the HXXXDG (SEQ ID NO: 48) (residues H162, D166, and G167 in TAX6 (SEQ ID NO: 45), and residues H159, D163, and G164 in TAX2 (SEQ ID NO: 26), respectively) motif found in other acyl transferases (Brown et al., *J. Biol. Chem.* 269:19157–19162, 1994; Carbini and Hersh, *J. Neurochem.* 61:247–253, 1993; Hendle et al., *Biochemistry* 34:4287–4298, 1995; and Lewendon et al., *Biochemistry* 33:1944–1950, 1994); this sequence element has been suggested to function in acyl group transfer from acyl CoA to the substrate alcohol (St. Pierre et al., *Plant J* 14:703–713, 1998).

To determine the identity of the putative taxadienol acetyl transacylase, TAX1 (SEQ ID NO: 28), TAX2 (SEQ ID NO: 26), and TAX6 (SEQ ID NO: 45) were subcloned in-frame into the expression vector pCWori+ (Barnes, *Methods Enzymol.* 272:3–14, 1996) and expressed in *E. coli* JM109 cells. The transformed bacteria were cultured and induced with isopropyl β-D-thiogalactoside (IPTG), and cell-free extracts were prepared and evaluated for taxadienol acetyl transacylase activity using the previously developed assay procedures (Walker et al., *Arch. Biochem. Biophys.* 364:273–279, 1999). Clone TAX1 (corresponding directly to Probe 1) expressed high levels of taxadienol acetyl transacylase activity (20% conversion of substrate to product), as determined by radiochemical analysis; the product of this recombinant enzyme was confirmed as taxadienyl-5α-yl acetate by gas chromatography-mass spectrometry (GC-MS) (FIGS. 5A–5G). Clone TAX2 did not express taxadienol acetyl transacylase activity and was inactive with the [$^3$H]taxadienol and acetyl CoA co-substrates. However, the clone TAX2 may encode an enzyme for a step later in the paclitaxel biosynthetic pathway (TAX2 has been shown to correspond to Probe 2). Neither of the recombinant proteins expressed from TAX1 (SEQ ID NO: 28) or TAX2 (SEQ ID NO: 26) was capable of acetylating the advanced paclitaxel precursor 10-deacetyl baccatin III to baccatin III. Thus, based on the demonstration of functionally expressed activity, and the resemblance of the recombinant enzyme in substrate specificity and other physical and chemical properties to the native form, clone TAX1 was confirmed to encode the *Taxus* taxadienol acetyl transacylase.

Additionally, the heterologously expressed TAX6 (SEQ ID NO: 45) was partially purified by anion-exchange chromatography (O-diethylaminoethylcellulose, Whatman, Clifton, N.J.) and ultrafiltration (AMICON™ DIAFLO™ YM 10 membrane, MILLIPORE™, Bedford, Mass.) to remove interfering hydrolases from the bacterial extract, and the recombinant enzyme was determined to catalyze the conversion of 10-deacetylbaccatin III to baccatin III; the latter is the last diterpene intermediate in the paclitaxel biosynthetic pathway. The optimum pH for TAX6 (SEQ ID NO: 45) was determined to be 7.5, with half-maximal velocities at pH 6.4 and 7.8. The $K_m$ values for 10-deacetylbaccatin III and acetyl CoA were determined to be 10 μM and 8 μM, respectively, by Lineweaver-Burk analysis (for both plots $R^2$=0.97). These kinetic constants for TAX6 (SEQ ID NO: 45) are comparable to the taxa-4(20),11(12)-dien-5α-ol acetyl transferase possessing $K_m$ values for taxadienol and acetyl CoA of 4 μM and 6 μM, respectively. The TAX6 (SEQ ID NO: 45) appears to acetylate the 10-hydroxyl group of taxoids with a high degree of regioselectivity, since the enzyme does not acetylate the 1β-, 7β-, or 13α-hydroxyl groups of 10-deacetylbaccatin III, nor does it acetylate the 5α-hydroxyl group of taxa-4(20),11(12)-dien-5α-ol.

III. Other Transacylases of the Paclitaxel Pathway

A. Overview

Screening for transacylase activity can be done by initially obtaining and/or synthesizing substrates, as described below. The individual transacylase enzymes, derived from cDNA clones TAX2, TAX5, TAX7, TAX9, TAX10, TAX12, and TAX13 (SEQ ID NOS: 25, 49, 51, 59, 53, 55, and 57, respectively) are expressed in bacteria as described below. The expressed enzymes are subjected to a crude purification procedure and screened for their ability to act upon the following substrates: 2-debenzoyl-7,13-diacetylbaccatin III, N-debenzoyltaxol, benzoyl CoA, and co-substrates, baccatin III and phenylisoserinyl CoA. The results from these screening assays can identify which of the above-mentioned clones is a debenzoyltaxol-N-benzoyl transferase and which is a baccatin III-13-O-phenylisoserinyl transferase.

B. Production of Suitable Substrates

1. 2-debenzoyl-7,13-diacetylbaccatin III

Authentic 10-deacetylbaccatin III was obtained from either Hauser Chemical Research Inc. (Boulder, Colo.), Dabur India Ltd. (New Delhi, India), or Natland International Corp. (Morrisville, N.C.). (2α,5α)-Dihydroxy-taxa-4(20),11(12)-diene was a generous gift from Robert Williams (Colorado State University, Boulder, Colo.). Methyl jasmonate was obtained from Bedoukian Research, Inc. (Danbury, Conn.). Benzoyl coenzyme A as the sodium salt was purchased from Sigma Chemical Co. (St. Louis, Mo.). [7-$^{14}$C]Benzoic acid was purchased from NEN Life Sciences Products (Boston, Mass.). All other reagents were purchased from ALDRICH™ Chemical Co. (Milwaukee, Wis.), unless noted otherwise, and were used without further purification.

The synthesis of 2-debenzoyl-7,13-diacetylbaccatin III was initiated by first synthesizing 7,13-diacetylbaccatin III as follows: To a stirred solution of 10-deacetylbaccatin III (160 mg, 294 μmol) in dry $CH_2Cl_2$ (5 mL) at 25° C. under nitrogen were added acetic anhydride (20 equiv.), dimethylaminopyridine (20 equiv.), and triethylamine (50 μL, 361 μmol). After 16 hours, the reaction was diluted with EtOAc (50 mL) and quenched with water (10 mL). The mixture was stirred for 15 minutes, and the aqueous fraction was separated and extracted with EtOAc (2×25 mL). The combined organic fractions were washed with brine, 0.1 N HCl, water, and dried over anhydrous $MgSO_4$. The organic solvent was evaporated under reduced pressure, and the crude product was purified by silica gel flash column chromatography (EtOAc:hexane, 60:40, v/v) to yield pure 7,13-diacetylbaccatin III (see FIG. 11) (180 mg, 91% yield, 99% purity by $^1$H-NMR). $^1$H-NMR (300 MHz, $CDCl_3$)δ: 1.10 (s, $CH_3$), 1.14 (s, $CH_3$), 1.74 (s, $CH_3$), 1.77 (ddd, J=1.8, 10.8, and 14.7 Hz, H-6β), 1.90 (d, J=1.2 Hz, vinyl-$CH_3$) 1.97 (s, C(O)$CH_3$), 2.12 (s, C(O)$CH_3$), 2.14 (s, C(O)$CH_3$), 2.17 (d, J=8.7 Hz, H-14), 2.29 (s, C(O)$CH_3$), 2.53 (ddd, J=7.2, 9.6, and 14.4 Hz, H-6α), 3.89 (d, J=6.9 Hz, H-3), 4.09 (d, J=8.4 Hz, H-20α), 4.24 (d, J=8.4 Hz, H-20β), 4.91 (dd, J=1.8 and 9.6 Hz, H-5), 5.53 (dd, J=7.2 and 10.5 Hz, H-7), 5.60 (d, J=6.9 Hz, H-2), 6.10 (dt, J=1.2 and 8.7 Hz, H-13), 6.19 (s, H-10), 7.39–8.01 (aromatic protons). APCI-MS: m/z 671 (PH+).

Bis(2-methoxyethoxy)-aluminum hydride (65+ wt % in toluene, 3 equiv.) was added dropwise to a stirred solution of 7,13-diacetylbaccatin III (170 mg, 253 μmol) in dry THF (2 mL) at 0° C. After stirring for 30 minutes at 0° C., the reaction was quenched by dropwise addition of saturated $NH_4Cl$. The mixture was stirred for 10 minutes, then warmed to room temperature and diluted with EtOAc (50 mL), followed by addition of water (10 mL). The aqueous phase was separated and extracted again with EtOAc (2×25 mL). The combined organic fractions were washed with brine and water, then dried over anhydrous $MgSO_4$. The solvent was evaporated and the crude product was purified by silica gel flash column chromatography (40–60% EtOAc gradient in hexane) to yield 2-debenzoyl-7,13-diacetylbaccatin III (see FIG. 11) (60 mg, 42% yield, 99% purity by $^1$H-NMR). $^1$H-NMR (300 MHz, $CDCl_3$)δ: 1.04 (s, $CH_3$), 1.22 (s, $CH_3$), 1.77 (s, $CH_3$), 1.85 (ddd, J=1.8, 10.8, and 14.4 Hz, H-6β), 1.90 (d, J=1.2 Hz, vinyl-$CH_3$), 2.02 (s, C(O)$CH_3$), 2.14 (s, C(O)$CH_3$), 2.15 (s, C(O)$CH_3$), 2.20 (s, C(O)$CH_3$), 2.58 (ddd, J=7.2, 9.6, and 14.4 Hz, H-6α), 2.65 (d, J=5.1 Hz, OH at C-2), 3.58 (d, J=6.9 Hz, H-3), 3.90 (dd, J=5.4 and 6.5 Hz, H-2), 4.49 (d, J=9.6 Hz, H-20α), 4.63 (d, J=9.6 Hz, H-20β), 4.97 (dd, J=1.8 and 9.6 Hz, H-5), 5.55 (dd, J=7.2 and 10.7 Hz, H-7), 6.15 (dt, J=1.2 and 9.6 Hz, H-13), 6.18 (s, H-10), H-14 proton signal obscured. APCI-MS: m/z 567 (PH+)

Regarding the synthesis of [7-$^{14}$C]benzoyl coenzyme A, the following method was adapted from a procedure described for the synthesis of long-chain acyl CoA esters (Rasmussen et al., *Biochem. J.* 265:849–855, 1990). To a solution of [7-$^{14}$C]benzoic acid (3.3 mg, 27 μmol, sp. ac. 18.5 Ci/mol) in $CH_2Cl_2$:THF (5:2, v/v, 1.4 mL) under nitrogen was added 1 M triethylamine in $CH_2Cl_2$ (3.0 μL, 30 μmol) in one portion. The mixture was stirred together for 10 minutes at room temperature. Ethyl chloroformate (2.57 μL, 2.9 mg, 27 μmol) was added in one portion and the reaction was stirred for 1 hour at room temperature. The solvents were evaporated, and the residue was dissolved in 0.5 mL t-butanol. Coenzyme A as the sodium salt (23 mg, 30 μmol dissolved in 0.5 mL of 0.4 M $NaHCO_3$) was added to the butanolic solution, and the reaction mixture was stirred for 0.5 hours at room temperature. The reaction mixture was quenched with 1 M HCl (200 μL) and adjusted to pH 5 with 15 mM $NaH_2PO_4$ (pH 4.8). The solvents were evaporated in vacuo (5 hours) at room temperature. To remove residual t-butanol, the sample was dissolved in dry methanol, and the solvent removed under vacuum. The remaining residue was resuspended in 15 mM $NaH_2PO_4$ (pH 6.9, 7 mL). The crude product was purified using a C18 SEP-PAK™ cartridge (500 mg C18 silica gel, MILLIPORE™ Corp, Milford, Mass.) that was first washed with methanol (2×6 mL) and water (2×6 mL), then finally equilibrated with 15 mM $NaH_2PO_4$ (pH 6.9, 2×6 mL). The entire volume of crude sample was loaded onto the column eluted with 5 mL portions of increasing methanol in 15 mM $NaH_2PO_4$ (pH 6.9) to yield [7-$^{14}$C]benzoyl coenzyme A as the sodium salt (eluted in 10–15% methanol). The chemical purity (99%) of the synthetic CoA thioester was assessed by analytical TLC (silica gel developed with n-butanol:$H_2O$:AcOH, 5:3:2, v/v/v) and comparison to authentic, co-chromatographed benzoyl coenzyme A (Rf=0.4). The TLC plate was air dried at 25° C., and the radiochemical purity of the synthetic product was determined to be 99% by liquid scintillation counting of scraped regions of the plate co-migrating with authentic standard, and regions both below and above it. The [7-$^{14}$C]benzoyl CoA so isolated was lyophilized, resuspended in water (10 mL) to reconstitute to 15 mM $NaH_2PO_4$, and then carefully adjusted to pH 5 with 1 N HCl. The solution was extracted with ether (3×5 mL) to remove trace organic contaminants, and the residual ether was evaporated under a stream of nitrogen to yield a 1.35 mM solution of [7-$^{14}$C]benzoyl coenzyme A.

2. Production of N-debenzoyltaxol

N-debenzoyltaxol can be prepared by adding excess units of N-acylamino acid amidohydrolase (Sigma Chemical Co., St. Louis, Mo.) from porcine kidney to a suspension of ~5 mg N-debenzoyl-(N-phenylacetyltaxol) (a gift from Hauser Chemical Research (Boulder, Colo.)). The resulting solution is stirred at room temperature. After 18 hours, the solution is acidified to pH 3 with 1 N HCl and extracted with ether. The aqueous fraction is lyophilized, the remaining residue can be dissolved in a minimal volume of buffer, and the crude product can be purified by cation exchange column chromatography. Purified N-debenzoyltaxol can be precipitated with a dilute solution of $NH_4OH$, placed on ice for 0.5 hours, and centrifuged to pellet the product. The supernatant is decanted, the precipitate rinsed with a minimal volume of water, and the product lyophilized. The isolated product can be authenticated by $^1$H-NMR on a VARIAN™ MERCURY™ 300 (with deuterated chloroform as solvent and internal reference) and direct injection mass spectrometry (HEWLETT-PACKARD™ Series 1100 MSD system in atmospheric pressure chemical ionization mode).

3. Synthesis of Phenylisoserinyl CoA

Phenylisoserinyl CoA can be prepared by dissolving N-benzoyl-(2R,3S)-3-phenylisoserine (200 mg) in 5 mL of water. The resulting solution can be acidified to pH 2 with 1 N HCl and refluxed for 5 hours. The reaction mixture is cooled to room temperature and extracted with ether, and the aqueous fraction is lyophilized to dryness. The remaining crude product can be dissolved in a minimum volume of water and adjusted to pH 5 with dilute $NH_4OH$ to recrystallize the (2R,3S)-3-phenylisoserine. The product purity can be accessed by $^1$H-NMR (with $D_2O$ as solvent and internal reference). Excess units of acyl-coenzyme A synthetase (Sigma Chemical Co., St. Louis, Mo.) and coenzyme A (Sigma Chemical Co., St. Louis, Mo.) are added to a solution of (2R,3S)-3-phenylisoserine (ALDRICH™ Chemical Co., Milwaukee, Wis.) dissolved in an appropriate buffer (pH 8). The product can be purified by C18 column chromatography and the product purity determined by silica gel TLC and $^1$H-NMR (with $D_2O$ as solvent and internal reference).

B. Crude Isolation of the Enzymes

TAX2, TAX5, TAX7, TAX9, TAX10, TAX 12, and TAX13 (SEQ ID NOS: 25, 49, 44, 60, 51, 53, 55, and 57, respectively) were expressed in bacteria using the following protocol. For a typical preparation of the recombinant enzyme, each of the *E. coli* cultures transformed with a pCWori+ vector harboring a putative transacylase gene was grown overnight at 37° C. in 5 mL Luria-Bertani medium supplemented with 50 μg ampicillin/mL. 1 mL of these cultures was individually added to separate aliquots of 100 mL Terrific Broth culture medium (6 g bacto-tryptone (Difco Laboratories, Spark, Md.), 12 g yeast extract (EM Science, Cherryhill, N.J.), and 2 mL glycerol in 500 mL water) and grown at 37° C. After 3 hours, the medium was supplemented with 1 mM isopropyl-β-D-thiogalactopyranoside for induction and 50 μg ampicillin/mL, and the cultures were grown at 25° C. After 18 hours, the bacteria were harvested by centrifugation, resuspended in 25 mL of assay buffer (25 mM Mopso, pH 7.4), and disrupted by sonication at 0° C. The resulting homogenates were centrifuged at 15,000×g to pellet debris. The resulting supernatants were centrifuged at 90,000×g to provide the soluble enzyme fractions.

C. Screening Assay

A 1-mL aliquot of each soluble enzyme preparation was incubated with 2-debenzoyl-7,13-diacetylbaccatin III (500 μM) and [7-$^{14}$C]benzoyl coenzyme A (500 μM, 9.3 μCi) for 1.5 hours at 31° C. The reaction mixtures were extracted with ether (2 mL), and the organic phases were removed and concentrated in vacuo. The resulting crude products of the assay were dissolved in acetonitrile (50 μL) and analyzed by radio-HPLC using a Perkin Elmer HPLC ISS 200 coupled to a PACKARD RADIOMATIC™ radioactivity detector series A100 (Canberra, Ind., Meriden, Conn.) (see FIGS. 12A and 12B for a representative chromatogram). The samples were separated on a VYDAC™ (Hesperia, Calif.) $C_{18}$ column (5μ 250×4.6 mm) by elution at 1 mL/min with a linear gradient starting from 30:70 $CH_3CN:H_2O$ to 60:40 $CH_3CN:H_2O$ over 30 minutes, then to 100% $CH_3CN$ with a linear gradient over 5 minutes, held at 100% $CH_3CN$ for 5 minutes, and, finally, returned to the initial conditions over 5 minutes. A detected biosynthetic product absorbing at $A_{228}$ and possessing a coincidental radioactivity response with the same retention time as authentic 7,13-diacetylbaccatin III directed efforts towards large-scale preparation (4 L) of the enzyme expressed from a single *E. coli* JM109 transformant bearing the clone designated TAX2. The product generated by large-scale preparation of the putative TAX2 (SEQ ID NO: 26) benzoyl transferase (~50μg) was analyzed by combined liquid chromatography-mass spectrometry (LC-MS) using a HEWLETT-PACKARD™ Series 1100 MSD in the atmospheric pressure chemical ionization (APCI) mode. The sample, dissolved in acetonitrile (200 μL), was loaded (5 μL) onto a PHENOMENEX™ (Torrance, Calif.) CUROSIL-G™ column (5μ 250×4.6 mm) that was eluted at 1 mL/minute with 30:70 $CH_3CN:H_2O$ for 5 minutes, increased linearly to 80:20 $CH_3CN:H_2O$ over 55 minutes, and then held for 5 minutes (with return to initial conditions over 0.1 minutes and equilibration for 10 minutes). The column effluent was directed to the APCI inlet of the mass spectrometer for analysis (see FIG. 13A for a representative spectrum). Additional enzymatic product (~500 μg) was purified by silica gel TLC (ethyl acetate:hexane, 60:40, v/v). The band co-migrating with authentic 7,13-diacetylbaccatin III ($R_f$=0.33) was isolated, dissolved in 0.5 mL deuterated chloroform as internal standard, and analyzed by proton nuclear magnetic resonance spectroscopy ($^1$H-NMR) using a VARIAN™ MERCURY™ 300 instrument.

D. Kinetic Characterization Assays

Large-scale (4 L) cultures of *E. coli* JM109 cells harboring the recombinant *Taxus* TAX2 (SEQ ID NO: 26) gene were grown, harvested, and extracted as described above. Following preparation of the soluble enzyme fraction and demonstration (by sodium dodecylsulfate polyacrylamide electrophoresis (SDS-PAGE) analysis) that a protein of the appropriate size (~50 kDa) was expressed in operationally soluble form, the protein fraction (100 mL) was applied to a column of O-diethylaminoethyl-SEPHAROSE™ (2.8×20 cm, Sigma Chemical Co. (St. Louis, Mo.)) that was previously washed with 25 mM Mopso buffer (pH 7.4) containing 3 mM dithiothreitol and 1 M NaCl, and then equilibrated with this buffer (without NaCl). Following removal of unbound material, protein was eluted with a linear gradient of from 0 to 200 mM NaCl in equilibration buffer (200 mL total volume, at 3 mL/minute). Fractions containing the benzoyl transferase activity (eluting at ~175 mM NaCl) were combined (~100 mL) and subjected to ultrafiltration (AMICON™ YM 10 membrane, MILLIPORE™, Bedford, Mass.) and repeated dilution to reduce the salt concentration to ~5 mM. This enzyme preparation was used for kinetic evaluation of the heterologously expressed 2-debenzoyl-7, 13-diacetylbaccatin III-2-O-benzoyl transferase (TAX2; SEQ ID NO: 26), and can be used to produce other transacylase enzymes such as baccatin III-13-O-phenylisoserinyl transacylase, and debenzoyltaxol-N-benzoyl transacylase.

For kinetic evaluations, linearity with respect to protein concentration and time was first established, and the concentrations of 2-debenzoyl-7,13-diacetylbaccatin III (0–1000 μM) and [7-$^{14}$C]benzoyl CoA (0–1000 μM) were independently varied while the remaining reactant was maintained at saturation (2 mM). Double reciprocal plots were constructed for each data set, and the equation of the best-fit line ($R^2$=0.99) was determined (KALEIDA-GRAPH™, version 3.08, SYNERGY SOFTWARE™, Reading, Pa.). To examine the influence of pH on benzoyl transferase activity, enzyme preparations (1 mL, ~80–100 μg protein) were concentrated (NANOSEP™ 30 microconcentrator, Gelman Laboratory, Ann Arbor, Mich.) to 150 μL and then diluted, respectively, with 1.35 mL Mes (pH 6), Mopso (pH 7), glycine (pH 8), Capso (pH 9), or Caps (pH 10 and 11) buffers, all at 25 mM containing 3 mM dithiothreitol, before the assay.

E. Predicted Activity

Comparison of the deduced amino acid sequences of TAX5, TAX7, TAX9, TAX10, TAX 12, and TAX13 (SEQ ID NOS: 50, 52, 60, 54, 56, and 58, respectively) with that of TAX2 (SEQ ID NO: 26), defined as a benzoyl transferase, revealed that TAX13 encodes a peptide sequence bearing the highest amino acid similarity (74%) and identity (68%) (see Table 3 below and FIGS. 14 and 15) to the *Taxus cuspidata* taxane-2α-O-benzoyl transferase, suggesting that TAX13 encodes another taxane benzoyl transferase.

were purified by HPLC and sequenced, and one suitable sequence was used to design a set of degenerate PCR primers. Several primer combinations were employed to amplify a series of twelve related, gene-specific DNA sequences (Probes 1–12). Nine of these gene-specific sequences were used as hybridization probes to screen an induced *Taxus cuspidata* cell cDNA library. This strategy allowed for the successful isolation of nine full-length transacylase cDNA clones. The identity of one of these clones was confirmed by sequence matching to the peptide fragments described above and by heterologous functional expression of transacylase activity in *Escherichia coli*.

B. Culture of Cells

Initiation, propagation and induction of *Taxus* sp. cell cultures, reagents, procedures for the synthesis of substrates and standards, and general methods for transacylase isolation, characterization and assay have been previously described (Hefner et al., *Arch. Biochem. Biophys.* 360: 62–75, 1998; and Walker et al., *Arch. Biochem. Biophys.* 364:273–279, 1999). Since all designated *Taxus* species are considered to be closely related subspecies (Bolsinger and Jaramillo, *Silvics of Forest Trees of North America* (revised), Pacific Northwest Research Station, USDA, Portland, Oreg., 1990; and Voliotis, *Isr. J. Botany* 35:47–52, 1986), the *Taxus*

TABLE 3

|       | TAX1 | TAX2 | TAX5 | TAX6 | TAX7 | TAX9 | TAX10 | TAX12 | TAX13 | PCHCBT |
|-------|------|------|------|------|------|------|-------|-------|-------|--------|
| TAX1  |      | S: 74%, I: 68% | S: 71%, I: 62% | S: 74%, I: 66% | S: 74%, I: 66% | S: 76%, I: 69% | S: 71%, I: 64% | S: 74%, I: 64% | S: 72%, I: 63% | S: 66%, I: 54% |
| TAX2  |      |      | S: 70%, I: 63% | S: 70%, I: 65% | S: 70%, I: 64% | S: 71%, I: 64% | S: 69%, I: 60% | S: 71%, I: 63% | S: 74%, I: 68% | S: 70%, I: 57% |
| TAX5  |      |      |      | S: 69%, I: 62% | S: 74%, I: 67% | S: 70%, I: 62% | S: 67%, I: 59% | S: 67%, I: 57% | S: 67%, I: 59% | S: 64%, I: 52% |
| TAX6  |      |      |      |      | S: 73%, I: 66% | S: 74%, I: 68% | S: 74%, I: 66% | S: 72%, I: 66% | S: 72%, I: 63% | S: 63%, I: 50% |
| TAX7  |      |      |      |      |      | S: 76%, I: 68% | S: 73%, I: 65% | S: 71%, I: 61% | S: 70%, I: 64% | S: 67%, I: 55% |
| TAX9  |      |      |      |      |      |      | S: 74%, I: 66% | S: 73%, I: 66% | S: 71%, I: 58% | S: 65%, I: 54% |
| TAX10 |      |      |      |      |      |      |       | S: 69%, I: 61% | S: 67%, I: 58% | S: 64%, I: 53% |
| TAX12 |      |      |      |      |      |      |       |       | S: 68%, I: 58% | S: 66%, I: 53% |
| TAX13 |      |      |      |      |      |      |       |       |       | S: 67%, I: 56% |

Additionally, comparison of the deduced peptide sequences of TAX2, TAX5, TAX7, TAX9, TAX10, TAX 12, and TAX13 (SEQ ID NOS: 25, 49, 44, 60, 51, 53, 55, and 57, respectively) with that of a dual-function phenylpropanoyl/benzoyl transacylase (namely, an anthranilate hydroxycinnamoyl/benzoyl tranferase (PCHCBT) isolated from *Dianthus caryophyllus* (Yang et al., *Plant Mol. Biol.* 35:777–789, 1997)), revealed the highest similarity (67%) and identity (~56%) (see Table 3, FIGS. 14 and 15) between the deduced peptide of TAX7 and PCHCBT, suggesting that TAX7 encodes the C 13 phenylisoserinyl (a phenylpropanoid) transferase.

IV. Isolating a Gene Encoding acetyl CoA:taxa-4(20),11 (12)-dien-5α-ol O-acetyl transacylase A. Experimental Overview A newly designed isolation and purification method is described below for the preparation of homogeneous taxadien-5α-ol acetyl transacylase from *Taxus canadensis*. The purified protein was N-terminally blocked, thereby requiring internal amino acid microsequencing of fragments generated by proteolytic digestion. Peptide fragments so generated cell sources were chosen for operational considerations because only minor sequence differences and/or allelic variants between proteins and genes of the various "species" were expected. Thus, *Taxus canadensis* cells were chosen as the source of transacetylase because they express transacetylase at high levels, and *Taxus cuspidata* cells were selected for cDNA library construction because they produce paclitaxel at high levels.

C. Isolation and Purification of the Enzyme

No related terpenol transacylase genes are available in the databases (see below) to permit homology-based cloning. Hence, a protein-based (reverse genetic) approach to cloning the target transacetylase was required. This reverse genetic approach required obtaining a partial amino acid sequence, generating degenerate primers, amplifying a portion of cDNA using PCR, and using the amplified fragment as a probe to detect the correct clone in a cDNA library.

Unfortunately, the previously described partial protein purification protocol, including an affinity chromatography step, did not yield pure protein for amino acid microsequencing, nor did the protocol yield protein in useful amounts, or provide a sufficiently simplified SDS-PAGE banding pattern to allow assignment of the transacetylase activity to a specific protein (Walker et al., *Arch. Biochem. Biophys.* 364:273–279, 1999). Furthermore, numerous variations on the affinity chromatography step, as well as the earlier anion exchange and hydrophobic interaction chromatography steps, failed to improve the specific activity of the preparations due to the instability of the enzyme upon manipulation. Also, a five-fold increase in the scale of the preparation resulted in only marginally improved recovery (generally <5% total yield accompanied by removal of >99% of total starting protein). Furthermore, because the enzyme could not be purified to homogeneity, and attempts to improve stability by the addition of polyols (sucrose, glycerol), reducing agents ($Na_2S_2O_5$, ascorbate, dithiothreitol, β-mercaptoethanol), and other proteins (albumin, casein) were also not productive (Walker et al., *Arch. Biochem. Biophys.* 364:273–279, 1999), this approach had to be abandoned.

To overcome the problem described above, the following isolation and purification procedure was used. The purity of the taxadienol acetyl transacylase after each fractionation step was assessed by SDS-PAGE according to Laemmli (Laemmli, *Nature* 227:680–685, 1970); quantification of total protein after each purification step was carried out by the method of Bradford, *Anal. Biochem.* 72:248–254, 1976, or by Coommassie Blue staining, and transacylase activity was assessed using the methods described in Walker et al., *Arch. Biochem. Biophys.* 364:273–279, 1999.

Procedures for protein staining have been described (Wray et al., *Anal. Biochem.* 118:197–203, 1991). The preparation of the *T. canadensis* cell-free extracts and all subsequent procedures were performed at 0–4° C. unless otherwise noted. Cells (40 g batches) were frozen in liquid nitrogen and thoroughly pulverized for 1.5 minutes using a mortar and pestle. The resulting frozen powder was transferred to 225 mL of ice cold 30 mM HEPES buffer (pH 7.4) containing 3 mM dithiothreitol (DTT), XAD-4 polystyrene resin (12 g) and polyvinylpolypyrrolidone (PVPP, 12 g) to adsorb low molecular weight resinous and phenolic compounds. The slurry was slowly stirred for 30 minutes, and the mixture was filtered through four layers of cheese cloth to remove solid absorbents and particulates. The filtrate was centrifuged at 7000 g for 30 minutes to remove cellular debris, then at 100,000 g for 3 hours, followed by 0.2-μm filtration to yield a soluble protein fraction (in ~200 mL buffer) used as the enzyme source.

The soluble enzyme fraction was subjected to ultrafiltration (DIAFLO™ YM 30 membrane, MILLIPORE™, Bedford, Mass.) to concentrate the fraction from 200 mL to 40 mL and to selectively remove proteins of molecular weight lower than the taxadien-5α-ol acetyl transacylase (previously established at 50,000 Da in Walker et al., *Arch. Biochem. Biophys.* 364:273–279, 1999). Using a peristaltic pump, the concentrate (40 mL) was applied (2 mL/minute) to a column of O-diethylaminoethylcellulose (2.8×10 cm, WHATMAN™ DE-52, Fairfield, N.J.) that had been equilibrated with "equilibration buffer" (30 mM HEPES buffer (pH 7.4) containing 3 mM DTT). After washing with 60 mL of equilibration buffer to remove unbound material, the proteins were eluted with a step gradient of the same buffer containing 50 mM (25 mL), 125 mM (50 mL), and 200 mM (50 mL) NaCl.

The fractions were assayed as described previously (Walker et al., *Arch. Biochem. Biophys.* 364:273–279, 1999), and those containing taxadien-5α-ol acetyl transacylase activity (125-mM and 200-mM fractions) were combined (100 mL, ~160 mM) and diluted to 5 mM NaCl (160 mL) by ultrafiltration (DIAFLO™ YM 30 membrane, MILLIPORE™, Bedford, Mass.) and repeated dilution with 30 mM HEPES buffer (pH 7.4) containing 3 mM DTT.

Further purification was effected by high-resolution anion-exchange and hydroxyapatite chromatography run on a PHARMACIA™ FPLC system coupled to a 280-nm effluent detector. The preparation described above was applied to a preparative anion-exchange column (10×100 mm, Source 15Q, PHARMACIA™ Biotech., Piscataway, N.J.) that was previously washed with "wash buffer" (30 mM HEPES buffer (pH 7.4) containing 3 mM DTT) and 1 M NaCl, and then equilibrated with wash buffer (without NaCl). After removing unbound material, the applied protein was eluted with a linear gradient of 0 to 200 mM NaCl in equilibration buffer (215 mL total volume; 3 mL/minute) (see FIG. 3A). Fractions containing transacetylase activity (eluting at ~80 mM NaCl) were combined and diluted to 5 mM NaCl by ultrafiltration using 30 mM HEPES buffer (pH 7.4) containing 3 mM DTT as diluent, as described above. The desalted protein sample (70 mL) was loaded onto an analytical anion-exchange column (5×50 mm, Source 15Q, PHARMACIA™ Biotech., Piscataway, N.J.) that was washed and equilibrated as before. The column was developed using a shallow, linear salt gradient with elution to 200 mM NaCl (275 mL total volume, 1.5 mL/minute, 3.0 mL fractions). The taxadienol acetyl transacylase eluted at ~55–60 mM NaCl (see FIG. 3B), and the appropriate fractions were combined (15 mL), reconstituted to 45 mL in 30 mM HEPES buffer (pH 6.9) and applied to a ceramic hydroxyapatite column (10×100 mm, BIO-RAD™ Laboratories, Hercules, Calif.) that was previously washed with 200 mM sodium phosphate buffer (pH 6.9) and then equilibrated with an "equilibration buffer" (30 mM HEPES buffer (pH 6.9) containing 3 mM DTT (without sodium phosphate)). The equilibration buffer was used to desorb weakly associated material, and the bound protein was eluted by a gradient from 0 to 40 mM sodium phosphate in equilibration buffer (125 mL total volume, at 3.0 mL/minute, 3.0 mL fractions) (see FIG. 3C). The fractions containing the highest activity, eluting over 27 mL at 10 mM sodium phosphate, were combined and shown by SDS-PAGE to yield a protein of ~95% purity (a minor contaminant was present at ~35 kDa, see FIG. 3D). The level of transacylase activity was measured after each step in the isolation and purification protocol described above. The level of activity recovered is shown in Table 4.

TABLE 4

Summary of taxadien-5α-ol O-acetyl transferase purification from Taxus cells.

| | Total activity (pkat) | Total Protein (mg) | Specific Activity (pkat/mg protein) | Purification (fold) |
|---|---|---|---|---|
| Crude extract | 302 | 1230 | 0.25 | 1 |
| YM30 ultrafiltration | 136 | 98 | 1.4 | 5.6 |
| DE-52 | 122 | 69 | 1.8 | 7.2 |
| YM30 ultrafiltration | 54 | 55 | 1.0 | 4 |
| Source 15Q (10 × 100 mm) | 47 | 3 | 16 | 63 |
| YM30 ultrafiltration | 19 | 2.6 | 7.3 | 29 |
| Source 15Q (5 × 50 mm) | 13 | 0.12 | 108 | 400 |
| Hydroxyapatite | 10 | 0.05 | 200 | 800 |

D. Amino Acid Microsequencing of Taxadienol Acetyl Transacylase

The purified protein from multiple preparations as described above (>95% pure, ~100 pmol, 50 µg) was subjected to preparative SDS-PAGE (Laemmli, *Nature* 227: 680–685, 1970). The protein band at 50 kDa, corresponding to the taxadienol acetyl transacylase, was excised. Whereas treatment with V8 protease or treatment with cyanogen bromide (CNBr) failed to yield sequencable peptides, in situ proteolysis with endolysC (Caltech Sequence/Structure Analysis Facility, Pasadena, Calif.) and trypsin (Fernandez et al., *Anal. Biochem.* 218:112–118, 1994) yielded a number of peptides, as determined by HPLC, and several of these were separated, verified by mass spectrometry (Fernandez et al., *Electrophoresis* 19:1036–1045, 1998), and subjected to Edman degradative sequencing, from which five distinct and unique amino acid sequences (designated SEQ ID NOs: 29–33) were obtained (FIG. 2).

E. cDNA Library construction and Related Manipulations

A cDNA library was constructed from mRNA isolated from *T. cuspidata* suspension culture cells that had been induced to maximal paclitaxel production with methyl jasmonate for 16 hours. An optimized protocol for the isolation of total RNA from *T. cuspidata* cells was developed empirically using a buffer containing 100 mM Tri-HCl (pH 7.5), 4 M guanidine thiocyanate, 25 mM EDTA and 14 mM β-mercaptoethanol. Cells (1.5 g) were disrupted at 0–4° C. using a POLYTRON™ ultrasonicator (Kinematica AG, Switzerland; 4×15 second bursts at power setting 7), the resulting homogenate was adjusted to 2% (v/v) TRITON™ X-100 and allowed to stand 15 minutes on ice. An equal volume of 3 M sodium acetate (pH 6.0) was then added, and the mixed solution was incubated on ice for an additional 15 minutes, followed by centrifugation at 15,000 g for 30 minutes at 4° C. The resulting supernatant was mixed with 0.8 volume of isopropanol and allowed to stand on ice for 5 minutes, followed by centrifugation at 15,000 g for 30 minutes at 4° C. The resulting pellet was dissolved in 8 mL of 20 mM Tris-HCl (pH 8.0) containing 1 mM EDTA, adjusted to pH 7.0 by addition of 2 mL of 2 M NaCl in 250 mM MOPS buffer (pH 7.0), and total RNA was recovered by passing this solution over a nucleic acid isolation column (QIAGEN™, Valencia, Calif.) following the manufacturer's instructions. Poly(A)+ mRNA was then purified from total RNA by chromatography on oligo(dT) beads (OLIGOTEX™ mRNA Kit, QIAGEN™), and this material was used to construct a library using the λZAPII™ cDNA synthesis kit and GIGA-PACK™ III gold packaging kit from STRATAGENE™, La Jolla, Calif., by following the manufacturer's instructions.

Unless otherwise stated, standard methods were used for DNA manipulations and cloning (Sambrook et al. (eds.), *Molecular Cloning: A Laboratory Manual* 2nd ed., vols. 1–3, Cold Spring Harbor Laboratory Press, Cold Spring Harbor, N.Y., 1989), and for PCR amplification procedures (Innis et al., *PCR Protocols: A Guide to Methods and Applications*, Academic Press, New York, 1990). DNA was sequenced using AMPLITAQ™ (Hoffmann-La Roche INC., Nutley, N.J.) DNA polymerase and cycle sequencing (fluorescence sequencing) on an ABI PRISM™ 373 DNA Sequencer. The *E. coli* strains XL1-BLUE™ and XL1-BLUE MRF'™ (STRATAGENE™, La Jolla, Calif.) were used for routine cloning of PCR products and for cDNA library construction, respectively. *E. coli* XL1-BLUE MRF'™ cells were used for in vivo excision of purified pBLUESCRIPT™ SK from positive plaques and the excised plasmids were used to transform *E. coli* SOLR cells.

F. Degenerate Primer Design and PCR Amplification

Due to codon degeneracy, only one sequence of the five tryptic peptide fragments obtained (SEQ ID NO: 30 of FIG. 2) was suitable for PCR primer construction. Two such degenerate forward primers, designated AT-FOR1 (SEQ ID NO: 34) and AT-FOR2 (SEQ ID NO: 35), were designed based on this sequence (FIG. 4). Using the NCBI BLAST™ 2.0 database searching program (Genetics computer Group, Program Manual for the Wisconsin Package, version 9, Genetics computer Group, 575 Science Drive, Madison, Wis., 1994) to search for this sequence element among the few defined transacylases of plant origin (St. Pierre et al., *Plant J.* 14:703–713, 1998; Dudareva et al., *Plant J.* 14:297–304, 1998; and Yang et al., *Plant Mol. Biol.* 35:777–789, 1997), and the many deposited sequences of unknown function, allowed the identification of two possible sequence variants of this element (FYPFAGR (SEQ ID NO: 39) and YYPLAGR (SEQ ID NO: 40)) from which two additional degenerate forward primers, designated AT-FOR3 (SEQ ID NO: 36) and AT-FOR4 (SEQ ID NO: 37), were designed (FIG. 4). The sequences employed for this comparison are listed in Table 1. Using this range of functionally defined and undefined sequences, conserved regions were sought for the purpose of designing a degenerate reverse primer (the distinct lack of similarity of the *Taxus* sequences to genes in the database can be appreciated by reference to FIG. 6), from which one such consensus sequence element (DFGWGKP) (SEQ ID NO: 41) was noted, and was employed for the design of the reverse primer AT-REV1 (SEQ ID NO: 38) (FIG. 4). This set of four forward primers and one reverse primer incorporated a varied number of inosines, and ranged from 72- to 216-fold degeneracy. The remaining four proteolytic peptide fragment sequences (SEQ ID NO: 29, SEQ ID NO: 31, SEQ ID NO: 32, SEQ ID NO: 33 of FIG. 2) were not only less suitable for primer design, but they were not found (by NCBI BLAST™ searching) to be similar to other related sequences, thus suggesting that these represented more specific sequence elements of the *Taxus* transacetylase gene.

Each forward primer (150 µM) and the reverse primer (150 µM) were used in separate PCR reactions performed with Taq polymerase (3 U/100 µL reaction containing 2 mM $MgCl_2$) and employing the induced *T. cuspidata* cell cDNA library ($10^8$ PFU) as template under the following conditions: 94° C. for 5 minutes, 32 cycles at 94° C. for 1 minute, 40° C. for 1 minute and 74° C. for 2 minutes and, finally, 74° C. for 5 minutes. The resulting amplicons (regions amplified by the various primer combinations) were analyzed by agarose gel electrophoresis (Sambrook et al. (eds.), *Molecular Cloning: A Laboratory Manual* 2nd ed., vols. 1–3, Cold Spring Harbor Laboratory Press, Cold Spring Harbor, N.Y., 1989) and the products were extracted from the gel, ligated into pCR TOPOT7 (INVITROGEN™, Carlsbad, Calif.), and transformed into *E. coli* TOPIOF' cells (INVITROGEN™, Carlsbad, Calif.). Plasmid DNA was prepared from individual transformants and the inserts were fully sequenced.

The combination of primers AT-FOR1 (SEQ ID NO: 34) and AT-REV1 (SEQ ID NO: 38) yielded a 900-bp amplicon. Cloning and sequencing of the amplicon revealed two unique sequences designated "Probe 1" (SEQ ID NO: 1) and "Probe 2" (SEQ ID NO: 3) (Table 2). The results with the remaining primer combinations are provided in Table 2.

G. Library Screening

Four separate library-screening experiments were designed using various combinations of the radio-labeled amplicons (Probes 1–12, described supra) as probes. Use of radio-labeled Probe 1 (SEQ ID NO: 1), led to the identification of TAX1 (SEQ ID NO: 27) and TAX2 (SEQ ID NO: 25), and use of radio-labeled Probe 6 (SEQ ID NO: 11) led to the identification of TAX6 (SEQ ID NO: 44). A probe consisting of a mixture of radio-labeled Probe 10 (SEQ ID NO: 19) and Probe 12 (SEQ ID NO: 23) led to the identification of TAX10 (SEQ ID NO: 44) and TAX12 (SEQ ID NO: 55). Finally, a probe containing a mixture of radio-labeled Probes 3, 4, 5, 7, and 9 led to the identification of TAX5, TAX7, TAX9, and TAX13 (SEQ ID NOs. 49, 51, 59, and 57, respectively). Details of these individual library-screening experiments are provided below.

The identification of TAX1 (SEQ ID NO: 27) and TAX2 (SEQ ID NO: 25) was accomplished using 1 μg of Probe 1 (SEQ ID NO: 1) that had been amplified by PCR, the resulting amplicon was gel-purified, randomly labeled with [α-$^{32}$P]CTP (Feinberg and Vogelstein, *Anal. Biochem.* 137: 216–217, 1984), and used as a hybridization probe to screen membrane lifts of 5×10$^5$ plaques grown in *E. coli* XL1-BLUE MRF'™. Phage DNA was cross-linked to the nylon membranes by autoclaving on fast cycle 3–4 minutes at 120° C. After cooling, the membranes were washed 5 minutes in 2×SSC, then 5 minutes in 6×SSC (containing 0.5% SDS, 5× Denhardt's reagent, 0.5 g Ficoll (Type 400, PHARMACIA™, Piscataway, N.J.), 0.5 g polyvinylpyrrolidone (PVP-10), and 0.5 g bovine serum albumin (Fraction V, Sigma, Saint Louis, Mo.) in 100 mL total volume). Hybridization was then performed for 20 hours at 68° C. in 6×SSC, 0.5% SDS and 5× Denhardt's reagent. The nylon membranes were then washed two times for 5 minutes in 2×SSC with 0.1% SDS at 25° C., and then washed 2×30 minutes with 1×SSC and 0.1% SDS at 68° C. After washing, the membranes were exposed for 17 hours to KODAK™ (Rochester, N.Y.) XAR film at −70° C. (Sambrook et al. (eds.), *Molecular Cloning: A Laboratory Manual* 2nd ed., vols. 1–3, Cold Spring Harbor Laboratory Press, Cold Spring Harbor, N.Y., 1989).

Of the plaques exhibiting positive signals (~600 total), 60 were purified through two additional rounds of hybridization. Purified λZAP™II clones were excised in vivo as pBLUESCRIPT™ II SK(−) phagemids and transformed into *E. coli* SOLR cells (STRATAGENE™, La Jolla, Calif.). The size of each cDNA insert was determined by PCR using T3 and T7 promoter primers, and size-selected inserts (>1.5 kb) were partially sequenced from both ends to sort into unique sequence types and to acquire full-length versions of each (by further screening with a newly designed 5'-probe, if necessary).

The same basic screening protocol, as illustrated by the results provided below, can be repeated with all of the probes described in Table 2, with the goal of acquiring the full range of full-length, in-frame putative transacylase clones for test of function by expression in *E. coli*. In the case of Probe 1 (SEQ ID NO: 1), two unique full-length clones, designated TAX1 (SEQ ID NO: 27 and SEQ ID NO: 28) and TAX2 (SEQ ID NO: 25 and SEQ ID NO: 26), were isolated.

An additional transacylase, TAX6 (SEQ ID NO: 44), was identified by using 40 ng of radio-labeled Probe 6 (SEQ ID NO: 11) to screen the *T. cuspidata* library. This full-length clone was 99% identical to Probe 6 (SEQ ID NO: 11) and its deduced amino acid sequence was 99% identical to that of Probe 6 (SEQ ID NO: 12), indicating that the probe had located its cognate.

Using 40 ng of radio-labeled Probe 10 (SEQ ID NO: 19) and 40 ng of radio-labeled Probe 12 (SEQ ID NO: 23) led to the identification of the full-length transacylases TAX10 (SEQ ID NO: 53 and SEQ ID NO: 54) and TAX12 (SEQ ID NO: 55 and SEQ ID NO: 56) in separate hybridization screening experiments.

Use of a probe mixture containing about 6 ng each of Probes 3, 4, 5, 7, and 8 (SEQ ID NOs. 5, 7, 9, 13, and 15, respectively) randomly labeled with [α-$^{32}$P]CTP (Feinberg and Vogelstein, *Anal Biochem.* 137:216–217, 1984) resulted in the identification of full-length transacylases TAX5 (SEQ ID NO: 49), TAX7 (SEQ ID NO: 51), and TAX9 (SEQ ID NO: 50), which correspond to Probes 5 (SEQ ID NO: 9), 7 (SEQ ID NO: 13), and 9 (SEQ ID NO: 17), respectively. An additional full-length transacylase, TAX13 (SEQ ID NO: 57) was also identified, however, this transacylase does not correspond to any of the Probes identified in Table 2.

H. cDNA Expression in *E. coli*

Full-length insert fragments of the relevant plasmids are excised and subcloned in-frame into the expression vector pCWori+ (Barnes, *Methods Enzymol.* 272:3–14, 1996). This procedure may involve the elimination of internal restriction sites and the addition of appropriate 5'- and 3'-restriction sites for directional ligation into the expression vector using standard PCR protocols (Innis et al., *PCR Protocols: A Guide to Methods and Applications,* Academic Press: San Diego, 1990) or commercial kits such as the QUIKCHANGE™ Mutagenesis System (STRATAGENE™, La Jolla, Calif.). For example, the full-length transacylase corresponding to probe 6 (SEQ ID NO: 11) was obtained using the primer set (5'-GGGAATTCCATATG-GCAGGCTCAACAGAATTTGTGG-3' (SEQ ID NO: 46) and 3'-GTTTATACATTGATTCGGAACTAGATCTGATC-5' (SEQ ID NO: 47)) to amplify the putative full-length acetyl transferase gene and incorporate NdeI and XbaI restriction sites at the 5'- and 3'-termini, respectively, for directional ligation into vector pCWori+ (Barnes, *Methods Enzymol.* 272:3–14, 1996). All recombinant pCWori+ plasmids are confirmed by sequencing to insure that no errors have been introduced by the polymerase reactions, and are then transformed into *E. coli* JM109 by standard methods.

Isolated transformants for each full-length insert are grown to $A_{600}$=0.5 at 37° C. in 50 mL Luria-Bertani medium supplemented with 50 μg ampicillin/mL, and a 1-mL inoculum added to a large scale (100 mL) culture of Terrific Broth (6 g bacto-tryptone, DIFCO™ Laboratories, Spark, Md., 12 g yeast extract, EM Science, Cherryhill, N.J., and 2 mL glycerol in 500 mL water) containing 50 μg ampicillin/mL and thiamine HCl (320 mM) and grown at 28° C. for 24 hours. Approximately 24 hours after induction with 1 mM isopropyl β-D-thiogalactoside (IPTG), the bacterial cells are harvested by centrifugation, disrupted by sonication in assay buffer consisting of 30 mM potassium phosphate (pH 7.4), or 25 mM MOPSO (pH 7.4), followed by centrifugation to yield a soluble enzyme preparation that can be assayed for transacylase activity.

I. Enzyme Assay

A specific assay for acetyl CoA:taxa-4(20),11(12)-dien-5α-ol O-acetyl transacylase has been described previously (Walker et al., *Arch. Biochem. Biophys.* 364:273–279, 1999, herein incorporated by reference). Generally the assay for taxoid acyltransacylases involves the CoA-dependent acyl transfer from acetyl CoA (or other acyl or aroyl CoA ester) to a taxane alcohol, and the isolation and chromatographic separation of the product ester for confirmation of structure by GC-MS (or HPLC-MS) analysis. For another example of such an assay, see Menhard and Zenk, *Phytochemistry* 50:763–774, 1999.

The activity of TAX6 (SEQ ID NO: 45) was assayed under standard conditions described in Walker et al., *Arch.*

Biochem. Biophys. 364:273–279, 1999, with 10-deacetylbaccatin III (400 μM, Hauser Chemical Research Inc., Boulder, Colo.) and [2-$^3$H]acetyl CoA (0.45 μCi, 400μM (NEN, Boston, Mass.)) as co-substrates. The TAX6 (SEQ ID NO: 45) enzyme preparation yielded a single product from reversed-phase radio-HPLC analysis, with a retention time of 7.0 minutes (coincident radio and UV traces) corresponding exactly to that of authentic baccatin III (generously provided by Dr. David Bailey of Hauser Chemical Research Inc., Boulder, Colo.) (FIGS. 9A and 9B). The identity of the biosynthetic product was further verified as baccatin III by combined LC-MS (liquid chromatography-mass spectrometry) analysis (FIGS. 10A and 10B), which demonstrated the identical retention time (8.6×0.1 minute) and mass spectrum for the product and authentic standard. Finally, a sample of the biosynthetic product, purified by silica gel analytical TLC, produced a $^1$H-NMR spectrum identical to that of authentic baccatin III, confirming the enzyme as 10-deacetylbaccatin III-10-O-acetyl transferase (TAX6 (SEQ ID NO: 45)) and also confirming that the corresponding gene had been isolated.

EXAMPLES

1. Transacylase Protein and Nucleic acid Sequences

As described above, the invention provides transacylases and transacylase-specific nucleic acid sequences. With the provision herein of these transacylase sequences, the polymerase chain reaction (PCR) may now be utilized as a preferred method for identifying and producing nucleic acid sequences encoding the transacylases. For example, PCR amplification of the transacylase sequences may be accomplished either by direct PCR from a plant cDNA library or by Reverse-Transcription PCR (RT-PCR) using RNA extracted from plant cells as a template. Transacylase sequences may be amplified from plant genomic libraries, or plant genomic DNA. Methods and conditions for both direct PCR and RT-PCR are known in the art and are described in Innis et al., *PCR Protocols: A Guide to Methods and Applications,* Academic Press: San Diego, 1990.

The selection of PCR primers is made according to the portions of the cDNA (or gene) that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al., *PCR Protocols: A Guide to Methods and Applications,* Academic Press: San Diego, 1990; Sambrook et al. (eds.), *Molecular Cloning: A Laboratory Manual* 2nd ed., vols. 1–3, Cold Spring Harbor Laboratory Press, Cold Spring Harbor, N.Y., 1989; and Ausubel et al. (eds.) *Current Protocols in Molecular Biology,* Greene Publishing and Wiley-Interscience, New York (with periodic updates), 1987. By way of example, the cDNA molecules corresponding to additional transacylases may be amplified using primers directed towards regions of homology between the 5' and 3' ends of the TAX1 and TAX2 sequences. Example primers for such a reaction are:

primer 1: 5'CCT CAT CTT TCC CCC ATT GAT AAT 3' (SEQ ID NO: 42)

primer 2: 5' AAA AAG AAA ATA ATT TTG CCA TGC AAG 3' (SEQ ID NO: 43).

These primers are illustrative only; it will be appreciated by one skilled in the art that many different primers may be derived from the provided nucleic acid sequences. Re-sequencing of PCR products obtained by these amplification procedures is recommended to facilitate confirmation of the amplified sequence and to provide information on natural variation between transacylase sequences. Oligonucleotides derived from the transacylase sequence may be used in such sequencing methods.

Oligonucleotides that are derived from the transacylase sequences are encompassed within the scope of the present invention. Preferably, such oligonucleotide primers comprise a sequence of at least 10–20 consecutive nucleotides of the transacylase sequences. To enhance amplification specificity, oligonucleotide primers comprising at least 15, 20, 25, 30, 35, 40, 45 or 50 consecutive nucleotides of these sequences may also be used.

A. Transacylases in Other Plant Species

Orthologs of the transacylase genes are present in a number of other members of the *Taxus* genus. With the provision herein of the transacylase nucleic acid sequences, the cloning by standard methods of cDNAs and genes that encode transacylase orthologs in these other species is now enabled. As described above, orthologs of the disclosed transacylase genes have transacylase biological activity and are typically characterized by possession of at least 50% sequence identity counted over the full length alignment with the amino acid sequence of the disclosed transacylase sequences using the NCBI BLAST™ 2.0 (gapped blastp set to default parameters). Proteins with even greater similarity to the reference sequences will show increasing percentage identities when assessed by this method, such as at least 60%, at least 65%, at least 70%, at least 75%, at least 80%, at least 90%, or at least 95% sequence identity.

Both conventional hybridization and PCR amplification procedures may be utilized to clone sequences encoding transacylase orthologs. Common to both of these techniques is the hybridization of probes or primers that are derived from the transacylase nucleic acid sequences. Furthermore, the hybridization may occur in the context of Northern blots, Southern blots, or PCR.

Direct PCR amplification may be performed on cDNA or genomic libraries prepared from any of various plant species, or RT-PCR may be performed using mRNA extracted from plant cells using standard methods. PCR primers will comprise at least 10 consecutive nucleotides of the transacylase sequences. One of skill in the art will appreciate that sequence differences between the transacylase nucleic acid sequence and the target nucleic acid to be amplified may result in lower amplification efficiencies. To compensate for this, longer PCR primers or lower annealing temperatures may be used during the amplification cycle. Where lower annealing temperatures are used, sequential rounds of amplification using nested primer pairs may be necessary to enhance specificity.

For conventional hybridization techniques the hybridization probe is preferably conjugated with a detectable label such as a radioactive label, and the probe is preferably at least 10 nucleotides in length. As is well known in the art, increasing the length of hybridization probes tends to give enhanced specificity. The labeled probe derived from the transacylase nucleic acid sequence may be hybridized to a plant cDNA or genomic library and the hybridization signal detected using methods known in the art. The hybridizing colony or plaque (depending on the type of library used) is then purified and the cloned sequence contained in that colony or plaque is isolated and characterized.

Orthologs of the transacylases alternatively may be obtained by immunoscreening of an expression library. With the provision herein of the disclosed transacylase nucleic acid sequences, the enzymes may be expressed and purified in a heterologous expression system (e.g., E. coli) and used to raise antibodies (monoclonal or polyclonal) specific for transacylases. Antibodies may also be raised against synthetic peptides derived from the transacylase amino acid sequence presented herein. Methods of raising antibodies are well known in the art and are described generally in Harlow and Lane, *Antibodies, A Laboratory Manual*, Cold Spring Harbor Press, Cold Spring Harbor, N.Y. 1988. Such antibodies can then be used to screen an expression cDNA library produced from a plant. This screening will identify the transacylase ortholog. The selected cDNAs can be confirmed by sequencing and enzyme activity assays.

B. Paclitaxel Transacylase Variants

With the provision of the transacylase amino acid sequences (SEQ ID NOs: 2, 4, 6, 8, 10, 12, 14, 16, 18, 20, 22, 24, 26, 28, 45, 50, 52, 54, 56, and 58) and the corresponding cDNA (SEQ ID NOs: 1, 3, 5, 7, 9, 11, 13, 15, 17, 19, 21, 23, 25, 27, 44, 49, 51, 53, 55, and 57), variants of these sequences can now be created.

Variant transacylases include proteins that differ in amino acid sequence from the transacylase sequences disclosed, but that retain transacylase biological activity. Such proteins may be produced by manipulating the nucleotide sequence encoding the transacylase using standard procedures such as site-directed mutagenesis or the polymerase chain reaction. The simplest modifications involve the substitution of one or more amino acids for amino acids having similar biochemical properties. These so-called "conservative substitutions" are likely to have minimal impact on the activity of the resultant protein. Table 5 shows amino acids which may be substituted for an original amino acid in a protein and which are regarded as conservative substitutions.

TABLE 5

| Original Residue | Conservative Substitutions |
| --- | --- |
| ala | ser |
| arg | lys |
| asn | gln; his |
| asp | glu |
| cys | ser |
| gln | asn |
| glu | asp |
| gly | pro |
| his | asn; gln |
| ile | leu; val |
| leu | ile; val |
| lys | arg; gln; glu |
| met | leu; ile |
| phe | met; leu; tyr |
| ser | thr |
| thr | ser |
| trp | tyr |
| tyr | trp; phe |
| val | ile; leu |

More substantial changes in enzymatic function or other features may be obtained by selecting substitutions that are less conservative than those in Table 4, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed for transacylase derivatives by analyzing the ability of the derivative proteins to catalyse the conversion of one paclitaxel precursor to another paclitaxel precursor.

Variant transacylase cDNA or genes may be produced by standard DNA mutagenesis techniques, for example, M13 primer mutagenesis. Details of these techniques are provided in Sambrook et al. (eds.), *Molecular Cloning: A Laboratory Manual* 2nd ed., vols. 1–3, Cold Spring Harbor Laboratory Press, Cold Spring Harbor, N.Y., 1989, Ch. 15. By the use of such techniques, variants may be created that differ in minor ways from the transacylase cDNA or gene sequences, yet that still encode a protein having transacylase biological activity. DNA molecules and nucleotide sequences that are derivatives of those specifically disclosed herein and that differ from those disclosed by the deletion, addition, or substitution of nucleotides while still encoding a protein having transacylase biological activity are comprehended by this invention. In their simplest form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence in such a way that, while the nucleotide sequence is substantially altered, it nevertheless encodes a protein having an amino acid sequence identical or substantially similar to the disclosed transacylase amino acid sequences. For example, the fifteenth amino acid residue of the TAX2 (SEQ ID NO: 26) is alanine. This is encoded in the open reading frame (ORF) by the nucleotide codon triplet GCG. Because of the degeneracy of the genetic code, three other nucleotide codon triplets—GCA, GCC, and GCT—also code for alanine. Thus, the nucleotide sequence of the ORF can be changed at this position to any of these three codons without affecting the amino acid composition of the encoded protein or the characteristics of the protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences that encode the transacylase protein but that vary from the disclosed nucleic acid sequences by virtue of the degeneracy of the genetic code.

Variants of the transacylase may also be defined in terms of their sequence identity with the transacylase amino acid and nucleic acid sequences described supra. As described above, transacylases have transacylase biological activity and share at least 60% sequence identity with the disclosed transacylase sequences. Nucleic acid sequences that encode such proteins may readily be determined simply by applying the genetic code to the amino acid sequence of the transacylase, and such nucleic acid molecules may be readily produced by assembling oligonucleotides corresponding to portions of the sequence.

As previously mentioned, another method of identifying variants of the transacylases is nucleic acid hybridization. Nucleic acid molecules that are derived from the transacylase cDNA and gene sequences include molecules that hybridize under various conditions to the disclosed paclitaxel transacylase nucleic acid molecules, or fragments thereof. Generally, hybridization conditions are classified into categories, for example very high stringency, high stringency, and low stringency. The conditions for probes that are about 600 base pairs or more in length are provided below in three corresponding categories.

| Very High Stringency (detects sequences that share 90% sequence identity) | | | | |
|---|---|---|---|---|
| Hybridization in | 5× | SSC at | 65° C. | 16 hours |
| Wash twice in | 2× | SSC at | room temp. | 15 minutes each |
| Wash twice in | 0.5× | SSC at | 65° C. | 20 minutes each |
| High Stringency (detects sequences that share 80% sequence identity or greater) | | | | |
| Hybridization in | 5× | SSC at | 65° C. | 16 hours |
| Wash twice in | 2× | SSC at | room temp. | 20 minutes each |
| Wash once in | 1× | SSC at | 55° C. | 30 minutes each |
| Low Stringency (detects sequences that share greater than 50% sequence identity) | | | | |
| Hybridization in | 6× | SSC at | room temp. | 16 hours |
| Wash twice in | 3× | SSC at | room temp. (20–21° C.) | 20 minutes each |

The sequences encoding the transacylases identified through hybridization may be incorporated into transformation vectors and introduced into host cells to produce transacylase.

2. Introduction of Transacylases into Plants

After a cDNA (or gene) encoding a protein involved in the determination of a particular plant characteristic has been isolated, standard techniques may be used to express the cDNA in transgenic plants in order to modify the particular plant characteristic. The basic approach is to clone the cDNA into a transformation vector, such that the cDNA is operably linked to control sequences (e.g., a promoter) directing expression of the cDNA in plant cells. The transformation vector is then introduced into plant cells by any of various techniques (e.g., electroporation) and progeny plants containing the introduced cDNA are selected. Preferably all or part of the transformation vector stably integrates into the genome of the plant cell. That part of the transformation vector that integrates into the plant cell and that contains the introduced cDNA and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples, which serve to illustrate the knowledge in this field of technology include:

U.S. Pat. No. 5,571,706 ("Plant Virus Resistance Gene and Methods")

U.S. Pat. No. 5,677,175 ("Plant Pathogen Induced Proteins")

U.S. Pat. No. 5,510,471 ("Chimeric Gene for the Transformation of Plants")

U.S. Pat. No. 5,750,386 ("Pathogen-Resistant Transgenic Plants")

U.S. Pat. No. 5,597,945 ("Plants Genetically Enhanced for Disease Resistance")

U.S. Pat. No. 5,589,615 ("Process for the Production of Transgenic Plants with Increased Nutritional Value Via the Expression of Modified 2S Storage Albumins")

U.S. Pat. No. 5,750,871 ("Transformation and Foreign Gene Expression in *Brassica* Species")

U.S. Pat. No. 5,268,526 ("Overexpression of Phytochrome in Transgenic Plants")

U.S. Pat. No. 5,262,316 ("Genetically Transformed Pepper Plants and Methods for their Production")

U.S. Pat. No. 5,569,831 ("Transgenic Tomato Plants with Altered Polygalacturonase Isoforms")

These examples include descriptions of transformation vector selection, transformation techniques, and the construction of constructs designed to over-express the introduced cDNA. In light of the foregoing and the provision herein of the transacylase amino acid sequences and nucleic acid sequences, it is thus apparent that one of skill in the art will be able to introduce the cDNAs, or homologous or derivative forms of these molecules, into plants in order to produce plants having enhanced transacylase activity. Furthermore, the expression of one or more transacylases in plants may give rise to plants having increased production of paclitaxel and related compounds.

A. Vector construction, Choice of Promoters

A number of recombinant vectors suitable for stable transfection of plant cells or for the establishment of transgenic plants have been described including those described in Weissbach and Weissbach, *Methods for Plant Molecular Biology*, Academic Press, 1989; and Gelvin et al., *Plant and Molecular Biology Manual*, Kluwer Academic Publishers, 1990. Typically, plant-transformation vectors include one or more cloned plant genes (or cDNAs) under the transcriptional control of 5'- and 3'-regulatory sequences and a dominant selectable marker. Such plant transformation vectors typically also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and/or a polyadenylation signal.

Examples of constitutive plant promoters that may be useful for expressing the cDNA include: the cauliflower mosaic virus (CaMV) 35S promoter, which confers constitutive, high-level expression in most plant tissues (see, e.g., Odel et al., *Nature* 313:810, 1985; Dekeyser et al., *Plant Cell* 2:591, 1990; Terada and Shimamoto, *Mol. Gen. Genet.* 220:389, 1990; and Benfey and Chua, *Science* 250:959–966, 1990); the nopaline synthase promoter (An et al., *Plant Physiol.* 88:547, 1988); and the octopine synthase promoter (Fromm et al., *Plant Cell* 1:977, 1989). *Agrobacterium*-mediated transformation of *Taxus* species has been accomplished, and the resulting callus cultures have been shown to produce paclitaxel (Han et al., *Plant Science* 95:187–196, 1994). Therefore, it is likely that incorporation of one or more of the described transacylases under the influence of a strong promoter (like CaMV promoter) would increase production yields of paclitaxel and related taxoids in such transformed cells.

A variety of plant-gene promoters that are regulated in response to environmental, hormonal, chemical, and/or developmental signals also can be used for expression of the cDNA in plant cells, including promoters regulated by: (a)

heat (Callis et al., *Plant Physiol.* 88:965, 1988; Ainley, et al., *Plant Mol. Biol.* 22:13–23, 1993; and Gilmartin et al., *The Plant Cell* 4:839–949, 1992); (b) light (e.g., the pea rbcS-3A promoter, Kuhlemeier et al., *Plant Cell* 1:471, 1989, and the maize rbcS promoter, Schaffner and Sheen, *Plant Cell* 3:997, 1991); (c) hormones, such as abscisic acid (Marcotte et al., *Plant Cell* 1:969, 1989); (d) wounding (e.g., wunl, Siebertz et al., *Plant Cell* 1:961, 1989); and (e) chemicals such as methyl jasmonate or salicylic acid (Gatz et al., *Ann. Rev. Plant Physiol. Plant Mol. Biol.* 48:9–108, 1997).

Alternatively, tissue-specific (root, leaf, flower, and seed, for example) promoters (Carpenter et al., *The Plant Cell* 4:557–571, 1992; Denis et al., *Plant Physiol.* 101: 1295–1304, 1993; Opperman et al., *Science* 263:221–223, 1993; Stockhause et al., *The Plant Cell* 9:479–489, 1997; Roshal et al., *Embo. J.* 6:1155, 1987; Schemthaner et al., *Embo J.* 7:1249, 1988; and Bustos et al., *Plant Cell* 1:839, 1989) can be fused to the coding sequence to obtain a particular expression in respective organs.

Alternatively, the native transacylase gene promoters may be utilized. With the provision herein of the transacylase nucleic acid sequences, one of skill in the art will appreciate that standard molecular biology techniques can be used to determine the corresponding promoter sequences. One of skill in the art will also appreciate that less than the entire promoter sequence may be used in order to obtain effective promoter activity. The determination of whether a particular region of this sequence confers effective promoter activity may readily be ascertained by operably linking the selected sequence region to a transacylase cDNA (in conjunction with suitable 3' regulatory region, such as the NOS 3' regulatory region as discussed below) and determining whether the transacylase is expressed.

Plant-transformation vectors may also include RNA-processing signals, for example, introns, that may be positioned upstream or downstream of the ORF sequence in the transgene. In addition, the expression vectors may also include additional regulatory sequences from the 3'-untranslated region of plant genes, e.g., a 3'-terminator region to increase mRNA stability of the mRNA, such as the PI-II terminator region of potato or the octopine or nopaline synthase (NOS) 3'-terminator regions. The native transacylase gene 3'-regulatory sequence may also be employed.

Finally, as noted above, plant-transformation vectors may also include dominant selectable marker genes to allow for the ready selection of transformants. Such genes include those encoding antibiotic-resistance genes (e.g., resistance to hygromycin, kanamycin, bleomycin, G418, streptomycin or spectinomycin) and herbicide-resistance genes (e.g., phosphinothricin acetyltransacylase).

B. Arrangement of Paclitaxel Transacylase Sequence in a Vector

The particular arrangement of the transacylase sequence in the transformation vector is selected according to the type of expression of the sequence that is desired.

In most instances, enhanced transacylase activity is desired, and the transacylase ORF is operably linked to a constitutive high-level promoter such as the CaMV 35S promoter. As noted above, enhanced transacylase activity may also be achieved by introducing into a plant a transformation vector containing a variant form of the transacylase cDNA or gene, for example a form that varies from the exact nucleotide sequence of the transacylase ORF, but that encodes a protein retaining transacylase biological activity.

C. Transformation and Regeneration Techniques

Transformation and regeneration of both monocotyledonous and dicotyledonous plant cells are now routine, and the appropriate transformation technique can be determined by the practitioner. The choice of method varies with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* (AT)-mediated transformation. Typical procedures for transforming and regenerating plants are described in the patent documents listed at the beginning of this section.

D. Selection of Transformed Plants

Following transformation and regeneration of plants with the transformation vector, transformed plants can be selected using a dominant selectable marker incorporated into the transformation vector. Typically, such a marker confers antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to assess production levels of paclitaxel and related compounds.

3. Production of Recombinant Paclitaxel transacylase in Heterologous Expression Systems Various yeast strains and yeast-derived vectors are commonly used for the expression of heterologous proteins. For instance, *Pichia pastoris* expression systems, obtained from INVITROGEN™ (Carlsbad, Calif.), may be used to practice the present invention. Such systems include suitable *Pichia pastoris* strains, vectors, reagents, transformants, sequencing primers, and media. Available strains include KM71H (a prototrophic strain), SMD1168H (a prototrophic strain), and SMD1168 (a pep4 mutant strain) (INVITROGEN™ Product Catalogue, 1998, INVITROGEN™, Carlsbad Calif.).

Non-yeast eukaryotic vectors may be used with equal facility for expression of proteins encoded by modified nucleotides according to the invention. Mammalian vector/host cell systems containing genetic and cellular control elements capable of carrying out transcription, translation, and post-translational modification are well known in the art. Examples of such systems are the well-known baculovirus system, the ecdysone-inducible expression system that uses regulatory elements from *Drosophila melanogaster* to allow control of gene expression, and the sindbis viral-expression system that allows high-level expression in a variety of mammalian cell lines, all of which are available from INVITROGEN™, Carlsbad, Calif.

The cloned expression vector encoding one or more transacylases may be transformed into any of various cell types for expression of the cloned nucleotide. Many different types of cells may be used to express modified nucleic acid molecules. Examples include cells of yeasts, fungi, insects, mammals, and plants, including transformed and non-transformed cells. For instance, common mammalian cells that could be used include HeLa cells, SW-527 cells (ATCC™ deposit #7940), WISH cells (ATCC™ deposit #CCL-25), Daudi cells (ATCC™ deposit #CCL-213), Mandin-Darby bovine kidney cells (ATCC™ deposit #CCL-22) and Chinese hamster ovary (CHO) cells (ATCC™ deposit #CRL-2092). Common yeast cells include *Pichia pastoris* (ATCC™ deposit #201178) and *Saccharomyces cerevisiae* (ATCC™ deposit #46024). Insect cells include cells from *Drosophila melanogaster* (ATCC™ deposit #CRL-10191), the cotton bollworm (ATCC™ deposit #CRL-9281), and *Trichoplusia ni* egg cell homoflagellates. Fish cells that may be used include those from rainbow trout (ATCC™ deposit #CLL-55), salmon (ATCC™ deposit #CRL-1681), and zebrafish (ATCC™ deposit #CRL-2147). Amphibian cells that may be used include those of the bullfrog, *Rana castebelana* (ATCC™ deposit #CLL-41). Reptile cells that may be used include those from Russell's viper (ATCC™ deposit #CCL-140). Plant cells that could be used include *Chlamydomonas* cells (ATCC™ deposit #30485), *Arabidopsis* cells (ATCC™ deposit #54069) and tomato plant cells (ATCC™ deposit #54003). Many of these cell types are commonly used and are available from the ATCC™ as well as from commercial suppliers such as PHARMACIA™ (Uppsala, Sweden), and INVITROGEN™.

Expressed protein may be accumulated within a cell or may be secreted from the cell. Such expressed protein may then be collected and purified. This protein may then be characterized for activity and stability and may be used to practice any of the various methods according to the invention.

4. Creation of Transacylase-Specific Binding Agents

Antibodies to the transacylase enzymes, and fragments thereof, of the present invention may be useful for purification of the enzymes. The provision of the transacylase sequences allows for the production of specific antibody-based binding agents to these enzymes.

Monoclonal or polyclonal antibodies may be produced to the transacylases, portions of the transacylases, or variants thereof. Optimally, antibodies raised against epitopes on these antigens will specifically detect the enzyme. That is, antibodies raised against the transacylases would recognize and bind the transacylases, and would not substantially recognize or bind to other proteins. The determination that an antibody specifically binds to an antigen is made by any one of a number of standard immunoassay methods; for instance, Western blotting, Sambrook et al. (eds.), *Molecular Cloning: A Laboratory Manual* 2nd ed., vols. 1–3, Cold Spring Harbor Laboratory Press, Cold Spring Harbor, N.Y., 1989.

To determine that a given antibody preparation (such as a preparation produced in a mouse against TAX1 (SEQ ID NO: 28)) specifically detects the transacylase by Western blotting, total cellular protein is extracted from cells and electrophoresed on an SDS-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of 5-bromo-4-chloro-3-indolyl phosphate/nitro blue tetrazolium results in the production of a densely blue-colored compound by immuno-localized alkaline phosphatase.

Antibodies that specifically detect a transacylase will, by this technique, be shown to bind substantially only the transacylase band (having a position on the gel determined by the molecular weight of the transacylase). Non-specific binding of the antibody to other proteins may occur and may be detectable as a weaker signal on the Western blot (which can be quantified by automated radiography). The non-specific nature of this binding will be recognized by one skilled in the art by the weak signal obtained on the Western blot relative to the strong primary signal arising from the specific anti-transacylase binding.

Antibodies that specifically bind to transacylases belong to a class of molecules that are referred to herein as "specific binding agents." Specific binding agents that are capable of specifically binding to the transacylase of the present invention may include polyclonal antibodies, monoclonal antibodies and fragments of monoclonal antibodies such as Fab, $F(ab')_2$ and Fv fragments, as well as any other agent capable of specifically binding to one or more epitopes on the proteins.

Substantially pure transacylase suitable for use as an immunogen can be isolated from transfected cells, transformed cells, or from wild-type cells. Concentration of protein in the final preparation is adjusted, for example, by concentration on an AMICON™ filter device, to the level of a few micrograms per milliliter. Alternatively, peptide fragments of a transacylase may be utilized as immunogens. Such fragments may be chemically synthesized using standard methods, or may be obtained by cleavage of the whole transacylase enzyme followed by purification of the desired peptide fragments. Peptides as short as three or four amino acids in length are immunogenic when presented to an immune system in the context of a Major Histocompatibility Complex (MHC) molecule, such as MHC class I or MHC class II. Accordingly, peptides comprising at least 3 and preferably at least 4, 5, 6 or more consecutive amino acids of the disclosed transacylase amino acid sequences may be employed as immunogens for producing antibodies.

Because naturally occurring epitopes on proteins frequently comprise amino acid residues that are not adjacently arranged in the peptide when the peptide sequence is viewed as a linear molecule, it may be advantageous to utilize longer peptide fragments from the transacylase amino acid sequences for producing antibodies. Thus, for example, peptides that comprise at least 10, 15, 20, 25, or 30 consecutive amino acid residues of the amino acid sequence may be employed. Monoclonal or polyclonal antibodies to the intact transacylase or peptide fragments thereof may be prepared as described below.

A. Monoclonal Antibody Production by Hybridoma Fusion

Monoclonal antibody to any of various epitopes of the transacylase enzymes that are identified and isolated as described herein can be prepared from murine hybridomas according to the classic method of Kohler & Milstein, *Nature* 256:495, 1975, or a derivative method thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, *Enzymol.* 70:419, 1980, or a derivative method thereof. Selected positive clones can be expanded and their monoclonal antibody product harvested for use. Detailed procedures for monoclonal antibody production are described in Harlow & Lane, *Antibodies, A Laboratory Manual*, Cold Spring Harbor Laboratory, New York, 1988.

B. Polyclonal Antibody Production by Immunization

Polyclonal antiserum containing antibodies to heterogenous epitopes of a single protein can be prepared by immunizing suitable animals with the expressed protein, which can be unmodified or modified, to enhance immunogenicity. Effective polyclonal antibody production is affected by many factors related both to the antigen and the host species. For example, small molecules tend to be less immunogenic than other molecules and may require the use of carriers and an adjuvant. Also, host animals vary in response to site of inoculations and dose, with both inadequate or excessive doses of antigen resulting in low-titer antisera. Small doses (ng level) of antigen administered at multiple intradermal sites appear to be most reliable. An effective immunization protocol for rabbits can be found in Vaitukaitis et al., *J. Clin. Endocrinol. Metab.* 33:988–991, 1971.

Booster injections can be given at regular intervals, and antiserum harvested when the antibody titer thereof, as determined semi-quantitatively, for example, by double immunodiffusion in agar against known concentrations of the antigen, begins to fall. See, for example, Ouchterlony et al., Chapter 19, in Wier (ed.), *Handbook of Experimental Immunology*, Blackwell, 1973. A plateau concentration of antibody is usually in the range of 0.1 to 0.2 mg/mL of serum (about 12 µM). Affinity of the antisera for the antigen is determined by preparing competitive binding curves using conventional methods.

C. Antibodies Raised by Injection of cDNA

Antibodies may be raised against the transacylases of the present invention by subcutaneous injection of a DNA vector that expresses the enzymes in laboratory animals, such as mice. Delivery of the recombinant vector into the animals may be achieved using a hand-held form of the Biolistic system (Sanford et al., *Particulate Sci. Technol.* 5:27–37, 1987, as described by Tang et al., *Nature* (London) 356:153–154, 1992). Expression vectors suitable for this purpose may include those that express the cDNA of the enzyme under the transcriptional control of either the human β-actin promoter or the cytomegalovirus (CMV) promoter. Methods of administering naked DNA to animals in a manner resulting in expression of the DNA in the body of the animal are well known and are described, for example, in U.S. Pat. No. 5,620,896 ("DNA Vaccines Against Rotavirus Infections"); U.S. Pat. No. 5,643,578 ("Immunization by Inoculation of DNA Transcription Unit"); and U.S. Pat. No. 5,593,972 ("Genetic Immunization"), and references cited therein.

D. Antibody Fragments

Antibody fragments may be used in place of whole antibodies and may be readily expressed in prokaryotic host cells. Methods of making and using immunologically effective portions of monoclonal antibodies, also referred to as "antibody fragments," are well known and include those described in Better & Horowitz, *Methods Enzymol.* 178: 476–496, 1989; Glockshuber et al. *Biochemistry* 29:1362–1367, 1990; and U.S. Pat. No. 5,648,237 ("Expression of Functional Antibody Fragments"); U.S. Pat. No. 4,946,778 ("Single Polypeptide Chain Binding Molecules"); and U.S. Pat. No. 5,455,030 ("Immunotherapy Using Single Chain Polypeptide Binding Molecules"), and references cited therein.

5. Paclitaxel Production In Vivo

The creation of recombinant vectors and transgenic organisms expressing the vectors are important for controlling the production of transacylases. These vectors can be used to decrease transacylase production, or to increase transacylase production. A decrease in transacylase production will likely result from the inclusion of an antisense sequence or a catalytic nucleic acid sequence that targets the transacylase encoding nucleic acid sequence. Conversely, increased production of transacylase can be achieved by including at least one additional transacylase encoding sequence in the vector. These vectors can then be introduced into a host cell, thereby altering transacylase production. In the case of increased production, the resulting transacylase may be used in in vitro systems, as well as in vivo for increased production of paclitaxel, other taxoids, intermediates of the paclitaxel biosynthetic pathway, and other products.

Increased production of paclitaxel and related taxoids in vivo can be accomplished by transforming a host cell, such as one derived from the *Taxus* genus, with a vector containing one or more nucleic acid sequences encoding one or more transacylases. Furthermore, the heterologous or homologous transacylase sequences can be placed under the control of a constitutive promoter, or an inducible promoter. This will lead to the increased production of transacylase, thus eliminating any rate-limiting effect on paclitaxel production caused by the expression and/or activity level of the transacylase.

6. Paclitaxel Production In Vitro

Currently, paclitaxel is produced by a semisynthetic method described in Hezari and Croteau, *Planta Medica* 63:291–295, 1997. This method involves extracting 10-deacetyl-baccatin III, or baccatin III, intermediates in the paclitaxel biosynthetic pathway, and then finishing the production of paclitaxel using in vitro techniques. As more enzymes are identified in the paclitaxel biosynthetic pathway, it may become possible to completely synthesize paclitaxel in vitro, or at least increase the number of steps that can be performed in vitro. Hence, the transacylases of the present invention may be used to facilitate the production of paclitaxel and related taxoids in synthetic or semisynthetic methods. Accordingly, the present invention enables the production of transgenic organisms that not only produce increased levels of paclitaxel, but also transgenic organisms that produce increased levels of important intermediates, such as 10-deacetyl-baccatin III and baccatin III.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

The invention claimed is:

1. A purified protein, comprising the amino acid sequence as set forth in SEQ ID NO: 26.

2. An isolated nucleic acid molecule encoding the protein of claim 1.

3. The isolated nucleic acid molecule of claim 2, comprising the nucleic acid sequence as set forth in SEQ ID No: 25.

4. A recombinant nucleic acid molecule, comprising a promoter sequence operably linked to the nucleic acid molecule of claim 2.

5. An isolated cell transformed with the recombinant nucleic acid molecule of claim 4.

6. An isolated nucleic acid molecule that:
   (a) hybridizes under very high-stringency conditions with a nucleic acid probe, the probe comprising the nucleic acid sequence as set forth in SEQ ID NO: 25;and
   (b) encodes a protein having taxoid transacylase activity, wherein the hybridization step is performed for 20 hours at 68° C. in 6×SSC, 0.5% SDS and 5× Denhardt's reagent, washed two times for 5 minutes in 2×SSC and 0.1% SDS at 25° C., and washed 2× for 30 minutes with 1×SSC and 0.1% SDS at 68° C.

7. An isolated transacylase encoded by the nucleic acid molecule of claim 6.

8. A recombinant nucleic acid molecule, comprising a promoter sequence operably linked to the nucleic acid molecule of claim 6.

9. An isolated cell transformed with the recombinant nucleic acid molecule of claim 8.

10. An isolated nucleic acid molecule comprising a nucleic acid sequence that:
    (a) has at least 95% sequence identity with SEQ ID NO: 25;and
    (b) encodes a protein having taxoid transacylase activity.

11. A purified protein having taxoid transacylase activity, comprising an amino acid sequence selected from the group consisting of:
    (a) the amino acid sequence as set forth in SEQ ID NO: 26; and
    (b) an amino acid sequence having at least 90% sequence identity to the sequence specified in (a).

12. An isolated nucleic acid molecule encoding the protein of claim 11.

13. A recombinant nucleic acid molecule, comprising a promoter sequence operably linked to the nucleic acid molecule of claim 12.

14. An isolated cell transformed with the recombinant nucleic acid molecule of claim 13.

15. A recombinant nucleic acid molecule, comprising a promoter sequence operably linked to the nucleic acid molecule of claim 10.

16. An isolated cell transformed with the recombinant nucleic acid molecule of claim 10.

17. The purified protein of claim 11, wherein the amino acid sequence has at least 95% sequence identity to SEQ ID NO: 26.

* * * * *

UNITED STATES PATENT AND TRADEMARK OFFICE
CERTIFICATE OF CORRECTION

PATENT NO.        : 7,153,676 B1
APPLICATION NO. : 10/415197
DATED             : December 26, 2006
INVENTOR(S)       : Croteau et al.

It is certified that error appears in the above-identified patent and that said Letters Patent is hereby corrected as shown below:

In column 6, line 5, the word "endolysc" should be --endolysC--.

In column 17, line 50, the phrase "(50 kDa)" should be --(~50 kDa)--.

In column 37, line 7, the term "wun1" should be --wunI--.

Signed and Sealed this

First Day of July, 2008

JON W. DUDAS
*Director of the United States Patent and Trademark Office*

SEQUENCE LISTING

<160> NUMBER OF SEQ ID NOS: 76

<210> SEQ ID NO 1
<211> LENGTH: 920
<212> TYPE: DNA

<213> ORGANISM: Taxus cuspidata

<400> SEQUENCE: 1

| | | | | | |
|---|---|---|---|---|---|
| atgttggtct | attatcccc | ttttgctggg | cgcctcagag | agacagaaaa | tggggatctg | 60 |
| gaagtggaat | gcacagggga | gggtgctatg | tttttggaag | ccatggcaga | caatgagctg | 120 |
| tctgtgttgg | gagattttga | tgacagcaat | ccatcatttc | agcagctact | tttttcgctt | 180 |
| ccactcgata | ccaatttcaa | agacctctct | cttctggttg | ttcaggtaac | tcgttttaca | 240 |
| tgtggaggct | tgttgttgg | agtgagtttc | caccatggtg | tatgtgatgg | tcgaggagcg | 300 |
| gcccaatttc | ttaaaggttt | ggcagaaatg | gcacggggga | aggttaagct | ctcattggaa | 360 |
| ccaatatgga | atatggaact | agtgaagctt | gatgaccta | aatacctcca | attttttcac | 420 |
| tttgaattcc | tacgagcgcc | ttcaattgtt | gagaaaattg | ttcaaacata | ttttattata | 480 |
| gatttggaga | ccataaatta | tatcaaacaa | tctgttatgg | aagaatgtaa | agaattttgc | 540 |
| tcttcattcg | aagttgcatc | agcaatgact | tggatagcaa | ggacaagagc | ttttcaaatt | 600 |
| ccagaaagtg | agtacgtgaa | aattctcttc | ggaatggaca | tgaggaactc | atttaatccc | 660 |
| cctcttccaa | gcggatacta | tggtaactcc | attggtaccg | catgtgcagt | ggataatgtt | 720 |
| caagacctct | taagtggatc | tcttttgcgt | gctataatga | ttataaagaa | atcaaaggtc | 780 |
| tctttaaatg | ataatttcaa | gtcaagagct | gtggtgaagc | catctgaatt | ggatgtgaat | 840 |
| atgaatcatg | aaaacgtagt | tgcatttgct | gattggagcc | gattgggatt | tgatgaagtg | 900 |
| gattttggct | gggggaaacc | | | | | 920 |

<210> SEQ ID NO 2
<211> LENGTH: 306
<212> TYPE: PRT
<213> ORGANISM: Taxus cuspidata

<400> SEQUENCE: 2

Met Leu Val Tyr Tyr Pro Pro Phe Ala Gly Arg Leu Arg Glu Thr Glu
1               5                   10                  15

Asn Gly Asp Leu Glu Val Glu Cys Thr Gly Glu Gly Ala Met Phe Leu
            20                  25                  30

Glu Ala Met Ala Asp Asn Glu Leu Ser Val Leu Gly Asp Phe Asp Asp
        35                  40                  45

Ser Asn Pro Ser Phe Gln Gln Leu Leu Phe Ser Leu Pro Leu Asp Thr
    50                  55                  60

Asn Phe Lys Asp Leu Ser Leu Leu Val Val Gln Val Thr Arg Phe Thr
65                  70                  75                  80

Cys Gly Gly Phe Val Val Gly Val Ser Phe His His Gly Val Cys Asp
                85                  90                  95

Gly Arg Gly Ala Ala Gln Phe Leu Lys Gly Leu Ala Glu Met Ala Arg
            100                 105                 110

Gly Glu Val Lys Leu Ser Leu Glu Pro Ile Trp Asn Met Glu Leu Val
        115                 120                 125

Lys Leu Asp Asp Pro Lys Tyr Leu Gln Phe Phe His Phe Glu Phe Leu
    130                 135                 140

Arg Ala Pro Ser Ile Val Glu Lys Ile Val Gln Thr Tyr Phe Ile Ile
145                 150                 155                 160

Asp Leu Glu Thr Ile Asn Tyr Ile Lys Gln Ser Val Met Glu Glu Cys
                165                 170                 175

Lys Glu Phe Cys Ser Ser Phe Glu Val Ala Ser Ala Met Thr Trp Ile
            180                 185                 190

```
Ala Arg Thr Arg Ala Phe Gln Ile Pro Glu Ser Glu Tyr Val Lys Ile
            195                 200                 205

Leu Phe Gly Met Asp Met Arg Asn Ser Phe Asn Pro Pro Leu Pro Ser
        210                 215                 220

Gly Tyr Tyr Gly Asn Ser Ile Gly Thr Ala Cys Ala Val Asp Asn Val
225                 230                 235                 240

Gln Asp Leu Leu Ser Gly Ser Leu Leu Arg Ala Ile Met Ile Ile Lys
            245                 250                 255

Lys Ser Lys Val Ser Leu Asn Asp Asn Phe Lys Ser Arg Ala Val Val
        260                 265                 270

Lys Pro Ser Glu Leu Asp Val Asn Met Asn His Glu Asn Val Val Ala
            275                 280                 285

Phe Ala Asp Trp Ser Arg Leu Gly Phe Asp Glu Val Asp Phe Gly Trp
        290                 295                 300

Gly Lys
305
```

<210> SEQ ID NO 3
<211> LENGTH: 920
<212> TYPE: DNA
<213> ORGANISM: Taxus cuspidata

<400> SEQUENCE: 3

```
atgctggtct attatccccc ttttgctgga aggctgagaa acacagaaaa tggggaactt      60
gaagtggagt gcacagggga gggtgccgtc tttgtggaag ccatggcgga caacgacctt    120
tcagtattac aagatttcaa tgagtacgat ccatcatttc agcagctagt tttttatctt    180
ccagaggatg tcaatattga ggacctccat cttctaactg ttcaggtaac tcgttttaca    240
tgtgggggat tgttgtgggg cacaagattc caccatagtg tgtctgatgg aaaaggaatc    300
ggccagttac ttaaaggcat gggagaaatg gcaggggggg agtttaagcc ctccttagaa    360
ccaatatgga atagagaaat ggtgaagcct aagacatta tgtacctcca gtttgatcac    420
tttgatttca tacacccacc tcttaatctt gagaagtcta ttcaagcatc tatggtaata    480
agcttggaga gaataaatta tatcaaacga tgcatgatgg aagaatgcaa agaattttt     540
tctgcatttg aagttgtagt agcattgatt tggctagcaa ggacaaagtc ttttcgaatt    600
ccacccaatg agtatgtgaa aattatcttt ccaatcgaca tgaggaattc atttgactcc    660
cctcttccaa agggatacta tggtaatgct attggtaatg catgtgcaat ggataatgtc    720
aaagacctct taaatggatc tctttttatat gctctaatgc ttataaagaa atcaaagttt    780
gctttaaatg agaatttcaa atcaagaatc ttgacaaaac catctgcatt agatgcgaat    840
atgaagcatg aaaatgtagt cggatgtggc gattggagga atttgggatt ttatgaagca    900
gatttcggct ggggcaaacc                                                  920
```

<210> SEQ ID NO 4
<211> LENGTH: 306
<212> TYPE: PRT
<213> ORGANISM: Taxus cuspidata

<400> SEQUENCE: 4

```
Met Leu Val Tyr Tyr Pro Pro Phe Ala Gly Arg Leu Arg Asn Thr Glu
  1               5                  10                  15

Asn Gly Glu Leu Glu Val Glu Cys Thr Gly Glu Gly Ala Val Phe Val
             20                  25                  30
```

-continued

```
Glu Ala Met Ala Asp Asn Asp Leu Ser Val Leu Gln Asp Phe Asn Glu
         35                  40                  45

Tyr Asp Pro Ser Phe Gln Gln Leu Val Phe Tyr Leu Pro Glu Asp Val
 50                  55                  60

Asn Ile Glu Asp Leu His Leu Leu Thr Val Gln Val Thr Arg Phe Thr
 65                  70                  75                  80

Cys Gly Gly Phe Val Gly Thr Arg Phe His His Ser Val Ser Asp
                 85                  90                  95

Gly Lys Gly Ile Gly Gln Leu Leu Lys Gly Met Gly Glu Met Ala Arg
                100                 105                 110

Gly Glu Phe Lys Pro Ser Leu Glu Pro Ile Trp Asn Arg Glu Met Val
            115                 120                 125

Lys Pro Glu Asp Ile Met Tyr Leu Gln Phe Asp His Phe Asp Phe Ile
130                 135                 140

His Pro Pro Leu Asn Leu Glu Lys Ser Ile Gln Ala Ser Met Val Ile
145                 150                 155                 160

Ser Leu Glu Arg Ile Asn Tyr Ile Lys Arg Cys Met Met Glu Glu Cys
                165                 170                 175

Lys Glu Phe Phe Ser Ala Phe Glu Val Val Ala Leu Ile Trp Leu
            180                 185                 190

Ala Arg Thr Lys Ser Phe Arg Ile Pro Pro Asn Glu Tyr Val Lys Ile
            195                 200                 205

Ile Phe Pro Ile Asp Met Arg Asn Ser Phe Asp Ser Pro Leu Pro Lys
210                 215                 220

Gly Tyr Tyr Gly Asn Ala Ile Gly Asn Ala Cys Ala Met Asp Asn Val
225                 230                 235                 240

Lys Asp Leu Leu Asn Gly Ser Leu Leu Tyr Ala Leu Met Leu Ile Lys
                245                 250                 255

Lys Ser Lys Phe Ala Leu Asn Glu Asn Phe Lys Ser Arg Ile Leu Thr
            260                 265                 270

Lys Pro Ser Ala Leu Asp Ala Asn Met Lys His Glu Asn Val Val Gly
            275                 280                 285

Cys Gly Asp Trp Arg Asn Leu Gly Phe Tyr Glu Ala Asp Phe Gly Trp
290                 295                 300

Gly Lys
305
```

<210> SEQ ID NO 5
<211> LENGTH: 903
<212> TYPE: DNA
<213> ORGANISM: Taxus cuspidata

<400> SEQUENCE: 5

```
ttttatccgt tgcggggcg gctcagaaat aaagaaaatg gggaacttga agtggagtgc     60
acagggcagg gtgttctgtt tctggaagcc atggccgaca cgaccttc agtcttaaca    120
gatctggatg actacaagcc atcgtttcag cagttgattt tttctctacc acaggataca    180
gatattgagg atctccatct cttgattgtt caggtaactc gttttacatg tgggggtttt    240
gttgtgggag cgaatgtgta tagtagtgta tgtgatgcaa aaggatttgg ccaatttctt    300
caaggtatgg cagagatggc gagaggagag gttaagccct cgattgaacc gatatggaat    360
agagaactgg tgaagccaga acattgtatg cccttccgga tgagtcatct tcaaattata    420
cacgcacctc tgatcgagga gaaatttgtt caaacatctc ttgttataaa ctttgagata    480
ataaatcata tcagacaacg gatcatggaa gaatgtaaag aaagtttctc ttcatttgaa    540
```

```
attgtagcag cattggtttg gctagcaaag ataaaggctt ttcaaattcc acatagtgag    600
aatgtgaagc ttcttttgc aatggactta aggagatcat ttaatccccc tcttccacat     660
ggatactatg gcaatgcctt cggtattgca tgtgcaatgg ataatgtcca tgacttta      720 agtggatctc ttttgcgcgc tataatgatc ataaagaaat caagttctc tttacacaaa     780 gaactcaact caaaaaccgt gatgagcccg tctgtagtag atgtcaatac gaagttcgaa    840
gatgtagttt caattagtga ctggaggcag tctatatatt atgaagtgga ctttggttgg    900
ggc                                                                  903
```

```
<210> SEQ ID NO 6
<211> LENGTH: 301
<212> TYPE: PRT
<213> ORGANISM: Taxus cuspidata

<400> SEQUENCE: 6

Phe Tyr Pro Phe Ala Gly Arg Leu Arg Asn Lys Glu Asn Gly Glu Leu
 1               5                  10                  15

Glu Val Glu Cys Thr Gly Gln Gly Val Leu Phe Leu Glu Ala Met Ala
                20                  25                  30

Asp Ser Asp Leu Ser Val Leu Thr Asp Leu Asp Asp Tyr Lys Pro Ser
            35                  40                  45

Phe Gln Gln Leu Ile Phe Ser Leu Pro Gln Asp Thr Asp Ile Glu Asp
        50                  55                  60

Leu His Leu Leu Ile Val Gln Val Thr Arg Phe Thr Cys Gly Gly Phe
 65                  70                  75                  80

Val Val Gly Ala Asn Val Tyr Ser Ser Val Cys Asp Ala Lys Gly Phe
                85                  90                  95

Gly Gln Phe Leu Gln Gly Met Ala Glu Met Ala Arg Gly Glu Val Lys
            100                 105                 110

Pro Ser Ile Glu Pro Ile Trp Asn Arg Glu Leu Val Lys Pro Glu His
        115                 120                 125

Cys Met Pro Phe Arg Met Ser His Leu Gln Ile Ile His Ala Pro Leu
    130                 135                 140

Ile Glu Glu Lys Phe Val Gln Thr Ser Leu Val Ile Asn Phe Glu Ile
145                 150                 155                 160

Ile Asn His Ile Arg Gln Arg Ile Met Glu Glu Cys Lys Glu Ser Phe
                165                 170                 175

Ser Ser Phe Glu Ile Val Ala Ala Leu Val Trp Leu Ala Lys Ile Lys
            180                 185                 190

Ala Phe Gln Ile Pro His Ser Glu Asn Val Lys Leu Leu Phe Ala Met
        195                 200                 205

Asp Leu Arg Arg Ser Phe Asn Pro Leu Pro His Gly Tyr Tyr Gly
    210                 215                 220

Asn Ala Phe Gly Ile Ala Cys Ala Met Asp Asn Val His Asp Leu Leu
225                 230                 235                 240

Ser Gly Ser Leu Leu Arg Ala Ile Met Ile Lys Lys Ser Lys Phe
                245                 250                 255

Ser Leu His Lys Glu Leu Asn Ser Lys Thr Val Met Ser Pro Ser Val
            260                 265                 270

Val Asp Val Asn Thr Lys Phe Glu Asp Val Val Ser Ile Ser Asp Trp
        275                 280                 285

Arg Gln Ser Ile Tyr Tyr Glu Val Asp Phe Gly Trp Gly
    290                 295                 300
```

<210> SEQ ID NO 7
<211> LENGTH: 908
<212> TYPE: DNA
<213> ORGANISM: Taxus cuspidata

<400> SEQUENCE: 7

```
ttctacccgt tgcagggcg gctcagaaat aaagaaaatg gggaacttga agtggagtgc      60
acagggcagg gtgttctgtt tctggaagcc atggctgaca gcgacgtttc agtcttaaca     120
gatctggaag actacaatcc atcgtttcag cagttgcttt tttctctacc acaggataca     180
gatattgagg acctccatct cttgattgtt caggtgactc actttacatg tggggatttt     240
gttgtgggag cgaatgttta tggtagtgta tgtgacggaa aaggatttgg ccagtttctt     300
caaggtatgg cggagatggc gagaggagag gttaagccct cgattgaacc gatatggaat     360
agagaactgg tgaagccaga agatttaatg ccctccacg tggatcatct tcgaattata     420
cacacacctc taatcgagga gaaatttgtt caaacatctc ttgttataaa ctttgagata     480
ataaatcata tcagacgatg catcatggaa gaatgtaaag aaagtttctc ttcattcgaa     540
attgtagcag cattggtttg gctagcaaag ataaaagctt ttcgaattcc acatagtgag     600
aatgtgaaga ttctctttgc aatggacgtg aggagatcat ttaagccccc tcttccaaag     660
ggatactatg gcaatgccta tggtattgca tgtgcaatgg ataatgtcca ggatcttcta     720
agtggatctc ttttgcatgc tataatgatc ataaagaaat caaagttctc tttacacaaa     780
aaaatcaact caaaaactgt gatgagcccg tctccattag acgtcaatat gaagtttgaa     840
aatgtagttt caattactga ttggaggcat tctaaatatt atgaagtaga cttcgggtgg     900
ggtaaacc                                                              908
```

<210> SEQ ID NO 8
<211> LENGTH: 302
<212> TYPE: PRT
<213> ORGANISM: Taxus cuspidata

<400> SEQUENCE: 8

```
Phe Tyr Pro Phe Ala Gly Arg Leu Arg Asn Lys Glu Asn Gly Glu Leu
 1               5                  10                  15

Glu Val Glu Cys Thr Gly Gln Gly Val Leu Phe Leu Glu Ala Met Ala
            20                  25                  30

Asp Ser Asp Val Ser Val Leu Thr Asp Leu Glu Asp Tyr Asn Pro Ser
        35                  40                  45

Phe Gln Gln Leu Leu Phe Ser Leu Pro Gln Asp Thr Asp Ile Glu Asp
    50                  55                  60

Leu His Leu Leu Ile Val Gln Val Thr His Phe Thr Cys Gly Asp Phe
65                  70                  75                  80

Val Val Gly Ala Asn Val Tyr Gly Ser Val Cys Asp Gly Lys Gly Phe
                85                  90                  95

Gly Gln Phe Leu Gln Gly Met Ala Glu Met Ala Arg Gly Glu Val Lys
            100                 105                 110

Pro Ser Ile Glu Pro Ile Trp Asn Arg Glu Leu Val Lys Pro Glu Asp
        115                 120                 125

Leu Met Ala Leu His Val Asp His Leu Arg Ile Ile His Thr Pro Leu
    130                 135                 140

Ile Glu Glu Lys Phe Val Gln Thr Ser Leu Val Ile Asn Phe Glu Ile
145                 150                 155                 160
```

-continued

```
Ile Asn His Ile Arg Arg Cys Ile Met Glu Glu Cys Lys Glu Ser Phe
            165                 170                 175
Ser Ser Phe Glu Ile Val Ala Ala Leu Val Trp Leu Ala Lys Ile Lys
            180                 185                 190
Ala Phe Arg Ile Pro His Ser Glu Asn Val Lys Ile Leu Phe Ala Met
            195                 200                 205
Asp Val Arg Arg Ser Phe Lys Pro Pro Leu Pro Lys Gly Tyr Tyr Gly
            210                 215                 220
Asn Ala Tyr Gly Ile Ala Cys Ala Met Asp Asn Val Gln Asp Leu Leu
225                 230                 235                 240
Ser Gly Ser Leu Leu His Ala Ile Met Ile Ile Lys Lys Ser Lys Phe
            245                 250                 255
Ser Leu His Lys Lys Ile Asn Ser Lys Thr Val Met Ser Pro Ser Pro
            260                 265                 270
Leu Asp Val Asn Met Lys Phe Glu Asn Val Val Ser Ile Thr Asp Trp
            275                 280                 285
Arg His Ser Lys Tyr Tyr Glu Val Asp Phe Gly Trp Gly Lys
            290                 295                 300
```

<210> SEQ ID NO 9
<211> LENGTH: 1297
<212> TYPE: DNA
<213> ORGANISM: Taxus cuspidata

<400> SEQUENCE: 9

```
atgggcaggt tcaatgtaga tatgattgag cgagtgatcg ggcgccatgc cttcaatcgc      60
ccaaaaatat cctgcacctc tcccccatta acaaaaact agaggactaa ccaacatatt     120
atcagtctac aatgcctcca gagagtttct gtttctgcag atcctgcaaa acaattcga     180
gaggctcctc caaggtgctg gtttattatc cccttttgc tggaaggctg agaaaccaga     240
aaatggggat cttgaagtgg agtgcacagg ggagggtgcc gtcttgtgga agccatggcg     300
gacaacgacc tttcagtatt acaagatttc aatggtacga tccatcattt cagcagctag     360
ttttaatct tcgagaggat gtcatattga ggacctccat cttctaactg ttcaggtaac     420
tcgttttaca tgggaggatt tgttgtgggc acaagattcc accatagtgt atctgatgga     480
aaggaatcgg ccagttactt aaaggcatgg gagagatggc aagggggag ttaagccctc     540
gttagaacca atatggaata gagaaatggt gaagcctgag acattatgta cctccagttt     600
gatcactttg atttcataca cccacctcta atcttgagaa gtctattcaa gcatctatgg     660
taataagctt tgagagataa attatatcaa acgatgcatg atggaagaat gcaagaatt     720
ttttcgcat ttgaagttgt agtagcattg atttggctgg caaggacaaa gtctttcgaa     780
ttccacccaa tgagtatgtg aaaattatct ttccaatcga catgggaatt catttgactc     840
ccctcttcca aagggatact atggtaatgc tatggtaatg catgtgcaat ggataatgtc     900
aaagacctct taaatggatc tctttatatg ctctaatgct tataaagaaa tcaaagtttg     960
ctttaaatga gatttcaaat caagaatctt gacaaaacca tctacattag atgcgaatat    1020
aagcatgaaa atgtagtcgg atgtggcgat tggaggaatt tgggattttt gaagcagatt    1080
ttggatgggg aaatgcagtg aatgtaagcc ccatgcagaa caaagagagc atgaattagc    1140
tatgcaaaat tattttcttt ttctccgtca gctaagaaca tgattgatgg aatcaagata    1200
ctaatgttca tgcctgatca atggtgaaac cattcaaaat tgaaatggaa gtcacaataa    1260
acaaaatgtg gctaaaatat gtaactctaa gttataa                             1297
```

<210> SEQ ID NO 10
<211> LENGTH: 302
<212> TYPE: PRT
<213> ORGANISM: Taxus cuspidata

<400> SEQUENCE: 10

```
Phe Tyr Pro Phe Ala Gly Arg Leu Arg Lys Lys Glu Asp Gly Asp Ile
  1               5                  10                  15
Glu Val Val Cys Thr Glu Gln Gly Ala Leu Phe Val Glu Ala Val Ala
             20                  25                  30
Asp Asn Asp Leu Ser Ala Val Arg Asp Leu Asp Glu Tyr Asn Pro Leu
         35                  40                  45
Phe Arg Gln Leu Gln Ser Thr Leu Pro Leu Asp Thr Asp Cys Lys Asp
     50                  55                  60
Leu His Leu Met Thr Val Gln Val Thr Arg Phe Thr Cys Gly Gly Phe
 65                  70                  75                  80
Val Met Gly Thr Ser Val His Gln Ser Ile Cys Asp Gly Asn Gly Leu
                 85                  90                  95
Gly Gln Phe Phe Lys Ser Met Ala Glu Met Val Arg Gly Glu Val Lys
            100                 105                 110
Pro Ser Ile Glu Pro Val Trp Asn Arg Glu Leu Val Lys Pro Glu Asp
        115                 120                 125
Tyr Ile His Leu Gln Leu Tyr Ile Gly Glu Phe Ile Arg Pro Pro Leu
    130                 135                 140
Ala Phe Glu Lys Val Gly Gln Thr Ser Leu Ile Ile Ser Phe Glu Lys
145                 150                 155                 160
Ile Asn His Ile Lys Arg Cys Ile Met Glu Glu Ser Lys Glu Ser Phe
                165                 170                 175
Ser Ser Phe Glu Ile Val Thr Ala Leu Val Trp Leu Ala Arg Thr Arg
            180                 185                 190
Ala Phe Gln Ile Pro His Asn Glu Asp Val Thr Leu Leu Leu Ala Met
        195                 200                 205
Asp Ala Arg Arg Ser Phe Asp Pro Pro Ile Pro Lys Gly Tyr Tyr Gly
    210                 215                 220
Asn Val Ile Gly Thr Ala Cys Ala Thr Asn Asn Val His Asn Leu Leu
225                 230                 235                 240
Ser Gly Ser Leu Leu His Ala Leu Thr Ile Ile Lys Lys Ser Met Ser
                245                 250                 255
Ser Phe Tyr Glu Asn Ile Thr Ser Arg Val Leu Val Asn Pro Ser Thr
            260                 265                 270
Leu Asp Leu Ser Met Lys Tyr Glu Asn Val Val Thr Ile Ser Asp Trp
        275                 280                 285
Arg Arg Leu Gly Tyr Asn Glu Val Asp Phe Gly Trp Gly Lys
    290                 295                 300
```

<210> SEQ ID NO 11
<211> LENGTH: 911
<212> TYPE: DNA
<213> ORGANISM: Taxus cuspidata

<400> SEQUENCE: 11

```
ttctatccgt tcgcggggcg tctcaggaaa aagaaaatg  gagatcttga agtggagtgc      60
acaggggagg gtgctctgtt tgtggaagcc atggctgaca ctgacctctc agtcttagga     120
gatttggatg actacagtcc ttcacttgag caactacttt tttgtcttcc gcctgataca     180
```

-continued

| | |
|---|---|
| gatattgagg acatccatcc tctggtggtt caggtaactc gttttacatg tggaggtttt | 240 |
| gttgtagggg tgagtttctg ccatggtata tgtgatggac taggagcagg ccagtttctt | 300 |
| atagccatgg gagagatggc aaggggagag attaagccct cctcggagcc aatatggaag | 360 |
| agagaattgc tgaagccgga agacccttta taccggttcc agtattatca ctttcaattg | 420 |
| atttgcccgc cttcaacatt cgggaaaata gttcaaggat ctcttgttat aacctctgag | 480 |
| acaataaatt gtatcaaaca atgccttagg gaagaaagta aagaattttg ctctgcgttc | 540 |
| gaagttgtat ctgcattggc ttggatagca aggacaaggg ctcttcaaat tccacatagt | 600 |
| gagaatgtga agcttatttt tgcaatggac atgagaaaat tatttaatcc accactttcg | 660 |
| aagggatact acgtaatttt tgttggtacc gtatgtgcaa tggataatgt caaggaccta | 720 |
| ttaagtggat ctcttttgcg tgttgtaagg attataaaga aagcaaaggt ctctttaaat | 780 |
| gagcatttca cgtcaacaat cgtgacaccc cgttctggat cagatgagag tatcaattat | 840 |
| gaaaacatag ttggatttgg tgatcgaagg cgattgggat tgatgaagt agactttggc | 900 |
| tggggcaaac c | 911 |

<210> SEQ ID NO 12
<211> LENGTH: 303
<212> TYPE: PRT
<213> ORGANISM: Taxus cuspidata

<400> SEQUENCE: 12

Phe Tyr Pro Phe Ala Gly Arg Leu Arg Lys Lys Glu Asn Gly Asp Leu
1               5                   10                  15

Glu Val Glu Cys Thr Gly Glu Gly Ala Leu Phe Val Glu Ala Met Ala
            20                  25                  30

Asp Thr Asp Leu Ser Val Leu Gly Asp Leu Asp Asp Tyr Ser Pro Ser
        35                  40                  45

Leu Glu Gln Leu Leu Phe Cys Leu Pro Pro Asp Thr Asp Ile Glu Asp
    50                  55                  60

Ile His Pro Leu Val Val Gln Val Thr Arg Phe Thr Cys Gly Gly Phe
65                  70                  75                  80

Val Val Gly Val Ser Phe Cys His Gly Ile Cys Asp Gly Leu Gly Ala
                85                  90                  95

Gly Gln Phe Leu Ile Ala Met Gly Glu Met Ala Arg Gly Glu Ile Lys
            100                 105                 110

Pro Ser Ser Glu Pro Ile Trp Lys Arg Glu Leu Leu Lys Pro Glu Asp
        115                 120                 125

Pro Leu Tyr Arg Phe Gln Tyr Tyr His Phe Gln Leu Ile Cys Pro Pro
    130                 135                 140

Ser Thr Phe Gly Lys Ile Val Gln Gly Ser Leu Val Ile Thr Ser Glu
145                 150                 155                 160

Thr Ile Asn Cys Ile Lys Gln Cys Leu Arg Glu Glu Ser Lys Glu Phe
                165                 170                 175

Cys Ser Ala Phe Glu Val Val Ser Ala Leu Ala Trp Ile Ala Arg Thr
            180                 185                 190

Arg Ala Leu Gln Ile Pro His Ser Glu Asn Val Lys Leu Ile Phe Ala
        195                 200                 205

Met Asp Met Arg Lys Leu Phe Asn Pro Pro Leu Ser Lys Gly Tyr Tyr
    210                 215                 220

Gly Asn Phe Val Gly Thr Val Cys Ala Met Asp Asn Val Lys Asp Leu
225                 230                 235                 240

```
Leu Ser Gly Ser Leu Leu Arg Val Val Arg Ile Ile Lys Lys Ala Lys
                245                 250                 255

Val Ser Leu Asn Glu His Phe Thr Ser Thr Ile Val Thr Pro Arg Ser
            260                 265                 270

Gly Ser Asp Glu Ser Ile Asn Tyr Glu Asn Ile Val Gly Phe Gly Asp
        275                 280                 285

Arg Arg Arg Leu Gly Phe Asp Glu Val Asp Phe Gly Trp Gly Lys
    290                 295                 300

<210> SEQ ID NO 13
<211> LENGTH: 968
<212> TYPE: DNA
<213> ORGANISM: Taxus cuspidata

<400> SEQUENCE: 13
ttttatccgt tgcaggccg gctcagaaat aaagaaaatg gggaacttga agtggagtgc      60
acagggcagg gtgttctgtt tctggaagcc atggctgaca gcgacctttc agtcttaaca     120
gatctcgata actacaatcc atcgtttcag cagttgattt tttctctacc acaggataca     180
gatattgagg acctccatct cttgattgtt caggtaactc gttttacatg tgggggtttt     240
gttgtgggag cgaatgtgta tggtagtaca tgcgatgcaa aaggatttgg ccagtttctt     300
caaggtatgg cagagatggc gagaggagag gttaagccct cgattgaacc gatatggaat     360
aagagaactg gtgaagctag aagagaggtt aagccctcga ttgaaccgat atggaataag     420
agaactggtg aagctagaag attgtatgcc ctttccggga tgagtcatct tcaaattata     480
cacgcacctg taattgagga gaaatttgtt caaacatctc ttgttataaa ctttgagata     540
ataaatcata tcagacgacg catcatggaa gaatgcaaag aaagtttatc ttcatttgaa     600
attgtagcag cattggtttg gctagcaaag ataaaggctt tcaaattcc acatagtgag      660
aatgtgaagc ttcttttgc aatggacttg aggagatcat ttaatccccc tcttccacat      720
ggatactatg gcaatgcctt tggtattgca tgtgcaatgg ataatgtcca tgaccttcta     780
agtggatctc ttttgcgcac tataatgatc ataaagaaat caagttctc tttacacaaa     840
gaactcaact caaaaccgt gatgagctcg tctgtagtag atgtcaatac gaagtttgaa     900
gatgtagttt caattagtga ttggaggcat tctatatatt atgaagtgga ctttggctgg     960
ggtaaacc                                                              968

<210> SEQ ID NO 14
<211> LENGTH: 322
<212> TYPE: PRT
<213> ORGANISM: Taxus cuspidata

<400> SEQUENCE: 14

Phe Tyr Pro Phe Ala Gly Arg Leu Arg Asn Lys Glu Asn Gly Glu Leu
  1               5                  10                  15

Glu Val Glu Cys Thr Gly Gln Gly Val Leu Phe Leu Glu Ala Met Ala
             20                  25                  30

Asp Ser Asp Leu Ser Val Leu Thr Asp Leu Asp Asn Tyr Asn Pro Ser
         35                  40                  45

Phe Gln Gln Leu Ile Phe Ser Leu Pro Gln Asp Thr Asp Ile Glu Asp
     50                  55                  60

Leu His Leu Leu Ile Val Gln Val Thr Arg Phe Thr Cys Gly Gly Phe
 65                  70                  75                  80

Val Val Gly Ala Asn Val Tyr Gly Ser Thr Cys Asp Ala Lys Gly Phe
                 85                  90                  95
```

```
Gly Gln Phe Leu Gln Gly Met Ala Glu Met Ala Arg Gly Glu Val Lys
                100                 105                 110

Pro Ser Ile Glu Pro Ile Trp Asn Lys Arg Thr Gly Glu Ala Arg Arg
        115                 120                 125

Glu Val Lys Pro Ser Ile Glu Pro Ile Trp Asn Lys Arg Thr Gly Glu
    130                 135                 140

Ala Arg Arg Leu Tyr Ala Leu Ser Gly Met Ser His Leu Gln Ile Ile
145                 150                 155                 160

His Ala Pro Val Ile Glu Glu Lys Phe Val Gln Thr Ser Leu Val Ile
                165                 170                 175

Asn Phe Glu Ile Ile Asn His Ile Arg Arg Ile Met Glu Glu Cys
            180                 185                 190

Lys Glu Ser Leu Ser Ser Phe Glu Ile Val Ala Ala Leu Val Trp Leu
        195                 200                 205

Ala Lys Ile Lys Ala Phe Gln Ile Pro His Ser Glu Asn Val Lys Leu
    210                 215                 220

Leu Phe Ala Met Asp Leu Arg Arg Ser Phe Asn Pro Pro Leu Pro His
225                 230                 235                 240

Gly Tyr Tyr Gly Asn Ala Phe Gly Ile Ala Cys Ala Met Asp Asn Val
                245                 250                 255

His Asp Leu Leu Ser Gly Ser Leu Leu Arg Thr Ile Met Ile Ile Lys
            260                 265                 270

Lys Ser Lys Phe Ser Leu His Lys Glu Leu Asn Ser Lys Thr Val Met
        275                 280                 285

Ser Ser Ser Val Val Asp Val Asn Thr Lys Phe Glu Asp Val Val Ser
    290                 295                 300

Ile Ser Asp Trp Arg His Ser Ile Tyr Tyr Glu Val Asp Phe Gly Trp
305                 310                 315                 320

Gly Lys

<210> SEQ ID NO 15
<211> LENGTH: 908
<212> TYPE: DNA
<213> ORGANISM: Taxus cuspidata

<400> SEQUENCE: 15
ttttacccgt tgcggggcg tctcagaaat aaagaaaatg gggatctgga agtggagtgt    60
acaggggagg gtgctgtgtt tgtggaagcc atggcggaca cagatctttc ttccttggga   120
gatttggatg ctcataatcc ttcatttcac cagctttctg tttcacctcc agtggattct   180
gatattgagg gcctccatct tgcagctctt caggtaactc gttttacatg tggggttttt   240
gttctaggag taagtttgaa ccaaagtgtg tgcgatggaa aaggattggg aaattttctt   300
aaaggtgtgg cagagatggt gaggggaaaa gataagccct caattgaacc agtatgggaat  360 agagaaatgg taaagtttga agactataca cgcctccaat tttatcacca tgaattcata   420
caaccacctt taatagatga gaaaattgtt caaaaatctc ttgttataaa cttggagaca   480
ataaatatta tcaaacgatg tattatggaa gaatatacaa aatttttctc tacattcgaa   540
atcgtagcag caatggtttg gctagcaaga acaaaagctt tcaaaattcc acatagtgaa   600
aatgcagagc ttctctttac aatggatatg agggaatcat ttaatccccc tcttccaaag   660
ggatactatg gtaatgttat gggtatagta tgtgcattgg ataatgtcaa acacctatta   720
agtggatcta ttttgcgtgc tgcaatggtt atacagaaat caaggttttt ctttacagag   780
```

```
aatttccggt taagatctat gacacaacca tctgcattga ctgtgaagat caagcacaaa    840
aatgtagttg catgtagtga ttggaggcaa tatggatatg atgaagtgga cttcggctgg    900
ggtaaacc                                                              908
```

<210> SEQ ID NO 16
<211> LENGTH: 302
<212> TYPE: PRT
<213> ORGANISM: Taxus cuspidata

<400> SEQUENCE: 16

```
Phe Tyr Pro Phe Ala Gly Arg Leu Arg Asn Lys Glu Asn Gly Asp Leu
  1               5                  10                  15

Glu Val Glu Cys Thr Gly Glu Gly Ala Val Phe Val Glu Ala Met Ala
             20                  25                  30

Asp Thr Asp Leu Ser Ser Leu Gly Asp Leu Asp Ala His Asn Pro Ser
         35                  40                  45

Phe His Gln Leu Ser Val Ser Pro Pro Val Asp Ser Asp Ile Glu Gly
     50                  55                  60

Leu His Leu Ala Ala Leu Gln Val Thr Arg Phe Thr Cys Gly Gly Phe
 65                  70                  75                  80

Val Leu Gly Val Ser Leu Asn Gln Ser Val Cys Asp Gly Lys Gly Leu
                 85                  90                  95

Gly Asn Phe Leu Lys Gly Val Ala Glu Met Val Arg Gly Lys Asp Lys
            100                 105                 110

Pro Ser Ile Glu Pro Val Trp Asn Arg Glu Met Val Lys Phe Glu Asp
        115                 120                 125

Tyr Thr Arg Leu Gln Phe Tyr His His Glu Phe Ile Gln Pro Pro Leu
    130                 135                 140

Ile Asp Glu Lys Ile Val Gln Lys Ser Leu Val Ile Asn Leu Glu Thr
145                 150                 155                 160

Ile Asn Ile Ile Lys Arg Cys Ile Met Glu Glu Tyr Thr Lys Phe Phe
                165                 170                 175

Ser Thr Phe Glu Ile Val Ala Ala Met Val Trp Leu Ala Arg Thr Lys
            180                 185                 190

Ala Phe Lys Ile Pro His Ser Glu Asn Ala Glu Leu Leu Phe Thr Met
        195                 200                 205

Asp Met Arg Glu Ser Phe Asn Pro Pro Leu Pro Lys Gly Tyr Tyr Gly
    210                 215                 220

Asn Val Met Gly Ile Val Cys Ala Leu Asp Asn Val Lys His Leu Leu
225                 230                 235                 240

Ser Gly Ser Ile Leu Arg Ala Ala Met Val Ile Gln Lys Ser Arg Phe
                245                 250                 255

Phe Phe Thr Glu Asn Phe Arg Leu Arg Ser Met Thr Gln Pro Ser Ala
            260                 265                 270

Leu Thr Val Lys Ile Lys His Lys Asn Val Val Ala Cys Ser Asp Trp
        275                 280                 285

Arg Gln Tyr Gly Tyr Asp Glu Val Asp Phe Gly Trp Gly Lys
    290                 295                 300
```

<210> SEQ ID NO 17
<211> LENGTH: 908
<212> TYPE: DNA
<213> ORGANISM: Taxus cuspidata

<400> SEQUENCE: 17

-continued

```
ttctacccgt tgcggggcg gatgagaaac aaaggagatg gggaactgga agtggattgc    60
acggggaag gtgctctgtt tgtagaagcc atggcggacg acaacctttc agtgttggga    120
ggttttgatt accacaatcc agcatttggg aagctacttt actcactacc actggatacc    180
cctattcacg acctccatcc tctggttgtt caggtaactc gttttacctg cgggggttt    240
gttgtgggat taagtttgga ccatactata tgtgatggac gtggtgcagg tcaatttctt    300
aaagccctag cagaratggc gaggggagag gctaagccct cattggaacc aatatggaat    360
agagagttgt tgaagcccga agaccttata cgcctgcaat tttatcactt gaatcgatg    420
cgtccacctc caatagttga agaaatggtt caatcatcta ttattataaa tgctgagaca    480
ataagtaata tsaaacaata cattatggaa gaatgtaaag aatcttgttc tgcatttgat    540
gtcgtaggag gattggcttg gctagccagg acaaaggctt tcaaattcc acatacagag    600
aatgtgatgg ttatttttgc agtggatgcg aggagatcat tgatccacc acttccaaag    660
ggttactatg gtaatgtcgt tggtaatgca tgtgcattgg ataatgttca agacctctta    720
aatggatctc tttttgcgtgc tacaatgatt ataaagaaat caaaggtatc tttaaaagag    780
aatataaggg caaaaacttt gacgatacca tctatagtag atgtgaatgt gaaacatgaa    840
aacatagttg gattaggcga tttgagacga ctgggattta atgaagtgga cttcggctgg    900
ggsaagcc                                                                908
```

<210> SEQ ID NO 18
<211> LENGTH: 302
<212> TYPE: PRT
<213> ORGANISM: Taxus cuspidata
<220> FEATURE:
<221> NAME/KEY: variation
<222> LOCATION: (164)
<223> OTHER INFORMATION: Xaa is any amino acid.

<400> SEQUENCE: 18

```
Phe Tyr Pro Phe Ala Gly Arg Met Arg Asn Lys Gly Asp Gly Glu Leu
  1               5                  10                  15

Glu Val Asp Cys Thr Gly Glu Gly Ala Leu Phe Val Glu Ala Met Ala
             20                  25                  30

Asp Asp Asn Leu Ser Val Leu Gly Gly Phe Asp Tyr His Asn Pro Ala
         35                  40                  45

Phe Gly Lys Leu Leu Tyr Ser Leu Pro Leu Asp Thr Pro Ile His Asp
     50                  55                  60

Leu His Pro Leu Val Val Gln Val Thr Arg Phe Thr Cys Gly Gly Phe
 65                  70                  75                  80

Val Val Gly Leu Ser Leu Asp His Thr Ile Cys Asp Gly Arg Gly Ala
                 85                  90                  95

Gly Gln Phe Leu Lys Ala Leu Ala Glu Met Ala Arg Gly Glu Ala Lys
            100                 105                 110

Pro Ser Leu Glu Pro Ile Met Asn Arg Glu Leu Leu Lys Pro Glu Asp
        115                 120                 125

Leu Ile Arg Leu Gln Phe Tyr His Phe Glu Ser Met Arg Pro Pro Pro
    130                 135                 140

Ile Val Glu Glu Met Val Gln Ser Ser Ile Ile Ile Asn Ala Glu Thr
145                 150                 155                 160

Ile Ser Asn Xaa Lys Gln Tyr Ile Met Glu Glu Cys Lys Glu Ser Cys
                165                 170                 175

Ser Ala Phe Asp Val Val Gly Gly Leu Ala Met Leu Ala Arg Thr Lys
            180                 185                 190
```

```
Ala Phe Gln Ile Pro His Thr Glu Asn Val Met Val Ile Phe Ala Val
            195                 200                 205

Asp Ala Arg Arg Ser Phe Asp Pro Pro Leu Pro Lys Gly Tyr Tyr Gly
    210                 215                 220

Asn Val Val Gly Asn Ala Cys Ala Leu Asp Asn Val Gln Asp Leu Leu
225                 230                 235                 240

Asn Gly Ser Leu Leu Arg Ala Thr Met Ile Ile Lys Lys Ser Lys Val
                245                 250                 255

Ser Leu Lys Glu Asn Ile Arg Ala Lys Thr Leu Thr Ile Pro Ser Ile
            260                 265                 270

Val Asp Val Asn Val Lys His Glu Asn Ile Val Gly Leu Gly Asp Leu
        275                 280                 285

Arg Arg Leu Gly Phe Asn Glu Val Asp Phe Gly Trp Gly Lys
    290                 295                 300
```

<210> SEQ ID NO 19
<211> LENGTH: 911
<212> TYPE: DNA
<213> ORGANISM: Taxus cuspidata

<400> SEQUENCE: 19

```
tactacccgc tggcaggacg gctcagaagt aaagaaattg gggaacttga agtggagtgc     60
acagggatg  gtgctctgtt tgtggaagcc atggtggaag acaccatttc agtcttacga   120
gatctggatg acctcaatcc atcatttcag cagttagttt tttggcatcc attggacact   180
gctattgagg atcttcatct tgtgattgtt caggtaacac gttttacatg tgggggcatt   240
gccgttggag tgactttgcc ccatagtgta tgtgatggac gtggagcacc ccagtttgtt   300
acagcactgg cagaaatggc gaggggagag gttaagccct attagaaccc aatatggaat   360
agagaattgt tgaaccctga agaccctcta catctccagt taaatcaatt tgattcgata   420
tgcccacctc caatgctcga ggaattgggt caagcttctt ttgttataaa tgttgacacc   480
atagaatata tgaaacaatg tgttatggag gaatgtaatg attttgttc gtcctttgaa    540
gtagtggcag cattggtttg gatagcaagg acaaaggctc ttcaaattcc acatactgag   600
aatgtgaagc ttctctttgc gatggatttg aggaaattat ttaatccccc acttccaaat   660
ggatattatg gtaatgccat tggtactgca atgcaatgg  ataatgtcca agacctctta   720
aatggatctc ttttgcgtgc tataatgatt ataaaaaaag caaaggctga tttaaaagat   780
aattattcga ggtcaagggt agttacaaac ccaaattcat tagatgtgaa caagaaatcc   840
aacaacattc ttgcattgag tgactggagg cggttgggat tttatgaagc cgattttggc   900
tggggcaagc c                                                        911
```

<210> SEQ ID NO 20
<211> LENGTH: 303
<212> TYPE: PRT
<213> ORGANISM: Taxus cuspidata

<400> SEQUENCE: 20

```
Tyr Tyr Pro Leu Ala Gly Arg Leu Arg Ser Lys Glu Ile Gly Glu Leu
  1               5                  10                  15

Glu Val Glu Cys Thr Gly Asp Gly Ala Leu Phe Val Glu Ala Met Val
             20                  25                  30

Glu Asp Thr Ile Ser Val Leu Arg Asp Leu Asp Asp Leu Asn Pro Ser
         35                  40                  45
```

-continued

```
            Phe Gln Gln Leu Val Phe Trp His Pro Leu Asp Thr Ala Ile Glu Asp
                 50                  55                  60

Leu His Leu Val Ile Val Gln Val Thr Arg Phe Thr Cys Gly Gly Ile
             65                  70                  75                  80

Ala Val Gly Val Thr Leu Pro His Ser Val Cys Asp Gly Arg Gly Ala
                             85                  90                  95

Pro Gln Phe Val Thr Ala Leu Ala Glu Met Ala Arg Gly Glu Val Lys
                        100                 105                 110

Pro Leu Leu Glu Pro Ile Trp Asn Arg Glu Leu Leu Asn Pro Glu Asp
                    115                 120                 125

Pro Leu His Leu Gln Leu Asn Gln Phe Asp Ser Ile Cys Pro Pro Pro
                130                 135                 140

Met Leu Glu Glu Leu Gly Gln Ala Ser Phe Val Ile Asn Val Asp Thr
            145                 150                 155                 160

Ile Glu Tyr Met Lys Gln Cys Val Met Glu Glu Cys Asn Asp Phe Cys
                            165                 170                 175

Ser Ser Phe Glu Val Val Ala Ala Leu Val Trp Ile Ala Arg Thr Lys
                        180                 185                 190

Ala Leu Gln Ile Pro His Thr Glu Asn Val Lys Leu Leu Phe Ala Met
                    195                 200                 205

Asp Leu Arg Lys Leu Phe Asn Pro Pro Leu Pro Asn Gly Tyr Tyr Gly
                210                 215                 220

Asn Ala Ile Gly Thr Ala Tyr Ala Met Asp Asn Val Gln Asp Leu Leu
            225                 230                 235                 240

Asn Gly Ser Leu Leu Arg Ala Ile Met Ile Ile Lys Lys Ala Lys Ala
                            245                 250                 255

Asp Leu Lys Asp Asn Tyr Ser Arg Ser Arg Val Val Thr Asn Pro Asn
                        260                 265                 270

Ser Leu Asp Val Asn Lys Lys Ser Asn Asn Ile Leu Ala Leu Ser Asp
                    275                 280                 285

Trp Arg Arg Leu Gly Phe Tyr Glu Ala Asp Phe Gly Trp Gly Lys
                290                 295                 300
```

<210> SEQ ID NO 21
<211> LENGTH: 911
<212> TYPE: DNA
<213> ORGANISM: Taxus cuspidata

<400> SEQUENCE: 21

```
tactaccogc tggcaggacg gctcagaagt aaagaaattg ggaacttga agtggagtgc      60 acagggatg gtgctctgtt tgtggaagcc atggtggaag acaccatttc agtcttacga     120 gatctggat acctcaatcc atcatttcag cagttagttt tttggcatcc attggacact     180
gctattgagg atcttcatct tgtgattgtt caggtaacac gttttacatg tgggggcatt     240
gccgttggag tgactttgcc ccatagtgta tgtgatggac gtggagcacc ccagtttgtt     300
acagcactgg cagaaatggc gaggggagag gttaagccct tattagaacc aatatggaat     360
agagaattgt tgaaccctga agaccctcta catctccagt taaatcaatt tgattcgata     420
tgcccacctc caatgctcga ggaattgggt caagcttctt ttgttataaa tgttgacacc     480
atagaatata tgaaacaatg tgttatggag gaatgtaatg attttttgttc gtcctttgaa     540 gtagtggcag cattggtttg gatagcaagg acaaaggctc ttcaaattcc acatactgag     600
aatgtgaagc ttctcttttgc gatggatttg aggaaaattat ttaatccccc acttccaaat     660
ggatattatg gtaatgccat tggtactgca tatgcaatgg ataatgtcca agacctctta     720
```

```
aatggatctc ttttgcgtgc tataatgatt ataaaaaaag caaaggctga tttaaaagat    780
aattattcga ggtcaagggt agttacaaac ccaaattcat tagatgtgaa caagaaatcc    840
aacaacattc ttgcattgag tgactggagg cggttgggat tttatgaagc cgattttggc    900
tggggcaagc c                                                         911
```

<210> SEQ ID NO 22
<211> LENGTH: 306
<212> TYPE: PRT
<213> ORGANISM: Taxus cuspidata

<400> SEQUENCE: 22

```
Tyr Tyr Pro Leu Ala Gly Arg Leu Glu Thr Cys Asp Gly Met Val Tyr
 1               5                  10                  15

Ile Asp Cys Asn Asp Lys Gly Ala Glu Phe Ile Glu Ala Tyr Ala Ser
                20                  25                  30

Pro Glu Leu Gly Val Ala Glu Ile Met Ala Asp Ser Phe Pro His Gln
            35                  40                  45

Ile Phe Ala Phe Asn Gly Val Leu Asn Ile Asp Gly His Phe Met Pro
        50                  55                  60

Leu Leu Ala Val Gln Ala Thr Lys Leu Lys Asp Gly Ile Ala Leu Ala
 65                  70                  75                  80

Ile Thr Val Asn His Ala Val Ala Asp Ala Thr Ser Val Trp His Phe
                85                  90                  95

Ile Ser Ser Trp Ala Gln Leu Cys Lys Glu Pro Ser Asn Ile Pro Leu
            100                 105                 110

Leu Pro Leu His Thr Arg Cys Phe Thr Thr Ile Ser Pro Ile Lys Leu
        115                 120                 125

Asp Ile Gln Tyr Ser Ser Thr Thr Thr Glu Ser Ile Asp Asn Phe Phe
    130                 135                 140

Pro Pro Pro Leu Thr Glu Lys Ile Phe His Phe Ser Gly Lys Thr Ile
145                 150                 155                 160

Ser Arg Leu Lys Glu Glu Ala Met Glu Ala Cys Lys Asp Lys Ser Ile
                165                 170                 175

Ser Ile Ser Ser Phe Gln Ala Leu Cys Gly His Leu Trp Gln Ser Ile
            180                 185                 190

Thr Arg Ala Arg Gly Leu Ser Pro Ser Glu Pro Thr Thr Ile Lys Ile
        195                 200                 205

Ala Val Asn Cys Arg Pro Arg Ile Val Pro Leu Pro Asn Ser Tyr
    210                 215                 220

Phe Gly Asn Ala Val Gln Val Val Asp Val Thr Met Thr Thr Glu Glu
225                 230                 235                 240

Leu Leu Gly Asn Gly Gly Ala Cys Ala Ala Leu Ile Leu His Gln Lys
                245                 250                 255

Ile Ser Ala His Gln Asp Thr Gln Ile Arg Ala Glu Leu Asp Lys Pro
            260                 265                 270

Pro Lys Ile Val His Thr Asn Asn Leu Ile Pro Cys Asn Ile Ile Ala
        275                 280                 285

Met Ala Gly Ser Pro Arg Phe Pro Ile Tyr Asn Asn Asp Phe Gly Trp
    290                 295                 300

Gly Lys
305
```

<210> SEQ ID NO 23

-continued

```
<211> LENGTH: 908
<212> TYPE: DNA
<213> ORGANISM: Taxus cuspidata

<400> SEQUENCE: 23
ttctacccgt tcgcggggcg gatcagacag aaagaaaatg aggaactgga agtggagtgc      60 acagggagg gtgcactgtt tgtggaagcc gtggtggaca atgatctttc agtcttgaaa     120
gatttggatg cccaaaatgc atcttatgag cagttgctct tttcgcttcc gcccaataca     180
caggttcagg acctccatcc tctgattctt caggtaactc gttttaaatg tggaggtttt     240
gttgtgggag ttggtttcca ccatagtata tgtgacgcac gaggaggaac tcaatttctt     300
ctaggcctag cagatatggc aaggggagag actaagcctt tagtggaacc agtatggaat     360
agagaactga taaaccctga agatctaatg caccctccaat ttcataagtt tggtttgata     420
cgccaacctc taaaacttga tgaaatttgt caagcatctt ttactataaa ctcaaagata     480
ataaattaca tcaaacaatg tgttatagaa gaatgtaatg aaattttctc tgcatttgaa     540
gttgtagtag cattaacttg gatagcaagg acaaaggctt ttcaaattcc acatagtgag     600
aatgtgatga tgctctttgg aatggacgcg aggaaatatt ttaatccccc acttccaaag     660
ggatattatg gtaatgccat tggtacttca tgtgtaattg aaaatgtaca agacctctta     720
aatggatctc tttcgcgtgc tgtaatgatc acaaagaaat caaaggtccc tttaattgag     780
aatttaaggt caagaattgt ggcgaaccaa tctggagtag atgaggaaat taagcatgaa     840
aacgtagttg gatttggaga ttggaggcga ttgggatttc atgaagtgga cttcggctgg     900
ggcaagcc                                                              908

<210> SEQ ID NO 24
<211> LENGTH: 302
<212> TYPE: PRT
<213> ORGANISM: Taxus cuspidata

<400> SEQUENCE: 24

Phe Tyr Pro Phe Ala Gly Arg Ile Arg Gln Lys Glu Asn Glu Glu Leu
 1               5                  10                  15

Glu Val Glu Cys Thr Gly Glu Gly Ala Leu Phe Val Glu Ala Val Val
            20                  25                  30

Asp Asn Asp Leu Ser Val Leu Lys Asp Leu Asp Ala Gln Asn Ala Ser
        35                  40                  45

Tyr Glu Gln Leu Leu Phe Ser Leu Pro Pro Asn Thr Gln Val Gln Asp
    50                  55                  60

Leu His Pro Leu Ile Leu Gln Val Thr Arg Phe Lys Cys Gly Gly Phe
65                  70                  75                  80

Val Val Gly Val Gly Phe His His Ser Ile Cys Asp Ala Arg Gly Gly
                85                  90                  95

Thr Gln Phe Leu Leu Gly Leu Ala Asp Met Ala Arg Gly Glu Thr Lys
            100                 105                 110

Pro Leu Val Glu Pro Val Trp Asn Arg Glu Leu Ile Asn Pro Glu Asp
        115                 120                 125

Leu Met His Leu Gln Phe His Lys Phe Gly Leu Ile Arg Gln Pro Leu
    130                 135                 140

Lys Leu Asp Glu Ile Cys Gln Ala Ser Phe Thr Ile Asn Ser Lys Ile
145                 150                 155                 160

Ile Asn Tyr Ile Lys Gln Cys Val Ile Glu Glu Cys Asn Glu Ile Phe
                165                 170                 175
```

```
Ser Ala Phe Glu Val Val Ala Leu Thr Trp Ile Ala Arg Thr Lys
            180                 185                 190

Ala Phe Gln Ile Pro His Ser Glu Asn Val Met Met Leu Phe Gly Met
        195                 200                 205

Asp Ala Arg Lys Tyr Phe Asn Pro Pro Leu Pro Lys Gly Tyr Tyr Gly
        210                 215                 220

Asn Ala Ile Gly Thr Ser Cys Val Ile Glu Asn Val Gln Asp Leu Leu
225                 230                 235                 240

Asn Gly Ser Leu Ser Arg Ala Val Met Ile Thr Lys Lys Ser Lys Val
            245                 250                 255

Pro Leu Ile Glu Asn Leu Arg Ser Arg Ile Val Ala Asn Gln Ser Gly
        260                 265                 270

Val Asp Glu Glu Ile Lys His Glu Asn Val Val Gly Phe Gly Asp Trp
        275                 280                 285

Arg Arg Leu Gly Phe His Glu Val Asp Phe Gly Trp Gly Lys
        290                 295                 300

<210> SEQ ID NO 25
<211> LENGTH: 1320
<212> TYPE: DNA
<213> ORGANISM: Taxus cuspidata

<400> SEQUENCE: 25
atgggcaggt tcaatgtaga tatgattgag cgagtgatcg tggcgccatg ccttcaatcg      60
cccaaaaata tcctgcacct ctcccccatt gacaacaaaa ctagaggact aaccaacata     120
ttatcagtct acaatgcctc ccagagagtt tctgtttctg cagatcctgc aaaaacaatt     180
cgagaggctc tctccaaggt gctggtttat tatccccctt ttgctggaag gctgagaaac     240
acagaaaatg gggatcttga agtggagtgc acaggggagg gtgccgtctt tgtggaagcc     300
atggcggaca cgaccttttc agtattacaa gatttcaatg agtacgatcc atcatttcag     360
cagctagttt ttaatcttcg agaggatgtc aatattgagg acctccatct tctaactgtt     420
caggtaactc gttttacatg tggaggattt gttgtgggca aagattcca ccatagtgta      480
tctgatggaa aaggaatcgg ccagttactt aaaggcatgg gagagatggc aagggggag      540
tttaagcccct cgttagaacc aatatggaat agagaaatgg tgaagcctga agacattatg     600
tacctccagt ttgatcactt tgatttcata cacccacctc ttaatcttga aagtctatt      660
caagcatcta tggtaataag ctttgagaga ataaattata tcaaacgatg catgatggaa     720
gaatgcaaag aattttttc tgcatttgaa gttgtagtag cattgatttg gctggcaagg     780
acaaagtctt ttcgaattcc acccaatgag tatgtgaaaa ttatctttcc aatcgacatg     840
aggaattcat ttgactcccc tcttccaaag ggatactatg gtaatgctat tggtaatgca     900
tgtgcaatgg ataatgtcaa agacctctta aatggatctc ttttatatgc tctaatgctt     960
ataaagaaat caagtttgc tttaaatgag aatttcaaat caagaatctt gacaaaacca    1020
tctacattag atgcgaatat gaagcatgaa atgtagtcg gatgtggcga ttggaggaat    1080
ttgggattt atgaagcaga ttttggatgg ggaaatgcag tgaatgtaag ccccatgcag    1140
caacaaagag agcatgaatt agctatgcaa aattattttc ttttctccg atcagctaag    1200
aacatgattg atgaatcaa gatactaatg ttcatgcctg catcaatggt gaaaccattc    1260
aaaattgaaa tggaagtcac aataaacaaa tatgtggcta aatatgtaa ctctaagtta    1320

<210> SEQ ID NO 26
<211> LENGTH: 440
```

```
<212> TYPE: PRT
<213> ORGANISM: Taxus cuspidata

<400> SEQUENCE: 26

Met Gly Arg Phe Asn Val Asp Met Ile Glu Arg Val Ile Val Ala Pro
 1               5                  10                  15

Cys Leu Gln Ser Pro Lys Asn Ile Leu His Leu Ser Pro Ile Asp Asn
                20                  25                  30

Lys Thr Arg Gly Leu Thr Asn Ile Leu Ser Val Tyr Asn Ala Ser Gln
            35                  40                  45

Arg Val Ser Val Ser Ala Asp Pro Ala Lys Thr Ile Arg Glu Ala Leu
        50                  55                  60

Ser Lys Val Leu Val Tyr Tyr Pro Pro Phe Ala Gly Arg Leu Arg Asn
65                  70                  75                  80

Thr Glu Asn Gly Asp Leu Glu Val Glu Cys Thr Gly Glu Gly Ala Val
                85                  90                  95

Phe Val Glu Ala Met Ala Asp Asn Asp Leu Ser Val Leu Gln Asp Phe
                100                 105                 110

Asn Glu Tyr Asp Pro Ser Phe Gln Gln Leu Val Phe Asn Leu Arg Glu
            115                 120                 125

Asp Val Asn Ile Glu Asp Leu His Leu Leu Thr Val Gln Val Thr Arg
        130                 135                 140

Phe Thr Cys Gly Gly Phe Val Val Gly Thr Arg Phe His His Ser Val
145                 150                 155                 160

Ser Asp Gly Lys Gly Ile Gly Gln Leu Leu Lys Gly Met Gly Glu Met
                165                 170                 175

Ala Arg Gly Glu Phe Lys Pro Ser Leu Glu Pro Ile Trp Asn Arg Glu
                180                 185                 190

Met Val Lys Pro Glu Asp Ile Met Tyr Leu Gln Phe Asp His Phe Asp
            195                 200                 205

Phe Ile His Pro Pro Leu Asn Leu Glu Lys Ser Ile Gln Ala Ser Met
        210                 215                 220

Val Ile Ser Phe Glu Arg Ile Asn Tyr Ile Lys Arg Cys Met Met Glu
225                 230                 235                 240

Glu Cys Lys Glu Phe Phe Ser Ala Phe Glu Val Val Ala Leu Ile
                245                 250                 255

Trp Leu Ala Arg Thr Lys Ser Phe Arg Ile Pro Pro Asn Glu Tyr Val
                260                 265                 270

Lys Ile Ile Phe Pro Ile Asp Met Arg Asn Ser Phe Asp Ser Pro Leu
            275                 280                 285

Pro Lys Gly Tyr Tyr Gly Asn Ala Ile Gly Asn Ala Cys Ala Met Asp
        290                 295                 300

Asn Val Lys Asp Leu Leu Asn Gly Ser Leu Leu Tyr Ala Leu Met Leu
305                 310                 315                 320

Ile Lys Lys Ser Lys Phe Ala Leu Asn Glu Asn Phe Lys Ser Arg Ile
                325                 330                 335

Leu Thr Lys Pro Ser Thr Leu Asp Ala Asn Met Lys His Glu Asn Val
                340                 345                 350

Val Gly Cys Gly Asp Trp Arg Asn Leu Gly Phe Tyr Glu Ala Asp Phe
            355                 360                 365

Gly Trp Gly Asn Ala Val Asn Val Ser Pro Met Gln Gln Gln Arg Glu
        370                 375                 380

His Glu Leu Ala Met Gln Asn Tyr Phe Leu Phe Leu Arg Ser Ala Lys
385                 390                 395                 400
```

-continued

Asn Met Ile Asp Gly Ile Lys Ile Leu Met Phe Met Pro Ala Ser Met
            405                 410                 415

Val Lys Pro Phe Lys Ile Glu Met Glu Val Thr Ile Asn Lys Tyr Val
        420                 425                 430

Ala Lys Ile Cys Asn Ser Lys Leu
        435                 440

<210> SEQ ID NO 27
<211> LENGTH: 1317
<212> TYPE: DNA
<213> ORGANISM: Taxus cuspidata

<400> SEQUENCE: 27

```
atggagaaga cagatttaca cgtaaatctg attgagaaag tgatggttgg gccatccccg      60
cctctgccca aaaccaccct gcaactctcc tccatagaca acctgccagg ggtaagagga     120
agcattttca atgccttgtt aatttacaat gcctctccct ctcccaccat gatctctgca     180
gatcctgcaa aaccaattag agaagctctc gccaagatcc tggtttatta tccccctttt     240
gctgggcgcc tcagagagac agaaaatggg gatctggaag tggaatgcac aggggagggt     300
gctatgtttt tggaagccat ggcagacaat gagctgtctg tgttgggaga ttttgatgac     360
agcaatccat catttcagca gctacttttt tcgcttccac tcgataccaa tttcaaagac     420
ctctctcttc tggttgttca ggtaactcgt tttacatgtg gaggctttgt tgttggagtg     480
agtttccacc atggtgtatg tgatggtcga ggagcggccc aatttcttaa aggtttggca     540
gagatggcac ggggagaggt taagctctca ttggaaccaa tatggaatag ggaactagtg     600
aagcttgatg accctaaata ccttcaattt tttcactttg aattcctacg agcgccttca     660
attgttgaga aaattgttca acatattttt attatagatt ttgagaccat aaattatatc     720
aaacaatctg ttatggaaga atgtaaagaa ttttgctctt cattcgaagt tgcatcagca     780
atgacttgga tagcaaggac aagagctttt caaattccag aaagtgagta cgtgaaaatt     840
ctcttcggaa tggacatgag gaactcattt aatccccctc ttccaagcgg atactatggt     900
aactccattg gtaccgcatg tgcagtggat aatgttcaag acctcttaag tggatctctt     960
ttgcgtgcta taatgattat aaagaaatca aggtctctt taaatgataa tttcaagtca    1020
agagctgtgg tgaagccatc tgaattggat gtgaatatga atcatgaaaa cgtagttgca    1080
tttgctgatt ggagccgatt gggatttgat gaagtggatt ttggttgggg gaatgcggtg    1140
agtgtaagcc ctgtgcaaca acagtctgcg ttagcaatgc aaaattattt tcttttccta    1200
aaaccttcca gaacaagcc cgatggaatc aaaatattaa tgtttctgcc cctatcaaaa    1260
atgaagtcat tcaaaattga aatggaagcc atgatgaaaa aatatgtggc taaagta       1317
```

<210> SEQ ID NO 28
<211> LENGTH: 439
<212> TYPE: PRT
<213> ORGANISM: Artificial Sequence
<220> FEATURE:
<223> OTHER INFORMATION: Description of Artificial Sequence: clone TAX1

<400> SEQUENCE: 28

Met Glu Lys Thr Asp Leu His Val Asn Leu Ile Glu Lys Val Met Val
 1               5                  10                  15

Gly Pro Ser Pro Leu Pro Lys Thr Thr Leu Gln Leu Ser Ser Ile
            20                  25                  30

Asp Asn Leu Pro Gly Val Arg Gly Ser Ile Phe Asn Ala Leu Leu Ile

-continued

```
                35                  40                  45
Tyr Asn Ala Ser Pro Ser Pro Thr Met Ile Ser Ala Asp Pro Ala Lys
             50                  55                  60

Pro Ile Arg Glu Ala Leu Ala Lys Ile Leu Val Tyr Tyr Pro Pro Phe
 65                  70                  75                  80

Ala Gly Arg Leu Arg Glu Thr Glu Asn Gly Asp Leu Glu Val Glu Cys
                 85                  90                  95

Thr Gly Glu Gly Ala Met Phe Leu Glu Ala Met Ala Asp Asn Glu Leu
            100                 105                 110

Ser Val Leu Gly Asp Phe Asp Asp Ser Asn Pro Ser Phe Gln Gln Leu
            115                 120                 125

Leu Phe Ser Leu Pro Leu Asp Thr Asn Phe Lys Asp Leu Ser Leu Leu
130                 135                 140

Val Val Gln Val Thr Arg Phe Thr Cys Gly Gly Phe Val Val Gly Val
145                 150                 155                 160

Ser Phe His His Gly Val Cys Asp Gly Arg Gly Ala Ala Gln Phe Leu
                165                 170                 175

Lys Gly Leu Ala Glu Met Ala Arg Gly Glu Val Lys Leu Ser Leu Glu
            180                 185                 190

Pro Ile Trp Asn Arg Glu Leu Val Lys Leu Asp Asp Pro Lys Tyr Leu
            195                 200                 205

Gln Phe Phe His Phe Glu Phe Leu Arg Ala Pro Ser Ile Val Glu Lys
            210                 215                 220

Ile Val Gln Thr Tyr Phe Ile Ile Asp Phe Glu Thr Ile Asn Tyr Ile
225                 230                 235                 240

Lys Gln Ser Val Met Glu Glu Cys Lys Glu Phe Cys Ser Ser Phe Glu
                245                 250                 255

Val Ala Ser Ala Met Thr Trp Ile Ala Arg Thr Arg Ala Phe Gln Ile
            260                 265                 270

Pro Glu Ser Glu Tyr Val Lys Ile Leu Phe Gly Met Asp Met Arg Asn
            275                 280                 285

Ser Phe Asn Pro Pro Leu Pro Ser Gly Tyr Tyr Gly Asn Ser Ile Gly
290                 295                 300

Thr Ala Cys Ala Val Asp Asn Val Gln Asp Leu Leu Ser Gly Ser Leu
305                 310                 315                 320

Leu Arg Ala Ile Met Ile Lys Lys Ser Lys Val Ser Leu Asn Asp
                325                 330                 335

Asn Phe Lys Ser Arg Ala Val Lys Pro Ser Glu Leu Asp Val Asn
            340                 345                 350

Met Asn His Glu Asn Val Ala Phe Ala Asp Trp Ser Arg Leu Gly
            355                 360                 365

Phe Asp Glu Val Asp Phe Gly Trp Gly Asn Ala Val Ser Val Ser Pro
            370                 375                 380

Val Gln Gln Gln Ser Ala Leu Ala Met Gln Asn Tyr Phe Leu Phe Leu
385                 390                 395                 400

Lys Pro Ser Lys Asn Lys Pro Asp Gly Ile Lys Ile Leu Met Phe Leu
                405                 410                 415

Pro Leu Ser Lys Met Lys Ser Phe Lys Ile Glu Met Glu Ala Met Met
            420                 425                 430

Lys Lys Tyr Val Ala Lys Val
            435
```

<210> SEQ ID NO 29

```
<211> LENGTH: 15
<212> TYPE: PRT
<213> ORGANISM: Artificial Sequence
<220> FEATURE:
<223> OTHER INFORMATION: Description of Artificial Sequence: proteolytic
      fragment

<400> SEQUENCE: 29

Thr Thr Leu Gln Leu Ser Ser Ile Asp Asn Leu Pro Gly Val Arg
 1               5                  10                  15

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence:proteolytic
      fragment

<400> SEQUENCE: 30

Ile Leu Val Tyr Tyr Pro Pro Phe Ala Gly Arg
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence:proteolytic
      fragment

<400> SEQUENCE: 31

Phe Thr Cys Gly Gly Phe Val Val Gly Val Ser Phe
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:proteolytic
      fragment

<400> SEQUENCE: 32

Lys Gly Leu Ala Glu Ile Ala Arg Gly Glu Val Lys
 1               5                  10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence:proteolytic
      fragment

<400> SEQUENCE: 33

Asn Leu Pro Asn Asp Thr Asn Pro Ser Ser Gly Tyr Tyr Gly Asn
 1               5                  10                  15

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: variation
<222> LOCATION: (3)
<223> OTHER INFORMATION: N = I
```

```
<220> FEATURE:
<221> NAME/KEY: variation
<222> LOCATION: (4)
<223> OTHER INFORMATION: N = c or t
<220> FEATURE:
<221> NAME/KEY: variation
<222> LOCATION: (6)
<223> OTHER INFORMATION: n= i
<220> FEATURE:
<221> NAME/KEY: variation
<222> LOCATION: (9)
<223> OTHER INFORMATION: n = I, C, or A
<220> FEATURE:
<221> NAME/KEY: variation
<222> LOCATION: (12)
<223> OTHER INFORMATION: N= t or c
<220> FEATURE:
<221> NAME/KEY: variation
<222> LOCATION: (15)
<223> OTHER INFORMATION: N = t or c
<220> FEATURE:
<221> NAME/KEY: variation
<222> LOCATION: (18)
<223> OTHER INFORMATION: n = I, c, A

<400> SEQUENCE: 34
atnntngtnt antanccncc                                          20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: variation
<222> LOCATION: (3)
<223> OTHER INFORMATION: N = T or C
<220> FEATURE:
<221> NAME/KEY: variation
<222> LOCATION: (6)
<223> OTHER INFORMATION: N = T, or C
<220> FEATURE:
<221> NAME/KEY: variation
<222> LOCATION: (9)
<223> OTHER INFORMATION: N = I, C, or A
<220> FEATURE:
<221> NAME/KEY: variation
<222> LOCATION: (12)
<223> OTHER INFORMATION: N = I, C, or A
<220> FEATURE:
<221> NAME/KEY: variation
<222> LOCATION: (15)
<223> OTHER INFORMATION: n = t or c
<220> FEATURE:
<221> NAME/KEY: variation
<222> LOCATION: (18)
<223> OTHER INFORMATION: N = I, C, or A

<400> SEQUENCE: 35
tantanccnc cnttngcngg                                          20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: variation
<222> LOCATION: (3)
<223> OTHER INFORMATION: n = t or c
<220> FEATURE:
<221> NAME/KEY: variation
<222> LOCATION: (6)
```

```
<223> OTHER INFORMATION: n = t or c
<220> FEATURE:
<221> NAME/KEY: variation
<222> LOCATION: (12)
<223> OTHER INFORMATION: n = c or t
<220> FEATURE:
<221> NAME/KEY: variation
<222> LOCATION: (15)
<223> OTHER INFORMATION: n = i, c, or a
<220> FEATURE:
<221> NAME/KEY: variation
<222> LOCATION: (18)
<223> OTHER INFORMATION: n=i, c, a

<400> SEQUENCE: 36
ttntanccnt tngcnggnag                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: variation
<222> LOCATION: (3)
<223> OTHER INFORMATION: n = c or t
<220> FEATURE:
<221> NAME/KEY: variation
<222> LOCATION: (6)
<223> OTHER INFORMATION: n = t or c
<220> FEATURE:
<221> NAME/KEY: variation
<222> LOCATION: (10)
<223> OTHER INFORMATION: n = t or c
<220> FEATURE:
<221> NAME/KEY: variation
<222> LOCATION: (15)
<223> OTHER INFORMATION: n = i, c, or a
<220> FEATURE:
<221> NAME/KEY: variation
<222> LOCATION: (18)
<223> OTHER INFORMATION: n = i, c, or a
<220> FEATURE:
<221> NAME/KEY: variation
<222> LOCATION: (19)
<223> OTHER INFORMATION: n = a or c

<400> SEQUENCE: 37
tantanccnn tngcnggnng                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: variation
<222> LOCATION: (3)
<223> OTHER INFORMATION: n=a or g
<220> FEATURE:
<221> NAME/KEY: variation
<222> LOCATION: (6)
<223> OTHER INFORMATION: n = a or g
<220> FEATURE:
<221> NAME/KEY: variation
<222> LOCATION: (9)
<223> OTHER INFORMATION: n = i, c, or a
<220> FEATURE:
<221> NAME/KEY: variation
<222> LOCATION: (15)
<223> OTHER INFORMATION: n= i, c, or a
<220> FEATURE:
<221> NAME/KEY: variation
```

```
<222> LOCATION: (18)
<223> OTHER INFORMATION: n = t or c

<400> SEQUENCE: 38
ctnaanccna ccccnttngg                                               20

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence:consensus
      sequence

<400> SEQUENCE: 39

Phe Tyr Pro Phe Ala Gly Arg
  1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:consensus
      sequence

<400> SEQUENCE: 40

Tyr Tyr Pro Leu Ala Gly Arg
  1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:consensus
      sequence

<400> SEQUENCE: 41

Asp Phe Gly Trp Gly Lys Pro
  1               5

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 42 cctcatctttt cccccattga taat                                         24

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 43
aaaaagaaaa taattttgcc atgcaag                                       27

<210> SEQ ID NO 44
<211> LENGTH: 1320
<212> TYPE: DNA
<213> ORGANISM: Taxus cuspidata
```

```
<400> SEQUENCE: 44
atggcaggct caacagaatt tgtggtaaga agcttagaga gagtgatggt ggctccaagc      60
cagccatcgc ccaaagcttt cctgcagctc tccacccttg acaatctacc agggtgaga     120
gaaaacattt ttaacaccct tgttagtcta c aatgcctcag acagagtttc cgtagatcct   180
```

```
<400> SEQUENCE: 44
atggcaggct caacagaatt tgtggtaaga agcttagaga gagtgatggt ggctccaagc      60
cagccatcgc ccaaagcttt cctgcagctc tccacccttg acaatctacc agggtgaga     120
gaaaacattt taacaccctt gttagtctac aatgcctcag acagagtttc cgtagatcct    180
gcaaaagtaa tccggcaggc tctctccaag gtgttggtgt actattcccc ttttgcaggg    240
cgtctcagga aaaagaaaa tggagatctt gaagtgagt gcacagggga gggtgctctg     300
tttgtggaag ccatggctga cactgacctc tcagtcttag agatttgga tgactacagt    360
ccttcacttg agcaactact tttttgtctt ccgcctgata cagatattga ggacatccat    420
cctctggtgg ttcaggtaac tcgttttaca tgtggaggtt ttgttgtagg ggtgagtttc    480
tgccatggta tatgtgatgg actaggagca ggccagtttc ttatagccat gggagagatg    540
gcaaggggag agattaagcc ctcctcggag ccaatatgga agagagaatt gctgaagccg    600
gaagacccctt tataccggtt ccagtattat cactttcaat tgatttgccc gccttcaaca    660
tcgggaaaa tagttcaagg atctcttgtt ataacctctg agacaataaa ttgtatcaaa    720
caatgcctta gggaagaaag taagaatttt tgctctgcgt tcgaagttgt atctgcattg    780
gcttggatag caaggacaag ggctcttcaa attccacata gtgagaatgt gaagcttatt    840
tttgcaatgg acatgagaaa attatttaat ccaccacttt cgaagggata ctacggtaat    900
tttgttggta ccgtatgtgc aatggataat gtcaaggacc tattaagtgg atctcttttg    960
cgtgttgtaa ggattataaa gaaagcaaag gtctctttaa atgagcattt cacgtcaaca   1020
atcgtgacac cccgttctgg atcagatgag agtatcaatt atgaaaacat agttggattt   1080
ggtgatcgaa ggcgattggg atttgatgaa gtagactttg ggtggggca tgcagataat   1140
gtaagtctcg tgcaacatgg attgaaggat gtttcagtcg tgcaaagtta ttttcttttc   1200
atacgacctc ccaagaataa ccccgatgga atcaagatcc tatcgttcat gcccccgtca   1260
atagtgaaat ccttcaaatt tgaaatggaa accatgacaa acaaatatgt aactaagcct   1320

<210> SEQ ID NO 45
<211> LENGTH: 440
<212> TYPE: PRT
<213> ORGANISM: Taxus cuspidata

<400> SEQUENCE: 45

Met Ala Gly Ser Thr Glu Phe Val Val Arg Ser Leu Glu Arg Val Met
 1               5                  10                  15

Val Ala Pro Ser Gln Pro Ser Pro Lys Ala Phe Leu Gln Leu Ser Thr
            20                  25                  30

Leu Asp Asn Leu Pro Gly Val Arg Glu Asn Ile Phe Asn Thr Leu Leu
        35                  40                  45

Val Tyr Asn Ala Ser Asp Arg Val Ser Val Asp Pro Ala Lys Val Ile
    50                  55                  60

Arg Gln Ala Leu Ser Lys Val Leu Val Tyr Tyr Ser Pro Phe Ala Gly
65                  70                  75                  80

Arg Leu Arg Lys Lys Glu Asn Gly Asp Leu Glu Val Glu Cys Thr Gly
                85                  90                  95

Glu Gly Ala Leu Phe Val Glu Ala Met Ala Asp Thr Asp Leu Ser Val
            100                 105                 110

Leu Gly Asp Leu Asp Asp Tyr Ser Pro Ser Leu Glu Gln Leu Leu Phe
        115                 120                 125

Cys Leu Pro Pro Asp Thr Asp Ile Glu Asp Ile His Pro Leu Val Val
```

```
              130                 135                 140
Gln Val Thr Arg Phe Thr Cys Gly Gly Phe Val Gly Val Ser Phe
145                 150                 155                 160

Cys His Gly Ile Cys Asp Gly Leu Gly Ala Gly Gln Phe Leu Ile Ala
                165                 170                 175

Met Gly Glu Met Ala Arg Gly Glu Ile Lys Pro Ser Ser Glu Pro Ile
                180                 185                 190

Trp Lys Arg Glu Leu Leu Lys Pro Glu Asp Pro Leu Tyr Arg Phe Gln
            195                 200                 205

Tyr Tyr His Phe Gln Leu Ile Cys Pro Pro Ser Thr Phe Gly Lys Ile
210                 215                 220

Val Gln Gly Ser Leu Val Ile Thr Ser Glu Thr Ile Asn Cys Ile Lys
225                 230                 235                 240

Gln Cys Leu Arg Glu Glu Ser Lys Glu Phe Cys Ser Ala Phe Glu Val
                245                 250                 255

Val Ser Ala Leu Ala Trp Ile Ala Arg Thr Arg Ala Leu Gln Ile Pro
                260                 265                 270

His Ser Glu Asn Val Lys Leu Ile Phe Ala Met Asp Met Arg Lys Leu
            275                 280                 285

Phe Asn Pro Pro Leu Ser Lys Gly Tyr Tyr Gly Asn Phe Val Gly Thr
290                 295                 300

Val Cys Ala Met Asp Asn Val Lys Asp Leu Leu Ser Gly Ser Leu Leu
305                 310                 315                 320

Arg Val Val Arg Ile Ile Lys Lys Ala Lys Val Ser Leu Asn Glu His
                325                 330                 335

Phe Thr Ser Thr Ile Val Thr Pro Arg Ser Gly Ser Asp Glu Ser Ile
                340                 345                 350

Asn Tyr Glu Asn Ile Val Gly Phe Gly Asp Arg Arg Arg Leu Gly Phe
            355                 360                 365

Asp Glu Val Asp Phe Gly Trp Gly His Ala Asp Asn Val Ser Leu Val
            370                 375                 380

Gln His Gly Leu Lys Asp Val Ser Val Val Gln Ser Tyr Phe Leu Phe
385                 390                 395                 400

Ile Arg Pro Pro Lys Asn Asn Pro Asp Gly Ile Lys Ile Leu Ser Phe
                405                 410                 415

Met Pro Pro Ser Ile Val Lys Ser Phe Lys Phe Glu Met Glu Thr Met
                420                 425                 430

Thr Asn Lys Tyr Val Thr Lys Pro
            435                 440

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: PCR Primer

<400> SEQUENCE: 46
gggaattcca tatggcaggc tcaacagaat ttgtgg                              36

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: PCR Primer
```

-continued

```
<400> SEQUENCE: 47
gtttatacat tgattcggaa ctagatctga tc                                    32

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: 6 amino
      acid motif found in acyl transferases
<220> FEATURE:
<221> NAME/KEY: VARIANT
<222> LOCATION: (2)..(4)
<223> OTHER INFORMATION: Any amino acid

<400> SEQUENCE: 48

His Xaa Xaa Xaa Asp Gly
  1               5

<210> SEQ ID NO 49
<211> LENGTH: 1332
<212> TYPE: DNA
<213> ORGANISM: Taxus cuspidata

<400> SEQUENCE: 49
atggagaagt ctggttcagc agatctacat gtaaatatca ttgagcgagt ggtggtggcg      60
ccatgccagc cgacgcccaa acaatcctg cagctctcta gcattgacaa atgggagga       120 ggatttgcca acgtattgct agtcttcggt gcctcccatg cgtttctgc agatcctgca     180 aaaacaattc gagaggctct ctccaagacc ttggtctttt atttcccttt tgctgggcgg    240
ctcagaaaga agaagatgg ggatatcgaa gtggagtgca tagagcaggg agctctgttc      300
gtggaagcca tgcggacaa cgatctttca gtcgtacgag atctggatga gtacaatcca     360
ttatttcggc agctacaatc ttcgctttca ctggatacag attacaagga cctccatctt    420
atgactgttc aggtaactcc gtttacatgt gggggttttg tcatgggaac gagtgtacac    480
caaagtatat gcgatggaaa tggattgggg caattttta aaagcatggc agagatagtg     540
aggggagaag ttaagccctc aatcgaacca atatggaata gagaattggt gaagcctgaa    600
gactatatac acctccagtt gtatgtcagt gaattcattc gcccaccttt agtagttgag    660
aaagttgggc aaacatctct tgttataagc ttcgagaaaa taaatcatat caaacgatgc    720
attatgaaag aaagtaaaga atctttctct tcatttgaaa ttgtaacagc aatggttttgg   780 ctagcaagga caagggcttt tcaaattcca cacaacgagg atgtgactct tctccttgca    840
atggatgcaa ggagatcatt tgacccccct attccgaagg gatactacgg taatgtcatt    900
ggtactacat atgcaaaaga taatgtccac aacctcttaa gtggatctct tttgcatgct    960
ctaacagtta aaagaaatc aatgtcctca ttttatgaga atatgacctc aagagtcttg   1020
gtgaacccat ctacattaga tttgagtatg aagtatgaaa atgtagtttc acttagtgat   1080
tggagccggt tgggacataa tgaagtggac tttgggtggg aaatgcaat aaatgtaagc    1140 actctgcaac aacaatggga aaatgaggta gctataccaa ctttttttac tttccttcaa   1200
actcccaaga atataccaga tggaatcaag atactaatgt tcatgccccc atcaagagag   1260
aaaacattcg aaattgaagt ggaagccatg ataagaaaat atttgactaa agtgtcgcat   1320
tcaaagctat aa                                                       1332

<210> SEQ ID NO 50
<211> LENGTH: 443
```

```
<212> TYPE: PRT
<213> ORGANISM: Taxus cuspidata

<400> SEQUENCE: 50

Met Glu Lys Ser Gly Ser Ala Asp Leu His Val Asn Ile Ile Glu Arg
  1               5                  10                  15

Val Val Val Ala Pro Cys Gln Pro Thr Pro Lys Thr Ile Leu Gln Leu
             20                  25                  30

Ser Ser Ile Asp Lys Met Gly Gly Phe Ala Asn Val Leu Leu Val
         35                  40                  45

Phe Gly Ala Ser His Gly Val Ser Ala Asp Pro Ala Lys Thr Ile Arg
 50                  55                  60

Glu Ala Leu Ser Lys Thr Leu Val Phe Tyr Phe Pro Phe Ala Gly Arg
 65                  70                  75                  80

Leu Arg Lys Lys Glu Asp Gly Asp Ile Glu Val Glu Cys Ile Glu Gln
                 85                  90                  95

Gly Ala Leu Phe Val Glu Ala Met Ala Asp Asn Asp Leu Ser Val Val
            100                 105                 110

Arg Asp Leu Asp Glu Tyr Asn Pro Leu Phe Arg Gln Leu Gln Ser Ser
            115                 120                 125

Leu Ser Leu Asp Thr Asp Tyr Lys Asp Leu His Leu Met Thr Val Gln
130                 135                 140

Val Thr Pro Phe Thr Cys Gly Gly Phe Val Met Gly Thr Ser Val His
145                 150                 155                 160

Gln Ser Ile Cys Asp Gly Asn Gly Leu Gly Gln Phe Phe Lys Ser Met
                165                 170                 175

Ala Glu Ile Val Arg Gly Glu Val Lys Pro Ser Ile Glu Pro Ile Trp
            180                 185                 190

Asn Arg Glu Leu Val Lys Pro Glu Asp Tyr Ile His Leu Gln Leu Tyr
            195                 200                 205

Val Ser Glu Phe Ile Arg Pro Pro Leu Val Val Glu Lys Val Gly Gln
210                 215                 220

Thr Ser Leu Val Ile Ser Phe Glu Lys Ile Asn His Ile Lys Arg Cys
225                 230                 235                 240

Ile Met Glu Glu Ser Lys Glu Ser Phe Ser Ser Phe Glu Ile Val Thr
                245                 250                 255

Ala Met Val Trp Leu Ala Arg Thr Arg Ala Phe Gln Ile Pro His Asn
            260                 265                 270

Glu Asp Val Thr Leu Leu Leu Ala Met Asp Ala Arg Arg Ser Phe Asp
            275                 280                 285

Pro Pro Ile Pro Lys Gly Tyr Tyr Gly Asn Val Ile Gly Thr Thr Tyr
290                 295                 300

Ala Lys Asp Asn Val His Asn Leu Leu Ser Gly Ser Leu Leu His Ala
305                 310                 315                 320

Leu Thr Val Ile Lys Lys Ser Met Ser Ser Phe Tyr Glu Asn Met Thr
                325                 330                 335

Ser Arg Val Leu Val Asn Pro Ser Thr Leu Asp Leu Ser Met Lys Tyr
            340                 345                 350

Glu Asn Val Val Ser Leu Ser Asp Trp Ser Arg Leu Gly His Asn Glu
            355                 360                 365

Val Asp Phe Gly Trp Gly Asn Ala Ile Asn Val Ser Thr Leu Gln Gln
370                 375                 380

Gln Trp Glu Asn Glu Val Ala Ile Pro Thr Phe Thr Phe Leu Gln
385                 390                 395                 400
```

```
Thr Pro Lys Asn Ile Pro Asp Gly Ile Lys Ile Leu Met Phe Met Pro
            405                 410                 415
Pro Ser Arg Glu Lys Thr Phe Glu Ile Glu Val Glu Ala Met Ile Arg
        420                 425                 430
Lys Tyr Leu Thr Lys Val Ser His Ser Lys Leu
        435                 440
```

<210> SEQ ID NO 51
<211> LENGTH: 1338
<212> TYPE: DNA
<213> ORGANISM: Taxus cuspidata

<400> SEQUENCE: 51

| | | | | | |
|---|---|---|---|---|---|
| atgaagaaga | caggttcgtt | tgcagagttc | catgtgaata | tgattgagcg | agtcatggtg | 60 |
| agaccgtgcc | tgccttcgcc | caaaacaatc | ctccctctct | ccgccattga | acacatggca | 120 |
| agagcttttt | ctaacgtatt | gctggtctac | gctgccaaca | tggacagagt | ctctgcagat | 180 |
| cctgcaaaag | tgattcgaga | ggctctctcc | aaggtgctgg | tttattatta | cccttttgct | 240 |
| gggcggctca | gaaataaaga | aaatggggaa | cttgaagtgg | agtgcacagg | gcagggtgtt | 300 |
| ctgtttctgg | aagccatggc | tgacagcgac | ctttcagtct | taacagatct | ggataactac | 360 |
| aatccatcgt | ttcagcagtt | gattttttct | ctaccacagg | atacagatat | tgaggacctc | 420 |
| catctcttga | ttgttcaggt | aactcgtttt | acatgtgggg | gttttgttgt | gggagcgaat | 480 |
| gtgtatggta | gtgcatgcga | tgcaaaagga | tttggccagt | ttcttcaaag | tatggcagag | 540 |
| atggcgagag | gagaggttaa | gccctcgatt | gaaccgatat | ggaatagaga | actggtgaag | 600 |
| ctagaacatt | gtatgccctt | ccggatgagt | catcttcaaa | ttatacatgc | acctgtaatt | 660 |
| gaggagaaat | ttgttcaaac | atctcttgtt | ataaactttg | agataataaa | tcatatcaga | 720 |
| cgacgcatca | tggaagaacg | caagaaagt | ttatcttcat | ttgaaattgt | agcagcattg | 780 |
| gtttggctag | caaagataaa | ggcttttcaa | attccacata | gtgagaatgt | gaagcttctt | 840 |
| tttgcaatgg | acttgaggag | atcatttaat | cccctcttc | acatggata | ctatggcaat | 900 |
| gcctttggta | ttgcatgtgc | aatggataat | gtccatgacc | ttctaagtgg | atctcttttg | 960 |
| cgcactataa | tgatcataaa | gaaatcaaag | ttctctttac | acaaagaact | caactcaaaa | 1020 |
| accgtgatga | gctcatctgt | agtagatgtc | aatacgaagt | ttgaagatgt | agtttcaatt | 1080 |
| agtgattgga | ggcattctat | atattatgaa | gtggactttg | ggtggggaga | tgcaatgaac | 1140 |
| gtgagcacta | tgctacaaca | acaggagcac | gagaaatctc | tgccaactta | ttttttctttc | 1200 |
| ctacaatcta | ctaagaacat | gccagatgga | atcaagatgc | taatgtttat | gcctccatca | 1260 |
| aaactgaaaa | aattcaaaat | tgaaatagaa | gctatgataa | aaaatatgt | gactaaagtg | 1320 |
| tgtccgtcaa | agttatga | | | | | 1338 |

<210> SEQ ID NO 52
<211> LENGTH: 445
<212> TYPE: PRT
<213> ORGANISM: Taxus cuspidata

<400> SEQUENCE: 52

```
Met Lys Lys Thr Gly Ser Phe Ala Glu Phe His Val Asn Met Ile Glu
 1               5                  10                  15
Arg Val Met Val Arg Pro Cys Leu Pro Ser Pro Lys Thr Ile Leu Pro
            20                  25                  30
Leu Ser Ala Ile Asp Asn Met Ala Arg Ala Phe Ser Asn Val Leu Leu
```

```
                    35                  40                  45
Val Tyr Ala Ala Asn Met Asp Arg Val Ser Ala Asp Pro Ala Lys Val
 50                  55                  60

Ile Arg Glu Ala Leu Ser Lys Val Leu Val Tyr Tyr Pro Phe Ala
 65                  70                  75                  80

Gly Arg Leu Arg Asn Lys Glu Asn Gly Glu Leu Glu Val Glu Cys Thr
                     85                  90                  95

Gly Gln Gly Val Leu Phe Leu Glu Ala Met Ala Asp Ser Asp Leu Ser
                100                 105                 110

Val Leu Thr Asp Leu Asp Asn Tyr Asn Pro Ser Phe Gln Gln Leu Ile
                115                 120                 125

Phe Ser Leu Pro Gln Asp Thr Asp Ile Glu Asp Leu His Leu Leu Ile
            130                 135                 140

Val Gln Val Thr Arg Phe Thr Cys Gly Gly Phe Val Val Gly Ala Asn
145                 150                 155                 160

Val Tyr Gly Ser Ala Cys Asp Ala Lys Gly Phe Gly Gln Phe Leu Gln
                165                 170                 175

Ser Met Ala Glu Met Ala Arg Gly Glu Val Lys Pro Ser Ile Glu Pro
            180                 185                 190

Ile Trp Asn Arg Glu Leu Val Lys Leu Glu His Cys Met Pro Phe Arg
            195                 200                 205

Met Ser His Leu Gln Ile Ile His Ala Pro Val Ile Glu Glu Lys Phe
            210                 215                 220

Val Gln Thr Ser Leu Val Ile Asn Phe Glu Ile Ile Asn His Ile Arg
225                 230                 235                 240

Arg Arg Ile Met Glu Glu Arg Lys Glu Ser Leu Ser Ser Phe Glu Ile
                245                 250                 255

Val Ala Ala Leu Val Trp Leu Ala Lys Ile Lys Ala Phe Gln Ile Pro
            260                 265                 270

His Ser Glu Asn Val Lys Leu Leu Phe Ala Met Asp Leu Arg Arg Ser
            275                 280                 285

Phe Asn Pro Pro Leu Pro His Gly Tyr Tyr Gly Asn Ala Phe Gly Ile
            290                 295                 300

Ala Cys Ala Met Asp Asn Val His Asp Leu Leu Ser Gly Ser Leu Leu
305                 310                 315                 320

Arg Thr Ile Met Ile Ile Lys Lys Ser Lys Phe Ser Leu His Lys Glu
                325                 330                 335

Leu Asn Ser Lys Thr Val Met Ser Ser Val Val Asp Val Asn Thr
            340                 345                 350

Lys Phe Glu Asp Val Val Ser Ile Ser Asp Trp Arg His Ser Ile Tyr
            355                 360                 365

Tyr Glu Val Asp Phe Gly Trp Gly Asp Ala Met Asn Val Ser Thr Met
            370                 375                 380

Leu Gln Gln Gln Glu His Gly Lys Ser Leu Pro Thr Tyr Phe Ser Phe
385                 390                 395                 400

Leu Gln Ser Thr Lys Asn Met Pro Asp Gly Ile Lys Met Leu Met Phe
                405                 410                 415

Met Pro Pro Ser Lys Leu Lys Lys Phe Lys Ile Glu Ile Glu Ala Met
            420                 425                 430

Ile Lys Lys Tyr Val Thr Lys Val Cys Pro Ser Lys Leu
            435                 440                 445

<210> SEQ ID NO 53
```

-continued

```
<211> LENGTH: 1326
<212> TYPE: DNA
<213> ORGANISM: Taxus cuspidata

<400> SEQUENCE: 53
atggagaagg caggctcaac agacttccat gtaaagaaat ttgatccagt catggtagcc      60
ccaagccttc catcgcccaa agctaccgtc cagctctctg tcgttgatag cctaacaatc     120 tgcagggaa  ttttttaacac gttgttggtt ttcaatgccc ctgacaacat ttctgcagat    180
cctgtaaaaa taattagaga ggctctctcc aaggtgttgg tgtattattt ccctcttgct     240
gggcggctca gaagtaaaga aattggggaa cttgaagtgg agtgcacagg ggatggtgct     300
ctgtttgtgg aagccatggt ggaagacacc atttcagtct tacgagatct ggatgacctc     360
aatccatcat ttcagcagtt agttttttgg catccattgg acactgctat tgaggatctt     420
catcttgtga ttgttcaggt aacacgtttt acatgtgggg gcattgccgt tggagtgact     480
ttgccccata gtgtatgtga tggacgtgga gcagcccagt tgttacagc  actggcagag     540 atggcgaggg gagaggttaa gccctcacta gaaccaatat ggaatagaga attgttgaac     600
cctgaagacc ctctacatct ccagttaaat caatttgatt cgatatgccc acctccaatg     660
ctggaggaat tgggtcaagc ttcttttgtt ataaacgttg acaccataga atatatgaag     720
caatgtgtca tggaggaatg taatgaattt tgttcgtctt ttgaagtagt ggcagcattg     780
gtttggatag cacggacaaa ggctcttcaa attccacata ctgagaatgt gaagcttctc     840
tttgcgatgg atttgaggaa attatttaat cccccacttc caaatggata ttatggtaat     900
gccattggta ctgcatatgc aatggataat gtccaagacc tcttaaatgg atctcttttg     960
cgtgctataa tgattataaa aaaagcaaag gctgatttaa aagataatta ttcgaggtca    1020
agggtagtta caaacccata ttcattagat gtgaacaaga atccgacaa  cattcttgca    1080 ttgagtgact ggaggcggtt gggattttat gaagccgatt tgggtgggg  aggtccactg    1140 aatgtaagtt ccctgcaacg gttggaaaat ggattgccta tgtttagtac ttttctatac    1200
ctactacctg ccaaaaacaa gtctgatgga atcaagctgc tactgtcttg tatgccacca    1260
acaacattga atcatttaa  aattgtaatg gaagctatga tagagaaata tgtaagtaaa    1320
gtgtga                                                               1326

<210> SEQ ID NO 54
<211> LENGTH: 441
<212> TYPE: PRT
<213> ORGANISM: Taxus cuspidata

<400> SEQUENCE: 54

Met Glu Lys Ala Gly Ser Thr Asp Phe His Val Lys Lys Phe Asp Pro
 1               5                  10                  15

Val Met Val Ala Pro Ser Leu Pro Ser Pro Lys Ala Thr Val Gln Leu
            20                  25                  30

Ser Val Val Asp Ser Leu Thr Ile Cys Arg Gly Ile Phe Asn Thr Leu
        35                  40                  45

Leu Val Phe Asn Ala Pro Asp Asn Ile Ser Ala Asp Pro Val Lys Ile
    50                  55                  60

Ile Arg Glu Ala Leu Ser Lys Val Leu Val Tyr Tyr Phe Pro Leu Ala
65                  70                  75                  80

Gly Arg Leu Arg Ser Lys Glu Ile Gly Glu Leu Glu Val Glu Cys Thr
                85                  90                  95

Gly Asp Gly Ala Leu Phe Val Glu Ala Met Val Glu Asp Thr Ile Ser
```

|     |     |     |     | 100 |     |     |     |     | 105 |     |     |     |     | 110 |     |
| --- | --- | --- | --- | --- | --- | --- | --- | --- | --- | --- | --- | --- | --- | --- | --- |
| Val | Leu | Arg | Asp | Leu | Asp | Asp | Leu | Asn | Pro | Ser | Phe | Gln | Gln | Leu | Val |
|     |     |     | 115 |     |     |     |     | 120 |     |     |     |     | 125 |     |     |
| Phe | Trp | His | Pro | Leu | Asp | Thr | Ala | Ile | Glu | Asp | Leu | His | Leu | Val | Ile |
|     | 130 |     |     |     |     | 135 |     |     |     |     | 140 |     |     |     |     |
| Val | Gln | Val | Thr | Arg | Phe | Thr | Cys | Gly | Gly | Ile | Ala | Val | Gly | Val | Thr |
| 145 |     |     |     |     | 150 |     |     |     |     | 155 |     |     |     |     | 160 |
| Leu | Pro | His | Ser | Val | Cys | Asp | Gly | Arg | Gly | Ala | Ala | Gln | Phe | Val | Thr |
|     |     |     |     | 165 |     |     |     |     | 170 |     |     |     |     | 175 |     |
| Ala | Leu | Ala | Glu | Met | Ala | Arg | Gly | Glu | Val | Lys | Pro | Ser | Leu | Glu | Pro |
|     |     |     | 180 |     |     |     |     | 185 |     |     |     |     | 190 |     |     |
| Ile | Trp | Asn | Arg | Glu | Leu | Leu | Asn | Pro | Glu | Asp | Pro | Leu | His | Leu | Gln |
|     |     | 195 |     |     |     |     | 200 |     |     |     |     | 205 |     |     |     |
| Leu | Asn | Gln | Phe | Asp | Ser | Ile | Cys | Pro | Pro | Met | Leu | Glu | Glu | Leu |     |
|     | 210 |     |     |     |     | 215 |     |     |     |     | 220 |     |     |     |     |
| Gly | Gln | Ala | Ser | Phe | Val | Ile | Asn | Val | Asp | Thr | Ile | Glu | Tyr | Met | Lys |
| 225 |     |     |     |     | 230 |     |     |     |     | 235 |     |     |     |     | 240 |
| Gln | Cys | Val | Met | Glu | Glu | Cys | Asn | Glu | Phe | Cys | Ser | Ser | Phe | Glu | Val |
|     |     |     |     | 245 |     |     |     |     | 250 |     |     |     |     | 255 |     |
| Val | Ala | Ala | Leu | Val | Trp | Ile | Ala | Arg | Thr | Lys | Ala | Leu | Gln | Ile | Pro |
|     |     |     | 260 |     |     |     |     | 265 |     |     |     |     | 270 |     |     |
| His | Thr | Glu | Asn | Val | Lys | Leu | Leu | Phe | Ala | Met | Asp | Leu | Arg | Lys | Leu |
|     |     | 275 |     |     |     |     | 280 |     |     |     |     | 285 |     |     |     |
| Phe | Asn | Pro | Pro | Leu | Pro | Asn | Gly | Tyr | Tyr | Gly | Asn | Ala | Ile | Gly | Thr |
|     | 290 |     |     |     |     | 295 |     |     |     |     | 300 |     |     |     |     |
| Ala | Tyr | Ala | Met | Asp | Asn | Val | Gln | Asp | Leu | Leu | Asn | Gly | Ser | Leu | Leu |
| 305 |     |     |     |     | 310 |     |     |     |     | 315 |     |     |     |     | 320 |
| Arg | Ala | Ile | Met | Ile | Ile | Lys | Lys | Ala | Lys | Ala | Asp | Leu | Lys | Asp | Asn |
|     |     |     |     | 325 |     |     |     |     | 330 |     |     |     |     | 335 |     |
| Tyr | Ser | Arg | Ser | Arg | Val | Val | Thr | Asn | Pro | Tyr | Ser | Leu | Asp | Val | Asn |
|     |     |     | 340 |     |     |     |     | 345 |     |     |     |     | 350 |     |     |
| Lys | Lys | Ser | Asp | Asn | Ile | Leu | Ala | Leu | Ser | Asp | Trp | Arg | Arg | Leu | Gly |
|     |     | 355 |     |     |     |     | 360 |     |     |     |     | 365 |     |     |     |
| Phe | Tyr | Glu | Ala | Asp | Phe | Gly | Trp | Gly | Gly | Pro | Leu | Asn | Val | Ser | Ser |
|     | 370 |     |     |     |     | 375 |     |     |     |     | 380 |     |     |     |     |
| Leu | Gln | Arg | Leu | Glu | Asn | Gly | Leu | Pro | Met | Phe | Ser | Thr | Phe | Leu | Tyr |
| 385 |     |     |     |     | 390 |     |     |     |     | 395 |     |     |     |     | 400 |
| Leu | Leu | Pro | Ala | Lys | Asn | Lys | Ser | Asp | Gly | Ile | Lys | Leu | Leu | Leu | Ser |
|     |     |     |     | 405 |     |     |     |     | 410 |     |     |     |     | 415 |     |
| Cys | Met | Pro | Pro | Thr | Thr | Leu | Lys | Ser | Phe | Lys | Ile | Val | Met | Glu | Ala |
|     |     |     | 420 |     |     |     |     | 425 |     |     |     |     | 430 |     |     |
| Met | Ile | Glu | Lys | Tyr | Val | Ser | Lys | Val |     |     |     |     |     |     |     |
|     |     |     | 435 |     |     |     |     | 440 |     |     |     |     |     |     |     |

<210> SEQ ID NO 55
<211> LENGTH: 1347
<212> TYPE: DNA
<213> ORGANISM: Taxus cuspidata

<400> SEQUENCE: 55
atggagaagg gaaatgcgag tgatgtgcca gaattgcatg tacagatctg tgagcgggtg      60
atggtgaaac catgcgtgcc ttctccttcg ccaaatcttg tcctccagct ctccgcggtg     120
gacagactgc agggatgaa gtttgctact tttagcgccg tgttagtcta caatgccagc     180

-continued

```
tctcactcca tttttgcaaa tcctgcacag attattcggc aggctctctc caaggtgttg    240
cagtattatc ccgcttttgc cgggcggatc agacagaaag aaaatgagga actggaagtg    300
gagtgcacag gggagggtgc gctgtttgtg aagccctggt cgacaatga tctttcagtc    360 ttgcgagatt tggatgccca aaatgcatct tatgagcagt tgctcttttc gcttccgccc    420
aatatacagg ttcaggacct ccatcctctg attcttcagg taactcgttt tacgtgtgga    480
ggttttgttg tgggagtagg ttttcaccat ggtatatgcg acgcacgagg aggaactcaa    540
tttcttcaag gcctagcaga tatggcaagg ggagagacta agcctttagt ggaaccagta    600
tggaatagag aactgataaa gcccgaagat ctaatgcacc tccaatttca taagtttggt    660
ttgatacgcc aacctctaaa acttgatgaa atttgtcaag catcttttac tataaactca    720
gagataataa attacatcaa acaatgtgtt atagaagaat gtaacgaaat tttctctgca    780
tttgaagttg tagtagcatt aacttggata gcaaggacaa aggcttttca aattccacat    840
aatgagaatg tgatgatgct ctttggaatg acgcgaggaa atatttaa tcccccactt    900 ccaaagggat attatggtaa tgccattggt acttcatgtg taattgaaaa tgtacaagac    960
ctcttaaatg gatctctttc gcgtgctgta atgattacaa agaaatcaaa gatcccttta    1020
attgagaatt taaggtcaag aattgtggcg aaccaatctg gagtagatga ggaaattaag    1080
catgaaaacg tagttggatt tggagattgg aggcgattgg gatttcatga agtggacttc    1140
ggatcgggag atgcagtgaa catcagcccc atacaacaac gactagagga tgatcaattg    1200
gctatgcgaa attattttct tttccttcga ccttacaagg acatgcctaa tggaatcaaa    1260
atactaatgt tcatggatcc atcaagagtg aaattattca aagatgaaat ggaagccatg    1320
ataattaaat atatgccgaa agcctaa                                          1347
```

<210> SEQ ID NO 56
<211> LENGTH: 448
<212> TYPE: PRT
<213> ORGANISM: Taxus cuspidata

<400> SEQUENCE: 56

```
Met Glu Lys Gly Asn Ala Ser Asp Val Pro Glu Leu His Val Gln Ile
  1               5                  10                  15

Cys Glu Arg Val Met Val Lys Pro Cys Val Pro Ser Pro Ser Pro Asn
                 20                  25                  30

Leu Val Leu Gln Leu Ser Ala Val Asp Arg Leu Pro Gly Met Lys Phe
             35                  40                  45

Ala Thr Phe Ser Ala Val Leu Val Tyr Asn Ala Ser Ser His Ser Ile
         50                  55                  60

Phe Ala Asn Pro Ala Gln Ile Ile Arg Gln Ala Leu Ser Lys Val Leu
 65                  70                  75                  80

Gln Tyr Tyr Pro Ala Phe Ala Gly Arg Ile Arg Gln Lys Glu Asn Glu
                 85                  90                  95

Glu Leu Glu Val Glu Cys Thr Gly Glu Gly Ala Leu Phe Val Glu Ala
            100                 105                 110

Leu Val Asp Asn Asp Leu Ser Val Leu Arg Asp Leu Asp Ala Gln Asn
            115                 120                 125

Ala Ser Tyr Glu Gln Leu Leu Phe Ser Leu Pro Pro Asn Ile Gln Val
        130                 135                 140

Gln Asp Leu His Pro Leu Ile Leu Gln Val Thr Arg Phe Thr Cys Gly
145                 150                 155                 160

Gly Phe Val Val Gly Val Gly Phe His His Gly Ile Cys Asp Ala Arg
```

-continued

```
                165                 170                 175
Gly Gly Thr Gln Phe Leu Gln Gly Leu Ala Asp Met Ala Arg Gly Glu
            180                 185                 190

Thr Lys Pro Leu Val Glu Pro Val Trp Asn Arg Glu Leu Ile Lys Pro
        195                 200                 205

Glu Asp Leu Met His Leu Gln Phe His Lys Phe Gly Leu Ile Arg Gln
    210                 215                 220

Pro Leu Lys Leu Asp Glu Ile Cys Gln Ala Ser Phe Thr Ile Asn Ser
225                 230                 235                 240

Glu Ile Ile Asn Tyr Ile Lys Gln Cys Val Ile Glu Glu Cys Asn Glu
                245                 250                 255

Ile Phe Ser Ala Phe Glu Val Val Ala Leu Thr Trp Ile Ala Arg
            260                 265                 270

Thr Lys Ala Phe Gln Ile Pro His Asn Glu Asn Val Met Met Leu Phe
        275                 280                 285

Gly Met Asp Ala Arg Lys Tyr Phe Asn Pro Pro Leu Pro Lys Gly Tyr
    290                 295                 300

Tyr Gly Asn Ala Ile Gly Thr Ser Cys Val Ile Glu Asn Val Gln Asp
305                 310                 315                 320

Leu Leu Asn Gly Ser Leu Ser Arg Ala Val Met Ile Thr Lys Lys Ser
                325                 330                 335

Lys Ile Pro Leu Ile Glu Asn Leu Arg Ser Arg Ile Val Ala Asn Gln
            340                 345                 350

Ser Gly Val Asp Glu Glu Ile Lys His Glu Asn Val Val Gly Phe Gly
        355                 360                 365

Asp Trp Arg Arg Leu Gly Phe His Glu Val Asp Phe Gly Ser Gly Asp
    370                 375                 380

Ala Val Asn Ile Ser Pro Ile Gln Gln Arg Leu Glu Asp Asp Gln Leu
385                 390                 395                 400

Ala Met Arg Asn Tyr Phe Leu Phe Leu Arg Pro Tyr Lys Asp Met Pro
                405                 410                 415

Asn Gly Ile Lys Ile Leu Met Phe Met Asp Pro Ser Arg Val Lys Leu
            420                 425                 430

Phe Lys Asp Glu Met Glu Ala Met Ile Ile Lys Tyr Met Pro Lys Ala
        435                 440                 445
```

<210> SEQ ID NO 57
<211> LENGTH: 1317
<212> TYPE: DNA
<213> ORGANISM: Taxus cuspidata

<400> SEQUENCE: 57

```
atggagaagt acatgtgga tatcattgag agagtgaagg tggcgccatg ccttccatcg      60
tccaaagaaa ttctccagct ctccagcctc gacaacatac tcagatgtta tgtcagcgta    120
ttgttcgtct acgacagggt ttcaactgtt tctgcaaatc ctgcaaaaac aattcgagag    180
gctctctcca aggttttggt ttattattca ccttttgctg aaggctcag aaacaaagaa     240 aatgggatc ttgaagtgga gtgcagtggg gagggtgctg tctttgtgga agccatggcg     300
gacaacgagc tttcagtctt acaagatttg atgagtact gtacatcgct taaacagcta    360
atttttacag taccaatgga tacgaaaatt gaagacctcc atcttctaag tgttcaggta    420
actagtttta catgtggggg atttgttgtg ggaataagtt ctaccatac tatatgtgat    480 ggaaaaggac tgggccagtt tcttcaaggc atgagtgaga tttccaaggg agcatttaaa   540
```

-continued

```
ccctcactag aaccagtatg gaatagagaa atggtgaagc ctgaacacct tatgttcctc    600
cagtttaata attttgaatt cgtaccacat cctcttaaat ttaagaagat tgttaaagca    660
tctattgaaa ttaactttga gacaataaat tgtttcaagc aatgcatgat ggaagaatgt    720
aaagaaaatt tctctacatt tgaaattgta gcagcactga tttggctagc caagacaaag    780
tctttccaaa ttccagatag tgagaatgtg aaacttatgt ttgcagtcga catgaggaca    840
tcgtttgacc cccctcttcc aaagggatat tatggtaatg ttattggtat tgcaggtgca    900
atagataatg tcaaagaact cttaagtgga tcaattttgc gtgctctaat tattatccaa    960
aagacaattt tctctttaaa agataatttc atatcaagaa gattgatgaa accatctaca   1020
ttggatgtga atatgaagca tgaaaatgta gttctcttag gggattggag gaatttggga   1080
tattatgagg cagattgtgg gtgtggaaat ctatcaaatg taattcccat ggatcaacaa   1140
atagagcatg agtcacctgt gcaaagtaga tttatgttgc ttcgatcatc caagaacatg   1200
caaaatggaa tcaagatact aatgtccatg cctgaatcaa tggcgaaacc attcaaaagt   1260
gaaatgaaat tcacaataaa aaaatatgtg actggagcgt gtttctctga gttatga     1317
```

<210> SEQ ID NO 58
<211> LENGTH: 438
<212> TYPE: PRT
<213> ORGANISM: Taxus cuspidata

<400> SEQUENCE: 58

```
Met Glu Lys Leu His Val Asp Ile Ile Glu Arg Val Lys Val Ala Pro
  1               5                  10                  15

Cys Leu Pro Ser Ser Lys Glu Ile Leu Gln Leu Ser Ser Leu Asp Asn
                 20                  25                  30

Ile Leu Arg Cys Tyr Val Ser Val Leu Phe Val Tyr Asp Arg Val Ser
             35                  40                  45

Thr Val Ser Ala Asn Pro Ala Lys Thr Ile Arg Glu Ala Leu Ser Lys
         50                  55                  60

Val Leu Val Tyr Tyr Ser Pro Phe Ala Gly Arg Leu Arg Asn Lys Glu
 65                  70                  75                  80

Asn Gly Asp Leu Glu Val Glu Cys Ser Gly Glu Gly Ala Val Phe Val
                 85                  90                  95

Glu Ala Met Ala Asp Asn Glu Leu Ser Val Leu Gln Asp Leu Asp Glu
            100                 105                 110

Tyr Cys Thr Ser Leu Lys Gln Leu Ile Phe Thr Val Pro Met Asp Thr
        115                 120                 125

Lys Ile Glu Asp Leu His Leu Leu Ser Val Gln Val Thr Ser Phe Thr
    130                 135                 140

Cys Gly Gly Phe Val Val Gly Ile Ser Phe Tyr His Thr Ile Cys Asp
145                 150                 155                 160

Gly Lys Gly Leu Gly Gln Phe Leu Gln Gly Met Ser Glu Ile Ser Lys
                165                 170                 175

Gly Ala Phe Lys Pro Ser Leu Glu Pro Val Trp Asn Arg Glu Met Val
            180                 185                 190

Lys Pro Glu His Leu Met Phe Leu Gln Phe Asn Asn Phe Glu Phe Val
        195                 200                 205

Pro His Pro Leu Lys Phe Lys Lys Ile Val Lys Ala Ser Ile Glu Ile
    210                 215                 220

Asn Phe Glu Thr Ile Asn Cys Phe Lys Gln Cys Met Met Glu Glu Cys
225                 230                 235                 240
```

-continued

```
Lys Glu Asn Phe Ser Thr Phe Glu Ile Val Ala Ala Leu Ile Trp Leu
                245                 250                 255
Ala Lys Thr Lys Ser Phe Gln Ile Pro Asp Ser Glu Asn Val Lys Leu
            260                 265                 270
Met Phe Ala Val Asp Met Arg Thr Ser Phe Asp Pro Pro Leu Pro Lys
        275                 280                 285
Gly Tyr Tyr Gly Asn Val Ile Gly Ile Ala Gly Ala Ile Asp Asn Val
    290                 295                 300
Lys Glu Leu Leu Ser Gly Ser Ile Leu Arg Ala Leu Ile Ile Gln
305                 310                 315                 320
Lys Thr Ile Phe Ser Leu Lys Asp Asn Phe Ile Ser Arg Arg Leu Met
                325                 330                 335
Lys Pro Ser Thr Leu Asp Val Asn Met Lys His Glu Asn Val Val Leu
            340                 345                 350
Leu Gly Asp Trp Arg Asn Leu Gly Tyr Tyr Glu Ala Asp Cys Gly Cys
        355                 360                 365
Gly Asn Leu Ser Asn Val Ile Pro Met Asp Gln Gln Ile Glu His Glu
    370                 375                 380
Ser Pro Val Gln Ser Arg Phe Met Leu Leu Arg Ser Ser Lys Asn Met
385                 390                 395                 400
Gln Asn Gly Ile Lys Ile Leu Met Ser Met Pro Glu Ser Met Ala Lys
                405                 410                 415
Pro Phe Lys Ser Glu Met Lys Phe Thr Ile Lys Lys Tyr Val Thr Gly
            420                 425                 430
Ala Cys Phe Ser Glu Leu
        435
```

<210> SEQ ID NO 59
<211> LENGTH: 1314
<212> TYPE: DNA
<213> ORGANISM: Taxus cuspidata

<400> SEQUENCE: 59

```
atggagaagg caggctcatc aacagagttc catgtaaaga tctctgatcc agtcatggtg      60
ccccctgca tcccttcccc caaaacaatc ctccagctct ccgccgtaga caattaccca     120
gcggtaagag gaaatattct cgactgcctg ttagtctaca atgcctctaa caccatttct     180
gcagatcctg cgactgtaat tcgggaggct ctctccaagg tgttggtgta ttattttcct     240
tttgctgggc ggatgagaaa caaaggagat ggggaactgg aagtggattg cacggggaa      300
ggtgctctgt tgtagaagc catggcggac acaacctttt cagtgttggg aggttttgat     360
taccacaatc cagcatttgg gaagctactt tactcactac cactggatac ccctattcac     420
gacctccatc ctctggttgt tcaggtaact cgttttacct gcgggggtt tgttgtggga     480
ttaagttgg accatagtat atgtgatgga cgtggtgcag gtcaatttct taaagcccta     540
gcagagatgg cgaggggaga ggctaagccc tcattggaac caatatggaa tagagagttg     600
ttgaagcccg aagaccttat acgcctgcaa ttttatcact tgaatcgat gcgtccacct     660
ccaatagttg aagaaattgt tcaagcatct attattgtaa actctgagac aataagtaat     720
atcaaacaat acattatgga agaatgtaaa gaatctagtt ttgcatttga ggtcgtagca     780
gcattggcct ggctagcgag gacaagggct tttcaaattc cacatacaga gaatgtaaag     840
cttctttttg cagtggatac gaggagatca tttgatccac cacttccaaa aggttactat     900
ggtaatgccg ctggtaatgc atgtgcaatg gataatgttc aagacctctt aaatggatct     960
```

-continued

```
ctattgcggg ctgtaatgat tataaagaaa tcaaaggtct ctttaaatga gaatataagg    1020
gcaaaaacag tgatgagacc atctgcaata gatgtgaata tgaaacatga aagcacagtt    1080
ggattaagtg atttgaggca cttgggattt aatgaagtgg actttgggtg gggagatgca    1140
ttaaatgcaa gtctggtgca acatggggta attcaacaaa attattttct tttcctacaa    1200
ccttccaaga acatgaatgg tggaataaag atagcaatgt tcatgcccca atcaaaagtg    1260
aagccattca aaatagaaat ggaagcccta ataagcaaat atgcaactaa agtg          1314
```

<210> SEQ ID NO 60
<211> LENGTH: 438
<212> TYPE: PRT
<213> ORGANISM: Taxus cuspidata

<400> SEQUENCE: 60

```
Met Glu Lys Ala Gly Ser Ser Thr Glu Phe His Val Lys Ile Ser Asp
  1               5                  10                  15

Pro Val Met Val Pro Pro Cys Ile Pro Ser Pro Lys Thr Ile Leu Gln
                 20                  25                  30

Leu Ser Ala Val Asp Asn Tyr Pro Ala Val Arg Gly Asn Ile Leu Asp
             35                  40                  45

Cys Leu Leu Val Tyr Asn Ala Ser Asn Thr Ile Ser Ala Asp Pro Ala
         50                  55                  60

Thr Val Ile Arg Glu Ala Leu Ser Lys Val Leu Val Tyr Tyr Phe Pro
 65                  70                  75                  80

Phe Ala Gly Arg Met Arg Asn Lys Gly Asp Gly Glu Leu Glu Val Asp
                 85                  90                  95

Cys Thr Gly Glu Gly Ala Leu Phe Val Glu Ala Met Ala Asp Asp Asn
            100                 105                 110

Leu Ser Val Leu Gly Gly Phe Asp Tyr His Asn Pro Ala Phe Gly Lys
        115                 120                 125

Leu Leu Tyr Ser Leu Pro Leu Asp Thr Pro Ile His Asp Leu His Pro
    130                 135                 140

Leu Val Val Gln Val Thr Arg Phe Thr Cys Gly Gly Phe Val Val Gly
145                 150                 155                 160

Leu Ser Leu Asp His Ser Ile Cys Asp Gly Arg Gly Ala Gly Gln Phe
                165                 170                 175

Leu Lys Ala Leu Ala Glu Met Ala Arg Gly Glu Ala Lys Pro Ser Leu
            180                 185                 190

Glu Pro Ile Trp Asn Arg Glu Leu Leu Lys Pro Glu Asp Leu Ile Arg
        195                 200                 205

Leu Gln Phe Tyr His Phe Glu Ser Met Arg Pro Pro Ile Val Glu
    210                 215                 220

Glu Ile Val Gln Ala Ser Ile Ile Val Asn Ser Glu Thr Ile Ser Asn
225                 230                 235                 240

Ile Lys Gln Tyr Ile Met Glu Glu Cys Lys Glu Ser Ser Phe Ala Phe
                245                 250                 255

Glu Val Val Ala Ala Leu Ala Trp Leu Ala Arg Thr Arg Ala Phe Gln
            260                 265                 270

Ile Pro His Thr Glu Asn Val Lys Leu Leu Phe Ala Val Asp Thr Arg
        275                 280                 285

Arg Ser Phe Asp Pro Pro Leu Pro Lys Gly Tyr Tyr Gly Asn Ala Ala
    290                 295                 300

Gly Asn Ala Cys Ala Met Asp Asn Val Gln Asp Leu Leu Asn Gly Ser
305                 310                 315                 320
```

```
Leu Leu Arg Ala Val Met Ile Ile Lys Lys Ser Lys Val Ser Leu Asn
                325                 330                 335

Glu Asn Ile Arg Ala Lys Thr Val Met Arg Pro Ser Ala Ile Asp Val
            340                 345                 350

Asn Met Lys His Glu Ser Thr Val Gly Leu Ser Asp Leu Arg His Leu
        355                 360                 365

Gly Phe Asn Glu Val Asp Phe Gly Trp Gly Asp Ala Leu Asn Ala Ser
370                 375                 380

Leu Val Gln His Gly Val Ile Gln Gln Asn Tyr Phe Leu Phe Leu Gln
385                 390                 395                 400

Pro Ser Lys Asn Met Asn Gly Gly Ile Lys Ile Ala Met Phe Met Pro
            405                 410                 415

Gln Ser Lys Val Lys Pro Phe Lys Ile Glu Met Glu Ala Leu Ile Ser
        420                 425                 430

Lys Tyr Ala Thr Lys Val
        435

<210> SEQ ID NO 61
<211> LENGTH: 331
<212> TYPE: PRT
<213> ORGANISM: Arabidopsis thaliana

<400> SEQUENCE: 61

Met Ser Gln Ile Leu Glu Asn Pro Asn Pro Asn Glu Leu Asn Lys Leu
1               5                   10                  15

His Pro Phe Glu Phe His Glu Val Ser Asp Val Pro Leu Thr Val Gln
            20                  25                  30

Leu Thr Phe Phe Glu Cys Gly Gly Leu Ala Leu Gly Ile Gly Leu Ser
        35                  40                  45

His Lys Leu Cys Asp Ala Leu Ser Gly Leu Ile Phe Val Asn Ser Trp
    50                  55                  60

Ala Ala Phe Ala Arg Gly Gln Thr Asp Glu Ile Ile Thr Pro Ser Phe
65                  70                  75                  80

Asp Leu Ala Lys Met Phe Pro Pro Cys Asp Ile Glu Asn Leu Asn Met
                85                  90                  95

Ala Thr Gly Ile Thr Lys Glu Asn Ile Val Thr Arg Arg Phe Val Phe
            100                 105                 110

Leu Arg Ser Ser Val Glu Ser Leu Arg Glu Arg Phe Ser Gly Asn Lys
        115                 120                 125

Lys Ile Arg Ala Thr Arg Val Glu Val Leu Ser Val Phe Ile Trp Ser
    130                 135                 140

Arg Phe Met Ala Ser Thr Asn His Asp Asp Lys Thr Gly Lys Ile Tyr
145                 150                 155                 160

Thr Leu Ile His Pro Val Asn Leu Arg Arg Gln Ala Asp Pro Asp Ile
                165                 170                 175

Pro Asp Asn Met Phe Gly Asn Ile Met Arg Phe Ser Val Thr Val Pro
            180                 185                 190

Met Met Ile Ile Asn Glu Asn Asp Glu Glu Lys Ala Ser Leu Val Asp
        195                 200                 205

Gln Met Arg Glu Glu Ile Arg Lys Ile Asp Ala Val Tyr Val Lys Lys
    210                 215                 220

Leu Gln Glu Asp Asn Arg Gly His Leu Glu Phe Leu Asn Lys Gln Ala
225                 230                 235                 240

Ser Gly Phe Val Asn Gly Glu Ile Val Ser Phe Ser Phe Thr Ser Leu
```

```
                    245                 250                 255
Cys Lys Phe Pro Val Tyr Glu Ala Asp Phe Gly Trp Gly Lys Pro Leu
            260                 265                 270

Trp Val Ala Ser Ala Arg Met Ser Tyr Lys Asn Leu Val Ala Phe Ile
            275                 280                 285

Asp Thr Lys Glu Gly Asp Gly Ile Glu Ala Trp Ile Asn Leu Asp Gln
            290                 295                 300

Asn Asp Met Ser Arg Phe Glu Ala Asp Glu Glu Leu Leu Arg Tyr Val
305                 310                 315                 320

Ser Ser Asn Pro Ser Val Met Val Ser Val
            325                 330

<210> SEQ ID NO 62
<211> LENGTH: 436
<212> TYPE: PRT
<213> ORGANISM: Arabidopsis thaliana

<400> SEQUENCE: 62

Met Glu Lys Asn Val Glu Ile Leu Ser Arg Glu Ile Val Lys Pro Ser
1               5                   10                  15

Ser Pro Thr Pro Asp Asp Lys Arg Ile Leu Asn Leu Ser Leu Leu Asp
            20                  25                  30

Ile Leu Ser Ser Pro Met Tyr Thr Gly Ala Leu Leu Phe Tyr Ala Ala
        35                  40                  45

Asp Pro Gln Asn Leu Leu Gly Phe Ser Thr Glu Glu Thr Ser Leu Lys
    50                  55                  60

Leu Lys Lys Ser Leu Ser Lys Thr Leu Pro Ile Phe Tyr Pro Leu Ala
65                  70                  75                  80

Gly Arg Ile Ile Gly Ser Phe Val Glu Cys Asn Asp Glu Gly Ala Val
                85                  90                  95

Phe Ile Glu Ala Arg Val Asp His Leu Leu Ser Glu Phe Leu Lys Cys
            100                 105                 110

Pro Val Pro Glu Ser Leu Glu Leu Leu Ile Pro Val Glu Ala Lys Ser
        115                 120                 125

Arg Glu Ala Val Thr Trp Pro Val Leu Leu Ile Gln Ala Asn Phe Phe
    130                 135                 140

Ser Cys Gly Gly Leu Val Ile Thr Ile Cys Val Ser His Lys Ile Thr
145                 150                 155                 160

Asp Ala Thr Ser Leu Ala Met Phe Ile Arg Gly Trp Ala Glu Ser Ser
                165                 170                 175

Arg Gly Leu Gly Ile Thr Leu Ile Pro Ser Phe Thr Ala Ser Glu Val
            180                 185                 190

Phe Pro Lys Pro Leu Asp Glu Leu Pro Ser Lys Pro Met Asp Arg Lys
        195                 200                 205

Glu Glu Val Glu Met Ser Cys Val Thr Lys Arg Phe Val Phe Asp
    210                 215                 220

Ala Ser Lys Ile Lys Lys Leu Arg Ala Lys Ala Ser Arg Asn Leu Val
225                 230                 235                 240

Lys Asn Pro Thr Arg Val Glu Ala Val Thr Ala Leu Phe Trp Arg Cys
                245                 250                 255

Val Thr Lys Val Ser Arg Leu Ser Leu Thr Pro Arg Thr Ser Val
            260                 265                 270

Leu Gln Ile Leu Val Asn Leu Arg Gly Lys Val Asp Ser Leu Cys Glu
        275                 280                 285
```

```
Asn Thr Ile Gly Asn Met Leu Ser Leu Met Ile Leu Lys Asn Glu Glu
    290                 295                 300

Ala Ala Ile Glu Arg Ile Gln Asp Val Val Asp Glu Ile Arg Arg Ala
305                 310                 315                 320

Lys Glu Ile Phe Ser Leu Asn Cys Lys Glu Met Ser Lys Ser Ser Ser
                325                 330                 335

Arg Ile Phe Glu Leu Leu Glu Glu Ile Gly Lys Val Tyr Gly Arg Gly
            340                 345                 350

Asn Glu Met Asp Leu Trp Met Ser Asn Ser Trp Cys Lys Leu Gly Leu
        355                 360                 365

Tyr Asp Ala Asp Phe Gly Trp Gly Lys Pro Val Trp Val Thr Gly Arg
    370                 375                 380

Gly Thr Ser His Phe Lys Asn Leu Met Leu Leu Ile Asp Thr Lys Asp
385                 390                 395                 400

Gly Glu Gly Ile Glu Ala Trp Ile Thr Leu Thr Glu Glu Gln Met Ser
                405                 410                 415

Leu Phe Glu Cys Asp Gln Glu Leu Leu Glu Ser Ala Ser Leu Asn Pro
            420                 425                 430

Pro Val Leu Ile
            435

<210> SEQ ID NO 63
<211> LENGTH: 482
<212> TYPE: PRT
<213> ORGANISM: Arabidopsis thaliana

<400> SEQUENCE: 63

Met Pro Ser Leu Glu Lys Ser Val Thr Ile Ile Ser Arg Asn Arg Val
1               5                   10                  15

Phe Pro Asp Gln Lys Ser Thr Leu Val Asp Leu Lys Leu Ser Val Ser
                20                  25                  30

Asp Leu Pro Met Leu Ser Cys His Tyr Ile Gln Lys Gly Cys Leu Phe
            35                  40                  45

Thr Cys Pro Asn Leu Pro Leu Pro Ala Leu Ile Ser His Leu Lys His
    50                  55                  60

Ser Leu Ser Ile Thr Leu Thr His Phe Pro Pro Leu Ala Gly Arg Leu
65                  70                  75                  80

Ser Thr Ser Ser Ser Gly His Val Phe Leu Thr Cys Asn Asp Ala Gly
                85                  90                  95

Ala Asp Phe Val Phe Ala Gln Ala Lys Ser Ile His Val Ser Asp Val
                100                 105                 110

Ile Ala Gly Ile Asp Val Pro Asp Val Val Lys Glu Phe Phe Thr Tyr
            115                 120                 125

Asp Arg Ala Val Ser Tyr Glu Gly His Asn Arg Pro Ile Leu Ala Val
    130                 135                 140

Gln Val Thr Glu Leu Asn Asp Gly Val Phe Ile Gly Cys Ser Val Asn
145                 150                 155                 160

His Ala Val Thr Asp Gly Thr Ser Leu Trp Asn Phe Ile Asn Thr Phe
                165                 170                 175

Ala Glu Val Ser Arg Gly Ala Lys Asn Val Thr Arg Gln Pro Asp Phe
            180                 185                 190

Thr Arg Glu Ser Val Leu Ile Ser Pro Ala Val Leu Lys Val Pro Gln
    195                 200                 205

Gly Gly Pro Lys Val Thr Phe Asp Glu Asn Ala Pro Leu Arg Glu Arg
210                 215                 220
```

-continued

```
Ile Phe Ser Phe Ser Arg Glu Ser Ile Gln Glu Leu Lys Ala Val Val
225                 230                 235                 240

Asn Lys Lys Lys Trp Leu Thr Val Asp Asn Gly Glu Ile Asp Gly Val
                245                 250                 255

Glu Leu Leu Gly Lys Gln Ser Asn Asp Lys Leu Asn Gly Lys Glu Asn
            260                 265                 270

Gly Ile Leu Thr Glu Met Leu Glu Ser Leu Phe Gly Arg Asn Asp Ala
        275                 280                 285

Val Ser Lys Pro Val Ala Val Glu Ile Ser Ser Phe Gln Ser Leu Cys
    290                 295                 300

Ala Leu Leu Trp Arg Ala Ile Thr Arg Ala Arg Lys Leu Pro Ser Ser
305                 310                 315                 320

Lys Thr Thr Thr Phe Arg Met Ala Val Asn Cys Arg His Arg Leu Ser
                325                 330                 335

Pro Lys Leu Asn Pro Glu Tyr Phe Gly Asn Ala Ile Gln Ser Val Pro
            340                 345                 350

Thr Phe Ala Thr Ala Ala Glu Val Leu Ser Arg Asp Leu Lys Trp Cys
        355                 360                 365

Ala Asp Gln Leu Asn Gln Ser Val Ala Ala His Gln Asp Gly Arg Ile
    370                 375                 380

Arg Ser Val Val Ala Asp Trp Glu Ala Asn Pro Arg Cys Phe Pro Leu
385                 390                 395                 400

Gly Asn Ala Asp Gly Ala Ser Val Thr Met Gly Ser Ser Pro Arg Phe
                405                 410                 415

Pro Met Tyr Asp Asn Asp Phe Gly Trp Gly Arg Pro Val Ala Val Arg
            420                 425                 430

Ser Gly Arg Ser Asn Lys Phe Asp Gly Lys Ile Ser Ala Phe Pro Gly
        435                 440                 445

Arg Glu Gly Asn Gly Thr Val Asp Leu Glu Val Val Leu Ser Pro Glu
    450                 455                 460

Thr Met Ala Gly Ile Glu Ser Asp Gly Glu Phe Met Arg Tyr Val Thr
465                 470                 475                 480

Asn Lys
```

```
<210> SEQ ID NO 64
<211> LENGTH: 461
<212> TYPE: PRT
<213> ORGANISM: Arabidopsis thaliana

<400> SEQUENCE: 64
```

```
Met Ala Ser Cys Ile Gln Glu Leu His Phe Thr His Leu His Ile Pro
1               5                   10                  15

Val Thr Ile Asn Gln Gln Phe Leu Val His Pro Ser Ser Pro Thr Pro
                20                  25                  30

Ala Asn Gln Ser Pro His His Ser Leu Tyr Leu Ser Asn Leu Asp Asp
            35                  40                  45

Ile Ile Gly Ala Arg Val Phe Thr Pro Ser Val Tyr Phe Tyr Pro Ser
        50                  55                  60

Thr Asn Asn Arg Glu Ser Phe Val Leu Lys Arg Leu Gln Asp Ala Leu
65                  70                  75                  80

Ser Glu Val Leu Val Pro Tyr Tyr Pro Leu Ser Gly Arg Leu Arg Glu
                85                  90                  95

Val Glu Asn Gly Lys Leu Glu Val Phe Phe Gly Glu Glu Gln Gly Val
            100                 105                 110
```

```
Leu Met Val Ser Ala Asn Ser Ser Met Asp Leu Ala Asp Leu Gly Asp
        115                 120                 125

Leu Thr Val Pro Asn Pro Ala Trp Leu Pro Leu Ile Phe Arg Asn Pro
        130                 135                 140

Gly Glu Glu Ala Tyr Lys Ile Leu Glu Met Pro Leu Leu Ile Ala Gln
145                 150                 155                 160

Val Thr Phe Phe Thr Cys Gly Phe Ser Leu Gly Ile Arg Leu Cys
                    165                 170                 175

His Cys Ile Cys Asp Gly Phe Gly Ala Met Gln Phe Leu Gly Ser Trp
                180                 185                 190

Ala Ala Thr Ala Lys Thr Gly Lys Leu Ile Ala Asp Pro Glu Pro Val
            195                 200                 205

Trp Asp Arg Glu Thr Phe Lys Pro Arg Asn Pro Met Val Lys Tyr
        210                 215                 220

Pro His His Glu Tyr Leu Pro Ile Glu Arg Ser Asn Leu Thr Asn
225                 230                 235                 240

Ser Leu Trp Asp Thr Lys Pro Leu Gln Lys Cys Tyr Arg Ile Ser Lys
                    245                 250                 255

Glu Phe Gln Cys Arg Val Lys Ser Ile Ala Gln Gly Glu Asp Pro Thr
                260                 265                 270

Leu Val Cys Ser Thr Phe Asp Ala Met Ala Ala His Ile Trp Arg Ser
            275                 280                 285

Trp Val Lys Ala Leu Asp Val Lys Pro Leu Asp Tyr Asn Leu Arg Leu
        290                 295                 300

Thr Phe Ser Val Asn Val Arg Thr Arg Leu Glu Thr Leu Lys Leu Arg
305                 310                 315                 320

Lys Gly Phe Tyr Gly Asn Val Val Cys Leu Ala Cys Ala Met Ser Ser
                    325                 330                 335

Val Glu Ser Leu Ile Asn Asp Ser Leu Ser Lys Thr Thr Arg Leu Val
                340                 345                 350

Gln Asp Ala Arg Leu Arg Val Ser Glu Asp Tyr Leu Arg Ser Met Val
            355                 360                 365

Asp Tyr Val Asp Val Lys Arg Pro Lys Arg Leu Glu Phe Gly Gly Lys
        370                 375                 380

Leu Thr Ile Thr Gln Trp Thr Arg Phe Glu Met Tyr Glu Thr Ala Asp
385                 390                 395                 400

Phe Gly Trp Gly Lys Pro Val Tyr Ala Gly Pro Ile Asp Leu Arg Pro
                    405                 410                 415

Thr Pro Gln Val Cys Val Leu Leu Pro Gln Gly Gly Val Glu Ser Gly
                420                 425                 430

Asn Asp Gln Ser Met Val Val Cys Leu Cys Leu Pro Pro Thr Ala Val
            435                 440                 445

His Thr Phe Thr Arg Leu Leu Ser Leu Asn Asp His Lys
        450                 455                 460

<210> SEQ ID NO 65
<211> LENGTH: 572
<212> TYPE: PRT
<213> ORGANISM: Arabidopsis thaliana

<400> SEQUENCE: 65

Met Ala Ala Val Ser Val Ala Ser Ala Glu Leu Pro Pro Pro Gln
1               5                   10                  15

Asp Gly Glu Thr Leu Ser Asn Val Pro Gln Thr Leu Ser Gly Glu Asp
```

-continued

```
                 20                  25                  30
Cys Lys Lys Gln Arg Ile Gln Arg Pro Lys Ser Lys Asn Ala Glu Lys
     35                  40                  45

Cys Thr Val Lys Cys Val Asn Thr Cys Ile Arg Ser Gly Asp Gly Glu
 50                  55                  60

Gly Pro Ile Asn Ile Arg Arg Phe Gln Arg Ile Ala Trp Gln Ile Glu
65                  70                  75                  80

Gly Ile Gln Val Thr Val Ser Cys Phe Phe Val Thr Cys Gly Lys Thr
                 85                  90                  95

Arg Ser Ser Ser Asn Asn Pro His His Thr Thr Phe Phe Ile Leu Ser
            100                 105                 110

Glu Asn Asn Gln Met Gly Glu Ala Ala Glu Gln Ala Arg Gly Phe
            115                 120                 125

His Val Thr Thr Thr Arg Lys Gln Val Ile Thr Ala Ala Leu Pro Leu
            130                 135                 140

Gln Asp His Trp Leu Pro Leu Ser Asn Leu Asp Leu Leu Pro Pro
145                 150                 155                 160

Leu Asn Val His Val Cys Phe Cys Tyr Lys Lys Pro Leu His Phe Thr
                 165                 170                 175

Asn Thr Val Ala Tyr Glu Thr Leu Lys Thr Ala Leu Ala Glu Thr Leu
            180                 185                 190

Val Ser Tyr Tyr Ala Phe Ala Gly Glu Leu Val Thr Asn Pro Thr Gly
            195                 200                 205

Glu Pro Glu Ile Leu Cys Asn Asn Arg Gly Val Asp Phe Val Glu Ala
210                 215                 220

Gly Ala Asp Val Glu Leu Arg Glu Leu Asn Leu Tyr Asp Pro Asp Glu
225                 230                 235                 240

Ser Ile Ala Lys Leu Val Pro Ile Lys Lys His Gly Val Ile Ala Ile
                 245                 250                 255

Gln Val Thr Gln Leu Lys Cys Gly Ser Ile Val Val Gly Cys Thr Phe
            260                 265                 270

Asp His Arg Val Ala Asp Ala Tyr Ser Met Asn Met Phe Leu Leu Ser
            275                 280                 285

Trp Ala Glu Ile Ser Arg Ser Asp Val Pro Ile Ser Cys Val Pro Ser
290                 295                 300

Phe Arg Arg Ser Leu Leu Asn Pro Arg Arg Pro Leu Val Met Asp Pro
305                 310                 315                 320

Ser Ile Asp Gln Ile Tyr Met Pro Val Thr Ser Leu Pro Pro Gln
                 325                 330                 335

Glu Thr Thr Asn Pro Glu Asn Leu Leu Ala Ser Arg Ile Tyr Tyr Ile
            340                 345                 350

Lys Ala Asn Ala Leu Gln Glu Leu Gln Thr Leu Ala Ser Ser Ser Lys
            355                 360                 365

Asn Gly Lys Arg Thr Lys Leu Glu Ser Phe Ser Ala Phe Leu Trp Lys
            370                 375                 380

Leu Val Ala Glu His Ala Ala Lys Asp Pro Val Pro Ile Lys Thr Ser
385                 390                 395                 400

Lys Leu Gly Ile Val Val Asp Gly Arg Arg Leu Met Glu Lys Glu
                 405                 410                 415

Asn Asn Thr Tyr Phe Gly Asn Val Leu Ser Val Pro Phe Gly Gly Gln
            420                 425                 430

Arg Ile Asp Asp Leu Ile Ser Lys Pro Leu Ser Trp Val Thr Glu Glu
            435                 440                 445
```

```
Val His Arg Phe Leu Lys Lys Ser Val Thr Lys Glu His Phe Leu Asn
450                 455                 460

Leu Ile Asp Trp Val Glu Thr Cys Arg Pro Thr Pro Ala Val Ser Arg
465                 470                 475                 480

Ile Tyr Ser Val Gly Ser Asp Asp Gly Pro Ala Phe Val Val Ser Ser
                485                 490                 495

Gly Arg Ser Phe Pro Val Asn Gln Val Asp Phe Gly Trp Gly Ser Pro
            500                 505                 510

Val Phe Gly Ser Tyr His Phe Pro Trp Gly Gly Ser Ala Gly Tyr Val
            515                 520                 525

Met Pro Met Pro Ser Ser Val Asp Asp Arg Asp Trp Met Val Tyr Leu
            530                 535                 540

His Leu Thr Lys Gly Gln Leu Arg Phe Ile Glu Glu Ala Ser His
545                 550                 555                 560

Val Leu Lys Pro Ile Asp Asn Asp Tyr Leu Lys Ile
                565                 570

<210> SEQ ID NO 66
<211> LENGTH: 433
<212> TYPE: PRT
<213> ORGANISM: Clarkia breweri

<400> SEQUENCE: 66

Met Asn Val Thr Met His Ser Lys Lys Leu Leu Lys Pro Ser Ile Pro
1               5                   10                  15

Thr Pro Asn His Leu Gln Lys Leu Asn Leu Ser Leu Leu Asp Gln Ile
                20                  25                  30

Gln Ile Pro Phe Tyr Val Gly Leu Ile Phe His Tyr Glu Thr Leu Ser
            35                  40                  45

Asp Asn Ser Asp Ile Thr Leu Ser Lys Leu Glu Ser Ser Leu Ser Glu
        50                  55                  60

Thr Leu Thr Leu Tyr Tyr His Val Ala Gly Arg Tyr Asn Gly Thr Asp
65                  70                  75                  80

Cys Val Ile Glu Cys Asn Asp Gln Gly Ile Gly Tyr Val Glu Thr Ala
                85                  90                  95

Phe Asp Val Glu Leu His Gln Phe Leu Leu Gly Glu Glu Ser Asn Asn
            100                 105                 110

Leu Asp Leu Leu Val Gly Leu Ser Gly Phe Leu Ser Glu Thr Glu Thr
        115                 120                 125

Pro Pro Leu Ala Ala Ile Gln Leu Asn Met Phe Lys Cys Gly Gly Leu
    130                 135                 140

Val Ile Gly Ala Gln Phe Asn His Ile Ile Gly Asp Met Phe Thr Met
145                 150                 155                 160

Ser Thr Phe Met Asn Ser Trp Ala Lys Ala Cys Arg Val Gly Ile Lys
                165                 170                 175

Glu Val Ala His Pro Thr Phe Gly Leu Ala Pro Leu Met Pro Ser Ala
            180                 185                 190

Lys Val Leu Asn Ile Pro Pro Pro Ser Phe Glu Gly Val Lys Phe
        195                 200                 205

Val Ser Lys Arg Phe Val Phe Asn Glu Asn Ala Ile Thr Arg Leu Arg
    210                 215                 220

Lys Glu Ala Thr Glu Glu Asp Gly Asp Gly Asp Asp Gln Lys Lys
225                 230                 235                 240

Lys Arg Pro Ser Arg Val Asp Leu Val Thr Ala Phe Leu Ser Lys Ser
```

```
                245             250             255
Leu Ile Glu Met Asp Cys Ala Lys Lys Glu Gln Thr Lys Ser Arg Pro
            260                 265                 270

Ser Leu Met Val His Met Met Asn Leu Arg Lys Arg Thr Lys Leu Ala
            275                 280                 285

Leu Glu Asn Asp Val Ser Gly Asn Phe Phe Ile Val Asn Ala Glu
            290                 295                 300

Ser Lys Ile Thr Val Ala Pro Lys Ile Thr Asp Leu Thr Glu Ser Leu
305                 310                 315                 320

Gly Ser Ala Cys Gly Glu Ile Ile Ser Glu Val Ala Lys Val Asp Asp
                325                 330                 335

Ala Glu Val Val Ser Ser Met Val Leu Asn Ser Val Arg Glu Phe Tyr
            340                 345                 350

Tyr Glu Trp Gly Lys Gly Glu Lys Asn Val Phe Leu Tyr Thr Ser Trp
            355                 360                 365

Cys Arg Phe Pro Leu Tyr Glu Val Asp Phe Gly Trp Gly Ile Pro Ser
            370                 375                 380

Leu Val Asp Thr Thr Ala Val Pro Phe Gly Leu Ile Val Leu Met Asp
385                 390                 395                 400

Glu Ala Pro Ala Gly Asp Gly Ile Ala Val Arg Ala Cys Leu Ser Glu
                405                 410                 415

His Asp Met Ile Gln Phe Gln Gln His His Gln Leu Leu Ser Tyr Val
            420                 425                 430

Ser

<210> SEQ ID NO 67
<211> LENGTH: 450
<212> TYPE: PRT
<213> ORGANISM: Dianthus caryophyllus

<400> SEQUENCE: 67

Met Gly Ser Ser Tyr Gln Glu Ser Pro Leu Leu Leu Glu Asp Leu
1               5                   10                  15

Lys Val Thr Ile Lys Glu Ser Thr Leu Ile Phe Pro Ser Glu Glu Thr
            20                  25                  30

Ser Glu Arg Lys Ser Met Phe Leu Ser Asn Val Asp Gln Ile Leu Asn
            35                  40                  45

Phe Asp Val Gln Thr Val His Phe Phe Arg Pro Asn Lys Glu Phe Pro
    50                  55                  60

Pro Glu Met Val Ser Glu Lys Leu Arg Lys Ala Leu Val Lys Leu Met
65                  70                  75                  80

Asp Ala Tyr Glu Phe Leu Ala Gly Arg Leu Arg Val Asp Pro Ser Ser
                85                  90                  95

Gly Arg Leu Asp Val Asp Cys Asn Gly Ala Gly Ala Gly Phe Val Thr
            100                 105                 110

Ala Ala Ser Asp Tyr Thr Leu Glu Glu Leu Gly Asp Leu Val Tyr Pro
            115                 120                 125

Asn Pro Ala Phe Ala Gln Leu Val Thr Ser Gln Leu Gln Ser Leu Pro
            130                 135                 140

Lys Asp Asp Gln Pro Leu Phe Val Phe Gln Ile Thr Ser Phe Lys Cys
145                 150                 155                 160

Gly Gly Phe Ala Met Gly Ile Ser Thr Asn His Thr Thr Phe Asp Gly
                165                 170                 175

Leu Ser Phe Lys Thr Phe Leu Glu Asn Leu Ala Ser Leu Leu His Glu
```

```
                    180                 185                 190
Lys Pro Leu Ser Thr Pro Pro Cys Asn Asp Arg Thr Leu Leu Lys Ala
            195                 200                 205

Arg Asp Pro Pro Ser Val Ala Phe Pro His His Glu Leu Val Lys Phe
210                 215                 220

Gln Asp Cys Glu Thr Thr Thr Val Phe Glu Ala Thr Ser Glu His Leu
225                 230                 235                 240

Asp Phe Lys Ile Phe Lys Leu Ser Ser Glu Gln Ile Lys Lys Leu Lys
                245                 250                 255

Glu Arg Ala Ser Glu Thr Ser Asn Gly Asn Val Arg Val Thr Gly Phe
            260                 265                 270

Asn Val Val Thr Ala Leu Val Trp Arg Cys Lys Ala Leu Ser Val Ala
            275                 280                 285

Ala Glu Glu Gly Glu Thr Asn Leu Glu Arg Glu Ser Thr Ile Leu
        290                 295                 300

Tyr Ala Val Asp Ile Arg Gly Arg Leu Asn Pro Glu Leu Pro Pro Ser
305                 310                 315                 320

Tyr Thr Gly Asn Ala Val Leu Thr Ala Tyr Ala Lys Glu Lys Cys Lys
                325                 330                 335

Ala Leu Leu Glu Glu Pro Phe Gly Arg Ile Val Glu Met Val Gly Glu
            340                 345                 350

Gly Ser Lys Arg Ile Thr Asp Glu Tyr Ala Arg Ser Ala Ile Asp Trp
            355                 360                 365

Gly Glu Leu Tyr Lys Gly Phe Pro His Gly Glu Val Leu Val Ser Ser
        370                 375                 380

Trp Trp Lys Leu Gly Phe Ala Glu Val Glu Tyr Pro Trp Gly Lys Pro
385                 390                 395                 400

Lys Tyr Ser Cys Pro Val Val Tyr His Arg Lys Asp Ile Val Leu Leu
                405                 410                 415

Phe Pro Asp Ile Asp Gly Asp Ser Lys Gly Val Tyr Val Leu Ala Ala
            420                 425                 430

Leu Pro Ser Lys Glu Met Ser Lys Phe Gln His Trp Phe Glu Asp Thr
            435                 440                 445

Leu Cys
    450

<210> SEQ ID NO 68
<211> LENGTH: 439
<212> TYPE: PRT
<213> ORGANISM: Catharanthus roseus

<400> SEQUENCE: 68

Met Glu Ser Gly Lys Ile Ser Val Glu Thr Glu Thr Leu Ser Lys Thr
1               5                   10                  15

Leu Ile Lys Pro Ser Ser Pro Thr Pro Gln Ser Leu Ser Arg Tyr Asn
            20                  25                  30

Leu Ser Tyr Asn Asp Gln Asn Ile Tyr Gln Thr Cys Val Ser Val Gly
        35                  40                  45

Phe Phe Tyr Glu Asn Pro Asp Gly Ile Glu Ile Ser Thr Ile Arg Glu
    50                  55                  60

Gln Leu Gln Asn Ser Leu Ser Lys Thr Leu Val Ser Tyr Tyr Pro Phe
65                  70                  75                  80

Ala Gly Lys Val Val Lys Asn Asp Tyr Ile His Cys Asn Asp Asp Gly
                85                  90                  95
```

```
Ile Glu Phe Val Glu Val Arg Ile Arg Cys Arg Met Asn Asp Ile Leu
            100                 105                 110

Lys Tyr Glu Leu Arg Ser Tyr Ala Arg Asp Leu Val Leu Pro Lys Arg
            115                 120                 125

Val Thr Val Gly Ser Asp Thr Thr Ala Ile Val Gln Leu Ser His
    130                 135                 140

Phe Asp Cys Gly Gly Leu Ala Val Ala Phe Gly Ile Ser His Lys Val
145                 150                 155                 160

Ala Asp Gly Gly Thr Ile Ala Ser Phe Met Lys Asp Trp Ala Ala Ser
                165                 170                 175

Ala Cys Tyr Leu Ser Ser Ser His His Val Pro Thr Pro Leu Leu Val
            180                 185                 190

Ser Asp Ser Ile Phe Pro Arg Gln Asp Asn Ile Ile Cys Glu Gln Phe
            195                 200                 205

Pro Thr Ser Lys Asn Cys Val Glu Lys Thr Phe Ile Phe Pro Pro Glu
        210                 215                 220

Ala Ile Glu Lys Leu Lys Ser Lys Ala Val Glu Phe Gly Ile Glu Lys
225                 230                 235                 240

Pro Thr Arg Val Glu Val Leu Thr Ala Phe Leu Ser Arg Cys Ala Thr
                245                 250                 255

Val Ala Gly Lys Ser Ala Ala Lys Asn Asn Asn Cys Gly Gln Ser Leu
            260                 265                 270

Pro Phe Pro Val Leu Gln Ala Ile Asn Leu Arg Pro Ile Leu Glu Leu
        275                 280                 285

Pro Gln Asn Ser Val Gly Asn Leu Val Ser Ile Tyr Phe Ser Arg Thr
    290                 295                 300

Ile Lys Glu Asn Asp Tyr Leu Asn Glu Lys Tyr Thr Lys Leu Val
305                 310                 315                 320

Ile Asn Glu Leu Arg Lys Glu Lys Gln Lys Ile Lys Asn Leu Ser Arg
                325                 330                 335

Glu Lys Leu Thr Tyr Val Ala Gln Met Glu Glu Phe Val Lys Ser Leu
            340                 345                 350

Lys Glu Phe Asp Ile Ser Asn Phe Leu Asp Ile Asp Ala Tyr Leu Ser
        355                 360                 365

Asp Ser Trp Cys Arg Phe Pro Phe Tyr Asp Val Asp Phe Gly Trp Gly
    370                 375                 380

Lys Pro Ile Trp Val Cys Leu Phe Gln Pro Tyr Ile Lys Asn Cys Val
385                 390                 395                 400

Val Met Met Asp Tyr Pro Phe Gly Asp Tyr Gly Ile Glu Ala Ile
                405                 410                 415

Val Ser Phe Glu Gln Glu Lys Met Ser Ala Phe Glu Lys Asn Glu Gln
            420                 425                 430

Leu Leu Gln Phe Val Ser Asn
        435
```

<210> SEQ ID NO 69
<211> LENGTH: 451
<212> TYPE: PRT
<213> ORGANISM: Arabidopsis thaliana

<400> SEQUENCE: 69

```
Met Ala Pro Ile Thr Phe Arg Lys Ser Tyr Thr Ile Val Pro Ala Glu
  1               5                  10                  15

Pro Thr Trp Ser Gly Arg Phe Pro Leu Ala Glu Trp Asp Gln Val Gly
             20                  25                  30
```

```
Thr Ile Thr His Ile Pro Thr Leu Tyr Phe Tyr Asp Lys Pro Ser Glu
         35                  40                  45

Ser Phe Gln Gly Asn Val Val Glu Ile Leu Lys Thr Ser Leu Ser Arg
     50                  55                  60

Val Leu Val His Phe Tyr Pro Met Ala Gly Arg Leu Arg Trp Leu Pro
 65              70                  75                      80

Arg Gly Arg Phe Glu Leu Asn Cys Asn Ala Glu Gly Val Glu Phe Ile
                 85                  90                  95

Glu Ala Glu Ser Glu Gly Lys Leu Ser Asp Phe Lys Asp Phe Ser Pro
             100                 105                 110

Thr Pro Glu Phe Glu Asn Leu Met Pro Gln Val Asn Tyr Lys Asn Pro
             115                 120                 125

Ile Glu Thr Ile Pro Leu Phe Leu Ala Gln Val Thr Lys Phe Lys Cys
         130                 135                 140

Gly Gly Ile Ser Leu Ser Val Asn Val Ser His Ala Ile Val Asp Gly
145                 150                 155                 160

Gln Ser Ala Leu His Leu Ile Ser Glu Trp Gly Arg Leu Ala Arg Gly
                 165                 170                 175

Glu Pro Leu Glu Thr Val Pro Phe Leu Asp Arg Lys Ile Leu Trp Ala
             180                 185                 190

Gly Glu Pro Leu Pro Pro Phe Val Ser Pro Lys Phe Asp His Lys
             195                 200                 205

Glu Phe Asp Gln Pro Pro Phe Leu Ile Gly Glu Thr Asp Asn Val Glu
             210                 215                 220

Glu Arg Lys Lys Lys Thr Ile Val Val Met Leu Pro Leu Ser Thr Ser
225                 230                 235                 240

Gln Leu Gln Lys Leu Arg Ser Lys Ala Asn Gly Ser Lys His Ser Asp
                 245                 250                 255

Pro Ala Lys Gly Phe Thr Arg Tyr Glu Thr Val Thr Gly His Val Trp
             260                 265                 270

Arg Cys Ala Cys Lys Ala Arg Gly His Ser Pro Glu Gln Pro Thr Ala
275                 280                 285

Leu Gly Ile Cys Ile Asp Thr Arg Ser Arg Met Glu Pro Pro Leu Pro
         290                 295                 300

Arg Gly Tyr Phe Gly Asn Ala Thr Leu Asp Val Val Ala Ala Ser Thr
305                 310                 315                 320

Ser Gly Glu Leu Ile Ser Asn Glu Leu Gly Phe Ala Ala Ser Leu Ile
                 325                 330                 335

Ser Lys Ala Ile Lys Asn Val Thr Asn Glu Tyr Val Met Ile Gly Ile
             340                 345                 350

Glu Tyr Leu Lys Asn Gln Lys Asp Leu Lys Lys Phe Gln Asp Leu His
         355                 360                 365

Ala Leu Gly Ser Thr Glu Gly Pro Phe Tyr Gly Asn Pro Asn Leu Gly
         370                 375                 380

Val Val Ser Trp Leu Thr Leu Pro Met Tyr Gly Leu Asp Phe Gly Trp
385                 390                 395                 400

Gly Lys Glu Phe Tyr Thr Gly Pro Gly Thr His Asp Phe Asp Gly Asp
                 405                 410                 415

Ser Leu Ile Leu Pro Asp Gln Asn Glu Asp Gly Ser Val Ile Leu Ala
             420                 425                 430

Thr Cys Leu Gln Val Ala His Met Glu Ala Phe Lys Lys His Phe Tyr
         435                 440                 445
```

```
Glu Asp Ile
    450

<210> SEQ ID NO 70
<211> LENGTH: 461
<212> TYPE: PRT
<213> ORGANISM: Arabidopsis thaliana

<400> SEQUENCE: 70

Met Ala Asn Gln Arg Lys Pro Ile Leu Pro Leu Leu Glu Lys Lys
  1               5                  10                  15

Pro Val Glu Leu Val Lys Pro Ser Lys His Thr His Cys Glu Thr Leu
             20                  25                  30

Ser Leu Ser Thr Leu Asp Asn Asp Pro Phe Asn Glu Val Met Tyr Ala
             35                  40                  45

Thr Ile Tyr Val Phe Lys Ala Asn Gly Lys Asn Leu Asp Asp Pro Val
         50                  55                  60

Ser Leu Leu Arg Lys Ala Leu Ser Glu Leu Val His Tyr Tyr Pro
 65                  70                  75                  80

Leu Ser Gly Lys Leu Met Arg Ser Glu Ser Asn Gly Lys Leu Gln Leu
                 85                  90                  95

Val Tyr Leu Gly Glu Gly Val Pro Phe Glu Val Ala Thr Ser Thr Leu
                100                 105                 110

Asp Leu Ser Ser Leu Asn Tyr Ile Glu Asn Leu Asp Asp Gln Val Ala
             115                 120                 125

Leu Arg Leu Val Pro Glu Ile Glu Ile Asp Tyr Glu Ser Asn Val Cys
    130                 135                 140

Tyr His Pro Leu Ala Leu Gln Val Thr Lys Phe Ala Cys Gly Gly Phe
145                 150                 155                 160

Thr Ile Gly Thr Ala Leu Thr His Ala Val Cys Asp Gly Tyr Gly Val
                165                 170                 175

Ala Gln Ile Ile His Ala Leu Thr Glu Leu Ala Ala Gly Lys Thr Glu
            180                 185                 190

Pro Ser Val Lys Ser Val Trp Gln Arg Glu Arg Leu Val Gly Lys Ile
        195                 200                 205

Asp Asn Lys Pro Gly Lys Val Pro Gly Ser His Ile Asp Gly Phe Leu
    210                 215                 220

Ala Thr Ser Ala Tyr Leu Pro Thr Thr Asp Val Val Thr Glu Thr Ile
225                 230                 235                 240

Asn Ile Arg Ala Gly Asp Ile Lys Arg Leu Lys Asp Ser Met Met Lys
                245                 250                 255

Glu Cys Glu Tyr Leu Lys Glu Ser Phe Thr Thr Tyr Glu Val Leu Ser
            260                 265                 270

Ser Tyr Ile Trp Lys Leu Arg Ser Arg Ala Leu Lys Leu Asn Pro Asp
        275                 280                 285

Gly Ile Thr Val Leu Gly Val Ala Val Gly Ile Arg His Val Leu Asp
    290                 295                 300

Pro Pro Leu Pro Lys Gly Tyr Tyr Gly Asn Ala Tyr Ile Asp Val Tyr
305                 310                 315                 320

Val Glu Leu Thr Val Arg Glu Leu Glu Ser Ser Ile Ser Asn Ile
                325                 330                 335

Ala Asn Arg Val Lys Lys Ala Lys Lys Thr Ala Tyr Glu Lys Gly Tyr
            340                 345                 350

Ile Glu Glu Glu Leu Lys Asn Thr Glu Arg Leu Met Arg Asp Asp Ser
        355                 360                 365
```

-continued

```
Met Phe Glu Gly Val Ser Asp Gly Leu Phe Leu Thr Asp Trp Arg
    370                 375                 380

Asn Ile Gly Trp Phe Gly Ser Met Asp Phe Gly Trp Asn Glu Pro Val
385                 390                 395                 400

Asn Leu Arg Pro Leu Thr Gln Arg Glu Ser Thr Val His Val Gly Met
                405                 410                 415

Ile Leu Lys Pro Ser Lys Ser Asp Pro Ser Met Glu Gly Val Lys
                420                 425                 430

Val Ile Met Lys Leu Pro Arg Asp Ala Met Val Glu Phe Lys Arg Glu
                435                 440                 445

Met Ala Thr Met Lys Lys Leu Tyr Phe Gly Asp Thr Asn
    450                 455                 460

<210> SEQ ID NO 71
<211> LENGTH: 460
<212> TYPE: PRT
<213> ORGANISM: Nicotiana tabacum

<400> SEQUENCE: 71

Met Asp Ser Lys Gln Ser Ser Glu Leu Val Phe Thr Val Arg Arg Gln
1               5                   10                  15

Lys Pro Glu Leu Ile Ala Pro Ala Lys Pro Thr Pro Arg Glu Thr Lys
                20                  25                  30

Phe Leu Ser Asp Ile Asp Gln Glu Gly Leu Arg Phe Gln Ile Pro
            35                  40                  45

Val Ile Gln Phe Tyr His Lys Asp Ser Ser Met Gly Arg Lys Asp Pro
        50                  55                  60

Val Lys Val Ile Lys Lys Ala Ile Ala Glu Thr Leu Val Phe Tyr Tyr
65                  70                  75                  80

Pro Phe Ala Gly Arg Leu Arg Glu Gly Asn Gly Arg Lys Leu Met Val
                85                  90                  95

Asp Cys Thr Gly Glu Gly Ile Met Phe Val Glu Ala Asp Ala Asp Val
                100                 105                 110

Thr Leu Glu Gln Phe Gly Asp Glu Leu Gln Pro Pro Phe Pro Cys Leu
            115                 120                 125

Glu Glu Leu Leu Tyr Asp Val Pro Asp Ser Ala Gly Val Leu Asn Cys
        130                 135                 140

Pro Leu Leu Leu Ile Gln Val Thr Arg Leu Arg Cys Gly Gly Phe Ile
145                 150                 155                 160

Phe Ala Leu Arg Leu Asn His Thr Met Ser Asp Ala Pro Gly Leu Val
                165                 170                 175

Gln Phe Met Thr Ala Val Gly Glu Met Ala Arg Gly Gly Ser Ala Pro
            180                 185                 190

Ser Ile Leu Pro Val Trp Cys Arg Glu Leu Leu Asn Ala Arg Asn Pro
        195                 200                 205

Pro Gln Val Thr Cys Thr His His Glu Tyr Asp Glu Val Arg Asp Thr
    210                 215                 220

Lys Gly Thr Ile Ile Pro Leu Asp Asp Met Val His Lys Ser Phe Phe
225                 230                 235                 240

Phe Gly Pro Ser Glu Val Ser Ala Leu Arg Arg Phe Val Pro His His
                245                 250                 255

Leu Arg Lys Cys Ser Thr Phe Glu Leu Leu Thr Ala Val Leu Trp Arg
            260                 265                 270

Cys Arg Thr Met Ser Leu Lys Pro Asp Pro Glu Glu Glu Val Arg Ala
```

```
                275                 280                 285
Leu Cys Ile Val Asn Ala Arg Ser Arg Phe Asn Pro Pro Leu Pro Thr
            290                 295                 300
Gly Tyr Tyr Gly Asn Ala Phe Ala Phe Pro Val Ala Val Thr Thr Ala
305                 310                 315                 320
Ala Lys Leu Ser Lys Asn Pro Leu Gly Tyr Ala Leu Glu Leu Val Lys
                325                 330                 335
Lys Thr Lys Ser Asp Val Thr Glu Glu Tyr Met Lys Ser Val Ala Asp
                340                 345                 350
Leu Met Val Leu Lys Gly Arg Pro His Phe Thr Val Val Arg Thr Phe
                355                 360                 365
Leu Val Ser Asp Val Thr Arg Gly Gly Phe Glu Val Asp Phe Gly
            370                 375                 380
Trp Gly Lys Ala Val Tyr Gly Gly Pro Ala Lys Gly Val Gly Ala
385                 390                 395                 400
Ile Pro Gly Val Ala Ser Phe Tyr Ile Pro Phe Lys Asn Lys Lys Gly
                405                 410                 415
Glu Asn Gly Ile Val Val Pro Ile Cys Leu Pro Gly Phe Ala Met Glu
            420                 425                 430
Thr Phe Val Lys Glu Leu Asp Gly Met Leu Lys Val Asp Ala Pro Leu
            435                 440                 445
Val Asn Ser Asn Tyr Ala Ile Ile Arg Pro Ala Leu
450                 455                 460
```

<210> SEQ ID NO 72
<211> LENGTH: 455
<212> TYPE: PRT
<213> ORGANISM: Cucumis melo

<400> SEQUENCE: 72

```
Asp Phe Ser Phe His Val Arg Lys Cys Gln Pro Glu Leu Ile Ala Pro
1               5                   10                  15
Ala Asn Pro Thr Pro Tyr Glu Phe Lys Gln Leu Ser Asp Val Asp Asp
                20                  25                  30
Gln Gln Ser Leu Arg Leu Gln Leu Pro Phe Val Asn Ile Tyr Pro His
            35                  40                  45
Asn Pro Ser Leu Glu Gly Arg Asp Pro Val Lys Val Ile Lys Glu Ala
        50                  55                  60
Ile Gly Lys Ala Leu Val Phe Tyr Tyr Pro Leu Ala Gly Arg Leu Arg
65              70                  75                  80
Glu Gly Pro Gly Arg Lys Leu Phe Val Glu Cys Thr Gly Glu Gly Ile
                85                  90                  95
Leu Phe Ile Glu Ala Asp Ala Asp Val Ser Leu Glu Glu Phe Trp Asp
                100                 105                 110
Thr Leu Pro Tyr Ser Leu Ser Ser Met Gln Asn Asn Ile Ile His Asn
            115                 120                 125
Ala Leu Asn Ser Asp Glu Val Leu Asn Ser Pro Leu Leu Leu Ile Gln
        130                 135                 140
Val Thr Arg Leu Lys Cys Gly Gly Phe Ile Phe Gly Leu Cys Phe Asn
145                 150                 155                 160
His Thr Met Ala Asp Gly Phe Gly Ile Val Gln Phe Met Lys Ala Thr
                165                 170                 175
Ala Glu Ile Ala Arg Gly Ala Phe Ala Pro Ser Ile Leu Pro Val Trp
            180                 185                 190
```

-continued

```
Gln Arg Ala Leu Leu Thr Ala Arg Asp Pro Pro Arg Ile Thr Phe Arg
            195                 200                 205

His Tyr Glu Tyr Asp Gln Val Val Asp Met Lys Ser Gly Leu Ile Pro
        210                 215                 220

Val Asn Ser Lys Ile Asp Gln Leu Phe Phe Ser Gln Leu Gln Ile
225                 230                 235                 240

Ser Thr Leu Arg Gln Thr Leu Pro Ala His Leu His Asp Cys Pro Ser
                245                 250                 255

Phe Glu Val Leu Thr Ala Tyr Val Trp Arg Leu Arg Thr Ile Ala Leu
            260                 265                 270

Gln Phe Lys Pro Glu Glu Val Arg Phe Leu Cys Val Met Asn Leu
        275                 280                 285

Arg Ser Lys Ile Asp Ile Pro Leu Gly Tyr Tyr Gly Asn Ala Val Val
    290                 295                 300

Val Pro Ala Val Ile Thr Thr Ala Ala Lys Leu Cys Gly Asn Pro Leu
305                 310                 315                 320

Gly Tyr Ala Val Asp Leu Ile Arg Lys Ala Lys Ala Lys Ala Thr Met
                325                 330                 335

Glu Tyr Ile Lys Ser Thr Val Asp Leu Met Val Ile Lys Gly Arg Pro
            340                 345                 350

Tyr Phe Thr Val Val Gly Ser Phe Met Met Ser Asp Leu Thr Arg Ile
        355                 360                 365

Gly Val Glu Asn Val Asp Phe Gly Trp Gly Lys Ala Ile Phe Gly Gly
    370                 375                 380

Pro Thr Thr Thr Gly Ala Arg Ile Thr Arg Gly Leu Val Ser Phe Cys
385                 390                 395                 400

Val Pro Phe Met Asn Arg Asn Gly Glu Lys Gly Thr Ala Leu Ser Leu
                405                 410                 415

Cys Leu Pro Pro Pro Ala Met Glu Arg Phe Arg Ala Asn Val His Ala
            420                 425                 430

Ser Leu Gln Val Lys Gln Val Val Asp Ala Val Asp Ser His Met Gln
        435                 440                 445

Thr Ile Gln Ser Ala Ser Lys
    450                 455

<210> SEQ ID NO 73
<211> LENGTH: 445
<212> TYPE: PRT
<213> ORGANISM: Arabidopsis thaliana

<400> SEQUENCE: 73

Met Ser Ile Gln Ile Lys Gln Ser Thr Met Val Arg Pro Ala Glu Glu
1               5                   10                  15

Thr Pro Asn Lys Ser Leu Trp Leu Ser Asn Ile Asp Met Ile Leu Arg
            20                  25                  30

Thr Pro Tyr Ser His Thr Gly Ala Val Leu Ile Tyr Lys Gln Pro Asp
        35                  40                  45

Asn Asn Glu Asp Asn Ile His Pro Ser Ser Met Tyr Phe Asp Ala
    50                  55                  60

Asn Ile Leu Ile Glu Ala Leu Ser Lys Ala Leu Val Pro Phe Tyr Pro
65                  70                  75                  80

Met Ala Gly Arg Leu Lys Ile Asn Gly Asp Arg Tyr Glu Ile Asp Cys
                85                  90                  95

Asn Ala Glu Gly Ala Leu Phe Val Glu Ala Glu Ser Ser His Val Leu
            100                 105                 110
```

Glu Asp Phe Gly Asp Phe Arg Pro Asn Asp Glu Leu His Arg Val Met
            115                 120                 125

Val Pro Thr Cys Asp Tyr Ser Lys Gly Ile Ser Ser Phe Pro Leu Leu
        130                 135                 140

Met Val Gln Leu Thr Arg Phe Arg Cys Gly Val Ser Ile Gly Phe
145                 150                 155                 160

Ala Gln His His His Val Cys Asp Gly Met Ala His Phe Glu Phe Asn
                165                 170                 175

Asn Ser Trp Ala Arg Ile Ala Lys Gly Leu Leu Pro Ala Leu Glu Pro
            180                 185                 190

Val His Asp Arg Tyr Leu His Leu Arg Pro Arg Asn Pro Pro Gln Ile
        195                 200                 205

Lys Tyr Ser His Ser Gln Phe Glu Pro Phe Val Pro Ser Leu Pro Asn
    210                 215                 220

Glu Leu Asp Gly Lys Thr Asn Lys Ser Gln Thr Leu Phe Ile Leu
225                 230                 235                 240

Ser Arg Glu Gln Ile Asn Thr Leu Lys Gln Lys Leu Asp Leu Ser Asn
                245                 250                 255

Asn Thr Thr Arg Leu Ser Thr Tyr Glu Val Val Ala Ala His Val Trp
            260                 265                 270

Arg Ser Val Ser Lys Ala Arg Gly Leu Ser Asp His Glu Glu Ile Lys
        275                 280                 285

Leu Ile Met Pro Val Asp Gly Arg Ser Arg Ile Asn Asn Pro Ser Leu
    290                 295                 300

Pro Lys Gly Tyr Cys Gly Asn Val Val Phe Leu Ala Val Cys Thr Ala
305                 310                 315                 320

Thr Val Gly Asp Leu Ser Cys Asn Pro Leu Thr Asp Thr Ala Gly Lys
                325                 330                 335

Val Gln Glu Ala Leu Lys Gly Leu Asp Asp Tyr Leu Arg Ser Ala
        340                 345                 350

Ile Asp His Thr Glu Ser Lys Pro Gly Leu Pro Val Pro Tyr Met Gly
    355                 360                 365

Ser Pro Glu Lys Thr Leu Tyr Pro Asn Val Leu Val Asn Ser Trp Gly
370                 375                 380

Arg Ile Pro Tyr Gln Ala Met Asp Phe Gly Trp Gly Ser Pro Thr Phe
385                 390                 395                 400

Phe Gly Ile Ser Asn Ile Phe Tyr Asp Gly Gln Cys Phe Leu Ile Pro
                405                 410                 415

Ser Arg Asp Gly Asp Gly Ser Met Thr Leu Ala Ile Asn Leu Phe Ser
        420                 425                 430

Ser His Leu Ser Arg Phe Lys Lys Tyr Phe Tyr Asp Phe
    435                 440                 445

<210> SEQ ID NO 74
<211> LENGTH: 446
<212> TYPE: PRT
<213> ORGANISM: Arabidopsis thaliana

<400> SEQUENCE: 74

Met Glu Thr Met Thr Met Lys Val Glu Thr Ile Ser Lys Glu Ile Ile
1               5                   10                  15

Lys Pro Ser Ser Pro Thr Pro Asn Asn Leu Gln Thr Leu Gln Leu Ser
            20                  25                  30

Ile Tyr Asp His Ile Leu Pro Pro Val Tyr Thr Val Ala Phe Leu Phe

-continued

```
              35                  40                  45
Tyr Thr Lys Asn Asp Leu Ile Ser Gln Glu His Thr Ser His Lys Leu
         50                  55                  60

Lys Thr Ser Leu Ser Glu Thr Leu Thr Lys Phe Tyr Pro Leu Ala Gly
 65                  70                  75                  80

Arg Ile Thr Gly Val Thr Val Asp Cys Thr Asp Glu Gly Ala Ile Phe
                 85                  90                  95

Val Asp Ala Arg Val Asn Asn Cys Pro Leu Thr Glu Phe Leu Lys Cys
                100                 105                 110

Pro Asp Phe Asp Ala Leu Gln Gln Leu Leu Pro Leu Asp Val Val Asp
                115                 120                 125

Asn Pro Tyr Val Ala Ala Thr Trp Pro Leu Leu Val Lys Ala
130                 135                 140

Thr Tyr Phe Gly Cys Gly Met Ala Ile Gly Ile Cys Ile Thr His
145                 150                 155                 160

Lys Ile Ala Asp Ala Ala Ser Ile Ser Thr Phe Ile Arg Ser Trp Ala
                165                 170                 175

Ala Thr Ala Arg Gly Glu Asn Asp Ala Ala Met Glu Ser Pro Val
                180                 185                 190

Phe Ala Gly Ala Asn Phe Tyr Pro Pro Ala Asn Glu Ala Phe Lys Leu
                195                 200                 205

Pro Ala Asp Glu Gln Ala Gly Lys Arg Ser Ser Ile Thr Lys Arg Phe
210                 215                 220

Val Phe Glu Ala Ser Lys Val Glu Asp Leu Arg Thr Lys Ala Ala Ser
225                 230                 235                 240

Glu Glu Thr Val Asp Gln Pro Thr Arg Val Glu Ser Val Thr Ala Leu
                245                 250                 255

Ile Trp Lys Cys Phe Val Ala Ser Ser Lys Thr Thr Cys Asp His
                260                 265                 270

Lys Val Leu Val Gln Leu Ala Asn Leu Arg Ser Lys Ile Pro Ser Leu
                275                 280                 285

Leu Gln Glu Ser Ser Ile Gly Asn Leu Met Phe Ser Ser Val Val Leu
290                 295                 300

Ser Ile Gly Arg Gly Gly Glu Val Lys Ile Glu Glu Ala Val Arg Asp
305                 310                 315                 320

Leu Arg Lys Lys Lys Glu Glu Leu Gly Thr Val Ile Leu Asp Glu Gly
                325                 330                 335

Gly Ser Ser Asp Ser Ser Ser Met Ile Gly Ser Lys Leu Ala Asn Leu
                340                 345                 350

Met Leu Thr Asn Tyr Ser Arg Leu Ser Tyr Glu Thr His Glu Pro Tyr
                355                 360                 365

Thr Val Ser Ser Trp Cys Lys Leu Pro Leu Tyr Glu Ala Ser Phe Gly
                370                 375                 380

Trp Asp Ser Pro Val Trp Val Gly Asn Val Ser Pro Val Leu Gly
385                 390                 395                 400

Asn Leu Ala Met Leu Ile Asp Ser Lys Asp Gly Gln Gly Ile Glu Ala
                405                 410                 415

Phe Val Thr Leu Pro Glu Glu Asn Met Ser Ser Phe Glu Gln Asn Pro
                420                 425                 430

Glu Leu Leu Ala Phe Ala Thr Met Asn Pro Ser Val Leu Val
                435                 440                 445
```

<210> SEQ ID NO 75

<211> LENGTH: 435
<212> TYPE: PRT
<213> ORGANISM: Arabidopsis thaliana

<400> SEQUENCE: 75

```
Met Glu Ala Lys Leu Glu Val Thr Gly Lys Glu Val Ile Lys Pro Ala
 1               5                  10                  15

Ser Pro Ser Pro Arg Asp Arg Leu Gln Leu Ser Ile Leu Asp Leu Tyr
            20                  25                  30

Cys Pro Gly Ile Tyr Val Ser Thr Ile Phe Phe Tyr Asp Leu Ile Thr
        35                  40                  45

Glu Ser Ser Glu Val Phe Ser Glu Asn Leu Lys Leu Ser Leu Ser Glu
    50                  55                  60

Thr Leu Ser Arg Phe Tyr Pro Leu Ala Gly Arg Ile Glu Gly Leu Ser
 65                  70                  75                  80

Ile Ser Cys Asn Asp Glu Gly Ala Val Phe Thr Glu Ala Arg Thr Asp
                85                  90                  95

Leu Leu Leu Pro Asp Phe Leu Arg Asn Leu Asn Thr Asp Ser Leu Ser
            100                 105                 110

Gly Phe Leu Pro Thr Leu Ala Ala Gly Glu Ser Pro Ala Ala Trp Pro
        115                 120                 125

Leu Leu Ser Val Lys Val Thr Phe Phe Gly Ser Gly Ser Gly Val Ala
    130                 135                 140

Val Ser Val Ser Val Ser His Lys Ile Cys Asp Ile Ala Ser Leu Val
145                 150                 155                 160

Thr Phe Val Lys Asp Trp Ala Thr Thr Thr Ala Lys Gly Lys Ser Asn
                165                 170                 175

Ser Thr Ile Glu Phe Ala Glu Thr Thr Ile Tyr Pro Pro Pro Pro Ser
            180                 185                 190

His Met Tyr Glu Gln Phe Pro Ser Thr Asp Ser Asp Ser Asn Ile Thr
        195                 200                 205

Ser Lys Tyr Val Leu Lys Arg Phe Val Phe Glu Pro Ser Lys Ile Ala
    210                 215                 220

Glu Leu Lys His Lys Ala Ala Ser Glu Ser Val Pro Val Pro Thr Arg
225                 230                 235                 240

Val Glu Ala Ile Met Ser Leu Ile Trp Arg Cys Ala Arg Asn Ser Ser
                245                 250                 255

Arg Ser Asn Leu Leu Ile Pro Arg Gln Ala Val Met Trp Gln Ala Met
            260                 265                 270

Asp Ile Arg Leu Arg Ile Pro Ser Ser Val Ala Pro Lys Asp Val Ile
        275                 280                 285

Gly Asn Leu Gln Ser Gly Phe Ser Leu Lys Lys Asp Ala Glu Ser Glu
    290                 295                 300

Phe Glu Ile Pro Glu Ile Val Ala Thr Phe Arg Lys Asn Lys Glu Arg
305                 310                 315                 320

Val Asn Glu Met Ile Lys Glu Ser Leu Gln Gly Asn Thr Ile Gly Gln
                325                 330                 335

Ser Leu Leu Ser Leu Met Ala Glu Thr Val Ser Glu Ser Thr Glu Ile
            340                 345                 350

Asp Arg Tyr Ile Met Ser Ser Trp Cys Arg Lys Pro Phe Tyr Glu Val
        355                 360                 365

Asp Phe Gly Ser Gly Ser Pro Val Trp Val Gly Tyr Ala Ser His Thr
    370                 375                 380

Ile Tyr Asp Asn Met Val Gly Val Val Leu Ile Asp Ser Lys Glu Gly
```

```
                385                 390                 395                 400
Asp Gly Val Glu Ala Trp Ile Ser Leu Pro Glu Glu Asp Met Ser Val
                    405                 410                 415

Phe Val Asp Asp Gln Glu Leu Leu Ala Tyr Ala Val Leu Asn Pro Pro
                420                 425                 430

Val Val Ala
        435

<210> SEQ ID NO 76
<211> LENGTH: 458
<212> TYPE: PRT
<213> ORGANISM: Arabidopsis thaliana

<400> SEQUENCE: 76

Met Pro Met Leu Met Ala Thr Arg Ile Asp Ile Ile Gln Lys Leu Asn
 1               5                  10                  15

Val Tyr Pro Arg Phe Gln Asn His Asp Lys Lys Leu Ile Thr Leu
            20                  25                  30

Ser Asn Leu Asp Arg Gln Cys Pro Leu Leu Met Tyr Ser Val Phe Phe
            35                  40                  45

Tyr Lys Asn Thr Thr Arg Asp Phe Asp Ser Val Phe Ser Asn Leu
        50                  55                  60

Lys Leu Gly Leu Glu Thr Met Ser Val Trp Tyr Pro Ala Ala Gly
 65                  70                  75                  80

Arg Leu Gly Leu Asp Gly Gly Cys Lys Leu Asn Ile Arg Cys Asn
                 85                  90                  95

Asp Gly Gly Ala Val Met Val Glu Ala Val Ala Thr Gly Val Lys Leu
                100                 105                 110

Ser Glu Leu Gly Asp Leu Thr Gln Tyr Asn Glu Phe Tyr Glu Asn Leu
            115                 120                 125

Val Tyr Lys Pro Ser Leu Asp Gly Asp Phe Ser Val Met Pro Leu Val
        130                 135                 140

Val Ala Gln Val Thr Arg Phe Ala Cys Gly Gly Tyr Ser Ile Gly Ile
145                 150                 155                 160

Gly Thr Ser His Ser Leu Phe Asp Gly Ile Ser Ala Tyr Glu Phe Ile
                165                 170                 175

His Ala Trp Ala Ser Asn Ser His Ile His Asn Lys Ser Asn Ser Lys
                180                 185                 190

Ile Thr Asn Lys Lys Glu Asp Val Val Ile Lys Pro Val His Asp Arg
            195                 200                 205

Arg Asn Leu Leu Val Asn Arg Asp Ala Val Arg Glu Thr Asn Ala Ala
        210                 215                 220

Ala Ile Cys His Leu Tyr Gln Leu Ile Lys Gln Ala Met Met Thr Tyr
225                 230                 235                 240

Gln Glu Gln Asn Arg Asn Leu Glu Leu Pro Asp Ser Gly Phe Val Ile
                245                 250                 255

Lys Thr Phe Glu Leu Asn Gly Asp Ala Ile Glu Ser Met Lys Lys Lys
                260                 265                 270

Ser Leu Glu Gly Phe Met Cys Ser Ser Phe Glu Phe Leu Ala Ala His
            275                 280                 285

Leu Trp Lys Ala Arg Thr Arg Ala Leu Gly Leu Arg Arg Asp Ala Met
        290                 295                 300

Val Cys Leu Gln Phe Ala Val Asp Ile Arg Lys Arg Thr Glu Thr Pro
305                 310                 315                 320
```

```
-continued

Leu Pro Glu Gly Phe Ser Gly Asn Ala Tyr Val Leu Ala Ser Val Ala
            325             330             335

Ser Thr Ala Arg Glu Leu Leu Glu Glu Leu Thr Leu Glu Ser Ile Val
            340             345             350

Asn Lys Ile Arg Glu Ala Lys Lys Ser Ile Asp Gln Gly Tyr Ile Asn
        355             360             365

Ser Tyr Met Glu Ala Leu Gly Gly Ser Asn Asp Gly Asn Leu Pro Pro
    370             375             380

Leu Lys Glu Leu Thr Leu Ile Ser Asp Trp Thr Lys Met Pro Phe His
385             390             395             400

Asn Val Gly Phe Gly Asn Gly Gly Glu Pro Ala Asp Tyr Met Ala Pro
            405             410             415

Leu Cys Pro Pro Val Pro Gln Val Ala Tyr Phe Met Lys Asn Pro Lys
            420             425             430

Asp Ala Lys Gly Val Leu Val Arg Ile Gly Leu Asp Pro Arg Asp Val
            435             440             445

Asn Gly Phe Ser Asn His Phe Leu Asp Cys
    450             455
```